US008598155B2

(12) United States Patent
Helal et al.

(10) Patent No.: US 8,598,155 B2
(45) Date of Patent: Dec. 3, 2013

(54) IMIDAZO[5,1-F][1,2,4]TRIAZINES FOR THE TREATMENT OF NEUROLOGICAL DISORDERS

(75) Inventors: Christopher John Helal, Mystic, CT (US); Thomas Allen Chappie, Old Lyme, CT (US); John Michael Humphrey, Mystic, CT (US); Patrick Robert Verhoest, Old Lyme, CT (US); Eddie Yang, Oakdale, CT (US)

(73) Assignee: Pfizer Inc., New York, NY (US)

( * ) Notice: Subject to any disclaimer, the term of this patent is extended or adjusted under 35 U.S.C. 154(b) by 80 days.

(21) Appl. No.: 13/400,172

(22) Filed: Feb. 20, 2012

(65) Prior Publication Data

US 2012/0214791 A1  Aug. 23, 2012

Related U.S. Application Data

(60) Provisional application No. 61/445,617, filed on Feb. 23, 2011.

(51) Int. Cl.
*A61K 31/397* (2006.01)
*A61K 31/53* (2006.01)
*C07D 487/04* (2006.01)

(52) U.S. Cl.
USPC ............. 514/210.21; 514/243; 544/184

(58) Field of Classification Search
USPC ............. 514/210.21, 243; 544/184
See application file for complete search history.

(56) References Cited

U.S. PATENT DOCUMENTS

| 8,101,613 B2 | 1/2012 | Arnold et al. ............ 514/249 |
| 2004/0249148 A1 | 12/2004 | Erguden et al. |
| 2006/0019957 A1 | 1/2006 | Crew et al. ............ 514/243 |
| 2006/0084650 A1 | 4/2006 | Dong et al. |
| 2006/0154931 A1 | 7/2006 | Verhoest et al. ............ 514/249 |
| 2006/0166993 A1 | 7/2006 | Hendrix et al. |
| 2006/0235031 A1 | 10/2006 | Arnold et al. ............ 514/263.2 |
| 2007/0112005 A1 | 5/2007 | Chen et al. ............ 514/243 |
| 2008/0139582 A1 | 6/2008 | Honigberg et al. ...... 514/262.1 |
| 2008/0280907 A1 | 11/2008 | Schmidt et al. .......... 514/236.2 |
| 2009/0286768 A1 | 11/2009 | Crew et al. ............ 514/210.21 |
| 2011/0015197 A1 | 1/2011 | Casterhano et al. ........ 514/243 |

FOREIGN PATENT DOCUMENTS

| WO | WO 2005041957 | 5/2005 |
| WO | WO 2005097800 | 10/2005 |
| WO | WO 2007087395 | 8/2007 |
| WO | WO 2007106503 | 9/2007 |
| WO | WO 2009008992 | 1/2009 |
| WO | WO 2009117482 | 1/2009 |
| WO | WO 2011005909 | 1/2011 |

OTHER PUBLICATIONS

PCT/IB2012/050589 International Search Report and Written Opinion, dated Apr. 4, 2012, 13 pages.
Rosman, G.J., et al., "Isolation and characterization of human cDNAs encoding a cGMP-stimulated 3', 5'-cyclic nucleotide phosphodiesterase", Gene, 1997, pp. 89-95, 191(1).
Boess, F. G., et al., "Inhibition of phosphodiesterase 2 increases neuronal cGMP, synaptic plasticity and memory performance", Neuropharmacology, 2004, pp. 1081-1092, 47(7).
Domek-Lopacinski, K., et al., "The effect of selective inhibition of cyclic GMP hydrolyzing phosphodiesterases 2 and 5 on learning and memory processes and nitric oxide synthase activity in brain during aging", Brian Research, Jun. 24, 2008, pp. 68-77, vol. 1216.
Brandon, N., et al., "Potential CNS Applications for Phosphodiesterase Enzyme Inhibitors", Annual Reports in Medicinal Chemistry 2007, Chapter 1, pp. 3-12, vol. 42.
Masood, A., et al., "Anxiolytic Effects of Phosphodiesterase-2 Inhibitors Associated with Increased cGMP Signaling", Journal of Pharmacology and Experimental Therapeutics, 2009, pp. 690-699, 331(2).
Masood, A., et al., Reversal of Oxidative Stress-Induced Anxiety by Inhibition of Phosphodiesterase-2 in Mice, Journal of Pharmacology and Experimental Therapeutics, Aug. 1, 2008, pp. 369-379, 326(2).
Reierson, G.W., et al., "Repeated antidepressant therapy increases cyclic GMP signaling in rat hippocampus", Neuroscience Letters, Dec. 11, 2009, pp. 149-153, 466(3).
Schmidtko, A., et al., "cGMP Produced by NO-Sensitive Guanylyl Cyclase Essentially Contributes to Inflammatory and Neuropathic Pain by Using Targets Different from cGMP-Dependent Protein Kinase I", The Journal of Neuroscience, Aug. 20, 2008, pp. 8568-8576, 28(34).
Seybold, J., et al., "Tumor necrosis factor-α-dependent expression of phosphodiesterase 2: role in endothelial hyperpermeability", Blood, May 1, 2005, pp. 3569-3576, 105(9).
Kayhan, N., et al., "The adenosine deaminase inhibitor erythro-9-[2-hydroxyl-3-nonyl]-adenine decreases intestinal permeability and protects against experimental sepsis: a prospective, randomized laboratory investigation", Critical Care, Oct. 13, 2008, pp. R125, 12(5).
Suzuki, A., "Recent advances in the cross-coupling reactions of organoboron derivatives with organic electrophiles, 1995-1998", Journal of Organometallic Chemistry, Mar. 15, 1999, pp. 147-168, 576(1-2).

(Continued)

*Primary Examiner* — Samantha Shterengarts
(74) *Attorney, Agent, or Firm* — Richard V. Zanzalari

(57) ABSTRACT

The present invention relates to compounds of the Formula

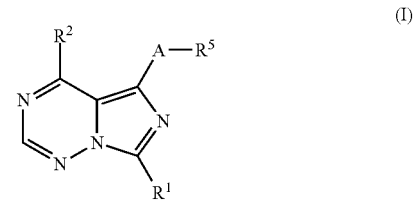

(I)

and pharmaceutically acceptable salts thereof, to processes for the preparation of, intermediates used in the preparation of, and compositions containing such compounds and the uses of such compounds as a method for the treatment of a disease or condition selected from the group consisting of central nervous system disorders, cognitive disorders, schizophrenia, dementia and other disorders in a mammal.

26 Claims, No Drawings

(56) References Cited

OTHER PUBLICATIONS

Miyaura, N., et al., "Palladium-Catalyzed Cross-Coupling Reactions of Organoboron Compounds", Chemical Review, 1995, pp. 2457-2483, 95(7).

Littke, A.F., et al., "Versatile Catalysts for the Suzuki Cross-Coupling of Arylboronic Acids with Aryl and Vinyl Halides and Triflates under Mild Conditions", Journal of the American Chemical Society., Apr. 15, 2000, pp. 4020-4028, 122(17).

Erdik, E., "Transition Metal Catalyzed Reactions of Organozinc Reagents", Tetrahedron, 1992, pp. 9577-9648, 48(44).

Lam, P.Y.S., et al., "New Aryl/Heteroaryl C—N Bond Cross-coupling Reactions via Arylboronic Acid/Cupric Acetate Arylation", Tetrahedron Letters, 1998, pp. 2941-2944, 39(19).

Xi, Z., et al., "CuI/L (L-pyridine-functionalized 1,3-diketones) catalyzed C—N coupling reactions of aryl halides with NH-containing heterocycles", Tetrahedron, 2008, pp. 4254-4259, 64(19).

Hendricks, R.T., et al.,"3-Hydroxyisoquinolines as inhibitors of HCV NS5b RNA-dependent RNA polymerase", Bioorganic & Medicinal Chemistry Letters, 2009, pp. 410-414, 19(2).

Ottesen, L.K., et al., "Iron-Catalyzed Cross-Coupling of Imidoyl Chlorides with Grignard Reagents", Organic Letter, 2006, pp. 1771-1773, 8(9).

Bodendiek, S.B., et al., "4-Phenoxybutoxy-substituted heterocycles—A structure-activity relationship study of blockers of the lymphocyte potassium channel Kv1.3", European Journal of Medicinal Chemistry 2009, pp. 1838-1852, 44(5).

Khattab, A.F., et al., "Simple Analogues of Acyclonucleosides: Synthesis of N-Substituted Pyrido [3',2' :4,5] thieno [3,2-d] pyrimidine Derivative", Synthetic Communications., 2006, pp. 2751-2761, 36(19).

Smith, G., et al., "Design, Synthesis, and Biological Characterization of a Caspase 3/7 Selective Isatin Labeled with 2-[$^{18}$F]fluoroethylazide", Journal of Medicinal Chemistry, 2008, pp. 8057-8067, 51(24).

Shireman, B.T., et al., "2-Alky-4-aryl-pyrimidine fused heterocycles as selective 5-$HT_{2A}$ antagonists", Bioorganic & Medicinal Chemistry Letters, Mar. 15, 2008, pp. 2103-2108, 18(6).

Hurtaud, D., et al., "Epoxy Imidates Highly Reactive Precursors of Epoxy Acylamidrazones, 3, 5-Diaminopyrazoles and 3, 4-Dihydro-2, 2'-Biquinozalines", Synthesis, 2001, pp. 2435-2440, 2001(16).

Yang, X., et al., "Novel Oxadiazole Analogues Derived from Ethacrynic Acid: Design, Synthesis, and Structure-Activity Relationships in Inhibiting the Activity of Glutathione S-Transferase P1-1 and Cancer Cell Proliferation", Journal of Medicinal Chemistry, Jan. 7, 2010, pp. 1015-1022, 53(3).

Shao, N., et al., "Efficient one-pot formation of 4-N-substituted 2,4-dihydro-3H-1,2,4-triazolin-3-ones from primary amines using N'-(ethoxymethylene)hydrazinecarboxylic acid methyl ester", Tetrahedron Letter, 2006, pp. 6743-6746, 47(38).

Hatanaka, M., "Preparation and antioxidant activity of α-pyridoin and its derivatives", Bioorganic & Medicinal Chemistry, 2005, pp. 6763-6770, 13(24).

Podzuweit, et al., "Isozyme selective inhibition of cGMP-stimulated cyclic nucleotide phosphodiesterases by erythro-9-(2-hydroxy-3-nonyl) adenine", Cell ular Signalling, Sep. 1995, pp. 733-738, 7(7).

IMIDAZO[5,1-F][1,2,4]TRIAZINES FOR THE TREATMENT OF NEUROLOGICAL DISORDERS

This application is a Non-Provisional application under 35 U.S.C. 119(e) which claims the benefit of U.S. Patent Application No. 61/445,617 filed on Feb. 23, 2011.

FIELD OF THE INVENTION

This invention relates to imidazo[5,1-f][1,2,4]triazines, which are selective inhibitors of PDE2. The invention further relates to intermediates for preparation of such compounds; pharmaceutical compositions comprising such compounds; and the use of such compounds in methods for treating certain central nervous system (CNS) or other disorders. The invention relates also to methods for treating neurodegenerative or psychiatric disorders, including psychosis, impaired cognition, schizophrenia, depression, dementia and other disorders in a mammal.

BACKGROUND OF THE INVENTION

Phosphodiesterases (PDEs) are a class of intracellular enzymes involved in the hydrolysis of the nucleotides cyclic adenosine monophosphate (cAMP) and cyclic guanosine monophosphate (cGMP) to their respective nucleotide monophosphates. These cyclic nucleotides serve as secondary messengers in several cellular pathways, regulating an array of intracellular processes within neurons of the central nervous system including the activation of cAMP- and cGMP-dependent protein kinases that produce subsequent phosphorylation of proteins involved in regulation of synaptic transmission, synaptic plasticity, neuronal differentiation and survival.

So far, only a single gene for PDE2, PDE2A, has been identified; however, multiple alternatively spliced isoforms of PDE2A, which include PDE2A1, PDE2A2, and PDE2A3, have been reported. PDE2A was identified as a unique family based on primary amino acid sequence and distinct enzymatic activity. The human PDE2A3 sequence was isolated in 1997 (Rosman et al., *Isolation and characterization of human cDNAs encoding a cGMP-stimulated 3',5'-cyclic nucleotide phosphodiesterase*, Gene, 191 (1):89-95, 1997).

Inhibition of PDE2A demonstrates enhanced cognitive function across multiple preclinical models of cognitive performance that reflect improvements in recognition memory, social interactions and working memory, which are all deficient in schizophrenia (Boess et al., *Inhibition of phosphodiesterase 2 increases neuronal cGMP, synaptic plasticity and memory performance*, Neuropharmacology, 47(7):1081-92, 2004). PDE2A inhibition also improved cognitive deficits that develop in aging and Alzheimer's disease (Domek-Lopacinska and Strosznajder, *The effect of selective inhibition of cyclic GMP hydrolyzing phosphodiesterases 2 and 5 on learning and memory processes and nitric oxide synthetase activity in brain during aging*, Brain Research, 1216:68-77, 2008). Bayer has published the biochemical and behavioral profile of BAY 60-7550, indicating a role in PDE2 inhibition in cognitive disorders (Brandon et al., *Potential CNS Applications for Phosphodiesterase Enzyme Inhibitors*, Annual Reports in Medicinal Chemistry 42: 4-5, 2007). However, this compound showed significant potency at other PDE isoforms and had high clearance and limited brain penetration and is not believed to be progressing in the clinic.

PDE2 inhibitors have also been demonstrated to show efficacy in preclinical models of anxiety and depression (Masood et al., *Anxiolytic effects of phosphodiesterase-2 inhibitors associated with increased cGMP signaling*, JPET 331(2):690-699, 2009; Masood et al., *Reversal of Oxidative Stress-Induced Anxiety by Inhibition of Phosphodiesterase-2 in Mice*, JPET 326(2):369-379, 2008; Reierson et al., *Repeated antidepressant therapy increases cyclic GMP signaling in rat hippocampus*, Neurosci. Lett., 466(3):149-53, 2009).

PDE2A protein expressed in the dorsal horn of the spinal cord and dorsal root ganglia enables PDE2A to modulate cyclic nucleotide levels in these regions during processing of neuropathic and inflammatory pain (Schmidtko et al., *cGMP Produced by NO-Sensitive Guanylyl Cyclase Essentially Contributes to Inflammatory and Neuropathic Pain by Using Targets Different from cGMP-Dependent Protein Kinase I*, The Journal of Neuroscience, 28(34):8568-8576, 2008).

In the periphery, the expression of PDE2A in endothelial cells has been demonstrated to play a critical role in regulation of endothelial barrier function. The expression levels of PDE2A in endothelial cells are increased in response to inflammatory cytokines such as TNF-alpha under conditions of sepsis and acute respiratory distress syndrome, and contribute to disruption of endothelial barrier function. Inhibition of PDE2A has been demonstrated to reverse permeability deficits in sepsis and enhance survival rates in animal models of sepsis and endotoxicosis (Seybold et al., *Tumor necrosis factor-{alpha}-dependent expression of phosphodiesterase 2: role in endothelial hyperpermeability*, Blood, 105:3569-3576, 2005; Kayhan et al., *The adenosine deaminase inhibitor erythro-9-[2-hydroxyl-3-nonyl]-adenine decreases intestinal permeability and protects against experimental sepsis: a prospective, randomized laboratory investigation*, Critical Care, 12(5):R125, 2008).

Certain imidazotriazines have been published as kinase inhibitors such as: International Patent Publication WO2011005909 entitled "Process for the preparation of substituted imidazo[5,1-f][1,2,4]triazine derivatives;" United States Patent Publication: US20090286768 entitled "Substituted imidazopyrazines and imidazotriazines as ACK1 inhibitors and their preparation;" International Patent Publication WO2009117482 entitled "Preparation of mTOR inhibitor salt forms;" International Patent Publication: WO2009008992 entitled "Preparation of imidazo[1,5-a]pyrazin-8-amine for use in combination therapy of cancers and cancer metastasis;" United States Patent Publication US20080139582 entitled "Preparation of substituted pyrazolopyrimidinamines as inhibitors of Bruton's tyrosine kinase;" International Patent Publication: WO2007106503 entitled: Imidazo[1,5-a]pyrazin-8-amine in combined treatment with an EGFR kinase inhibitor and an agent that sensitizes tumor cells to the effects of EGFR kinase inhibitors;" International Patent Publication WO2007087395 entitled "Preparation of ethynyl- or vinyl-imidazopyrazines and imidazotriazines as mammalian target of rapamycin (mTOR) inhibitors for the treatment of cancer and other diseases;" United States Patent Publication US20070112005 entitled "Preparation of substituted imidazopyrazines and related compounds as mTOR inhibitors;" United States Patent Publication US20060019957 entitled "Preparation of imidazotriazines as protein kinase inhibitors;" and International Patent Publication WO2005097800 entitled "Preparation of 6,6-bicyclic ring substituted heterobicyclic protein kinase inhibitors"

SUMMARY OF THE INVENTION

The present invention is directed to novel compounds of the Formula

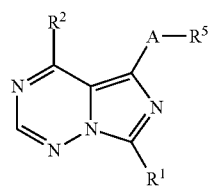

or a pharmaceutically acceptable salt thereof, wherein:
"-A-R⁵" is:

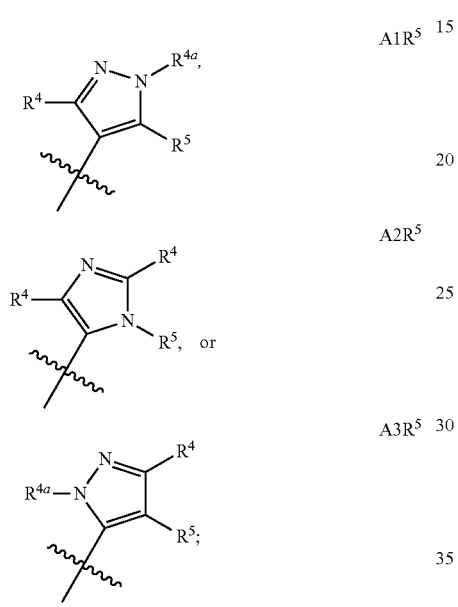

$R^1$ is hydrogen, $(C_1-C_6)$alkyl, $(C_2-C_6)$alkenyl, $(C_2-C_6)$alkynyl, $(C_3-C_{15})$cycloalkyl, $-(C_1-C_6)$alkyl-OH, $-(C_1-C_6)$alkyl-CN, $-SF_5$, $-CF_3$, $-CHF_2$, or $-CH_2F$;

$R^2$ is $-(C_1-C_6)$alkyl-$R^9$, $-NHR^3$, $-N(R^3)_2$, $-O-(C_1-C_6)$alkyl-$R^9$, $-OR^8$, $(C_3-C_{15})$cycloalkyl, $(C_6-C_{10})$aryl, $(C_1-C_{14})$heterocyclic, or $(C_1-C_{14})$heteroaryl; wherein said $(C_3-C_{15})$cycloalkyl and $(C_1-C_{14})$heterocyclic may optionally contain one double or triple bond and one to two oxo (O=) groups; and wherein said $-(C_1-C_6)$alkyl-$R^9$, $-O-(C_1-C_6)$alkyl-$R^9$, $(C_3-C_{15})$cycloalkyl, $(C_6-C_{10})$aryl, $(C_1-C_{14})$heterocyclic, or $(C_1-C_{14})$heteroaryl moieties may be optionally substituted with one to three substituents independently selected from $(C_1-C_6)$alkyl, $(C_1-C_6)$alkoxy, halo, and $-CF_3$, Each $R^3$ is independently selected from the group consisting of $-(C_1-C_6)$alkyl-$R^9$, $-(C_2-C_6)$alkenyl-$R^9$, $-(C_2-C_6)$alkynyl-$R^9$, and $-(C_3-C_{15})$cycloalkyl-$R^9$; or when $R^2$ is $-N(R^3)_2$ both of said $R^3$ may be taken together with the nitrogen atom to which they are attached to form a 4- to 6-membered heterocyclic ring optionally containing one or two oxo groups (O=) and optionally substituted with one to three substituents independently selected from the group consisting of hydrogen, fluoro, $-CN$, $-CF_3$, $-CHF_2$, $-CH_2F$, $-OH$, $-O-(C_1-C_6)$alkyl, $NH_2$, $-NH-(C_1-C_6)$alkyl, $(C_1-C_6)$alkyl, $(C_2-C_6)$alkenyl, $(C_2-C_6)$alkynyl, $-(C=O)-R^8$, $-(C=O)-OR^8$, $-(C=O)-N(R^8)_2$, $-O-(C=O)-R^8$, $-OR^8$, $-O-(C=O)-OR^8$, $-SR^8$, $-S(O)R^8$, $-S(O)_2R^8$, $-S(O)_2N(R^8)_2$, $-NH-(C=O)-R^8$, $-NH-(C=O)-OR^8$, $-O-(C=O)-N(R^8)_2$, $-NH-(C=O)-N(R^8)_2$, $-N[(C_1-C_6)alkyl](C=O)-R^8$, $-N[(C_1-C_6)alkyl](C=O)-OR^8$, $-N[(C_1-C_6)alkyl](C=O)-N(R^8)_2$, $(C_3-C_{15})$cycloalkyl, $(C_6-C_{10})$aryl, $(C_1-C_{14})$heterocyclic and $(C_1-C_{14})$heteroaryl; wherein said $(C_3-C_{16})$cycloalkyl and $(C_1-C_{14})$heterocyclic may optionally contain one double or triple bond and one to two oxo (O=) groups;

Each $R^4$ is independently selected from the group consisting of hydrogen, halo, $(C_1-C_6)$alkyl, $(C_2-C_4)$alkenyl, $(C_2-C_6)$alkynyl, $-CF_3$, $-CHF_2$, $-CH_2F$, or $(C_3-C_{15})$cycloalkyl;

$R^{4a}$ is hydrogen, $(C_1-C_6)$alkyl, $(C_3-C_4)$alkenyl, $(C_3-C_4)$alkynyl, $-CF_3$, $-CHF_2$, $-CH_2F$, or $(C_3-C_{15})$cycloalkyl;

$R^5$ is:

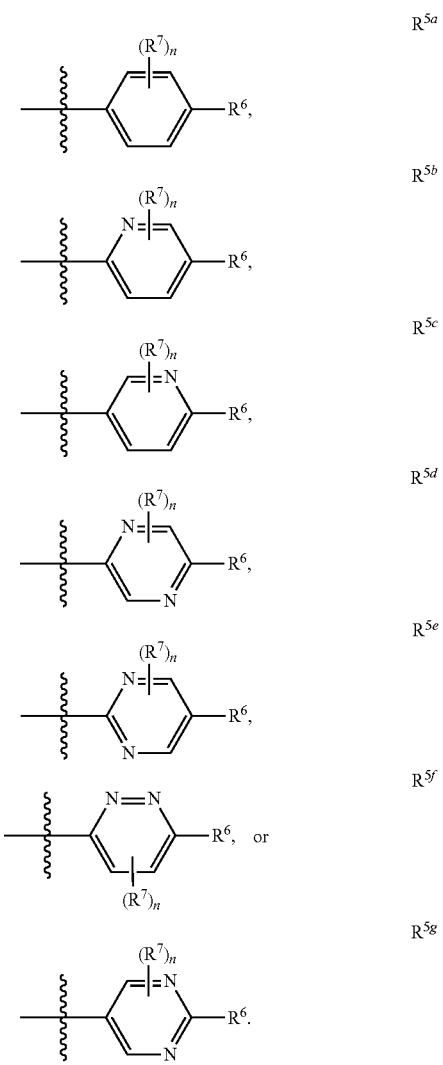

where n is 0, 1, 2, 3, or 4;

Each $R^6$ is independently selected from the group consisting of hydrogen, halo, $(C_1-C_6)$alkyl, $-CF_3$, $-CHF_2$, $-CH_2F$, $-CF_2-(C_1-C_6)$alkyl, $-SF_5$, $-CN$, $-(C_1-C_6)$alkyl-CN, $-NO_2$, $-(C=O)-R^8$, $-(C=O)-OR^8$, $-OR^8$, $-O-(C=O)-N(R^8)_2$, $-SR^8$, $-S(O)R^8$, $-S(O)_2R^8$, $NH_2$, $-NH-(C_1-C_6)$alkyl, $-N[(C_1-C_6)alkyl]_2$, $-NH-(C=O)-R^8$, $-NH-(C=O)-OR^8$, $-N[(C_1-C_6)alkyl](C=O)-R^8$, $-N[(C_1-C_6)alkyl](C=O)-OR^8$, $(C_1-C_6)$alkyl, $(C_2-C_6)$alkenyl, $(C_2-C_6)$alkynyl, $(C_3-C_{15})$cycloalkyl, $(C_1-C_{14})$heterocyclic, $(C_6-C_{10})$aryl, and $(C_1-C_{14})$heteroaryl; wherein said $(C_3-C_{15})$cycloalkyl, $(C_1-C_{14})$ heterocyclic, and $(C_1-C_{14})$heteroaryl may optionally contain one double or triple bond and one to two oxo (O=) groups;

Each $R^7$ is independently selected from the group consisting of hydrogen, halo, $(C_1-C_6)$alkyl, $(C_2-C_4)$alkenyl, $(C_2-C_6)$alkynyl, —CN, —$CF_3$, —$CHF_2$, —$CH_2F$, —O—$(C_1-C_6)$alkyl and $(C_3-C_{15})$cycloalkyl;

Each $R^8$ wherever it occurs is independently selected from the group consisting of hydrogen, $(C_1-C_6)$alkyl, $(C_3-C_{15})$cycloalkyl, —$CF_3$, and —$CHF_2$; and Each $R^9$ is independently selected from the group consisting of hydrogen, halo, —$CF_3$, —$CHF_2$, —$CH_2F$, —$CF_2$—$(C_1-C_6)$alkyl, —CN, —$(C_1-C_6)$alkyl-CN, —$NO_2$, —(C=O)—$R^8$, —(C=O)—$OR^8$, —$OR^8$, —O—(C=O)—$N(R^8)_2$, —$SR^8$, —S(O)$R^8$, —S(O)$_2R^8$, $NH_2$, —NH—$(C_1$-$C_6)$alkyl, —NH—(C=O)—$R^8$, —NH—(C=O)—$OR^8$, —N[$(C_1-C_6)$alkyl](C=O)—$R^8$, —N[$(C_1-C_6)$alkyl](C=O)—$OR^8$, $(C_1-C_6)$alkyl, $(C_2-C_6)$alkenyl, $(C_2-C_6)$alkynyl, $(C_3-C_{15})$cycloalkyl, $(C_1-C_{14})$heterocyclic, $(C_6-C_{10})$aryl, and $(C_1-C_{14})$heteroaryl; wherein said $(C_3-C_{15})$cycloalkyl, $(C_1-C_{14})$heterocyclic, and may optionally contain one double or triple bond and one to two oxo (O=) groups; and wherein each of said $(C_3-C_{15})$cycloalkyl, $(C_1-C_{14})$heterocyclic, $(C_6$-$C_{10})$aryl, and $(C_1-C_{14})$heteroaryl moieties may be optionally substituted with one to three substituents independently selected from $(C_1-C_6)$alkyl, $(C_1-C_6)$alkoxy, halo, and —$CF_3$.

As used herein, the term "alkyl" is defined to include saturated aliphatic hydrocarbons including straight chains and branched chains. Preferably, the alkyl group has 1 to 6 carbon atoms. For example, as used herein, the term "$(C_1-C_6)$alkyl," as well as the alkyl moieties of other groups referred to herein (e.g., $(C_1-C_6)$alkoxy), refers to linear or branched radicals of 1 to 6 carbon atoms (e.g., methyl, ethyl, n-propyl, isopropyl, n-butyl, isobutyl, sec-butyl, tert-butyl), optionally substituted by 1 to 5 suitable substituents.

Whenever a numerical range is used in this application, for example when 1 to 6 is used in the definition of "alkyl", it means that the alkyl group may contain 1 carbon atom, 2 carbon atoms, 3 carbon atoms, etc. up to and including 6 carbon atoms.

As used herein, the term "alkenyl" is defined to include aliphatic hydrocarbons having at least one carbon-carbon double bond, including straight chains and branched chains having at least one carbon-carbon double bond. Preferably, the alkenyl group has 2 to 6 carbon atoms. More preferably, the alkenyl group has 2 to 4 carbon atoms. For example, as used herein, the term "$(C_2-C_6)$alkenyl" means straight or branched chain unsaturated radicals of 2 to 6 carbon atoms, including, but not limited to, ethenyl, 1-propenyl, 2-propenyl (allyl), isopropenyl, 2-methyl-1-propenyl, 1-butenyl, 2-butenyl, and the like, optionally substituted by 1 to 5 suitable substituents. When the compounds of Formula I contain an alkenyl group, the alkenyl group may exist as the pure E (entgegen) form, the pure Z (zusammen) form, or any mixture thereof.

As used herein, the term "alkynyl" is defined to include aliphatic hydrocarbons having at least one carbon-carbon triple bond, including straight chains and branched chains having at least one carbon-carbon triple bond. Preferably, the alkynyl group has has 2 to 6 carbon atoms. For example, as used herein, the term "$(C_2-C_6)$alkynyl" is used herein to mean straight or branched hydrocarbon chain alkynyl radicals as defined above, having 2 to 6 carbon atoms and one triple bond, optionally substituted by 1 to 5 suitable substituents.

As used herein, the term "cycloalkyl" is defined to include saturated or unsaturated (non-aromatic) monocyclic or bicyclic hydrocarbon rings (e.g., monocyclics such as cyclopropyl, cyclobutyl, cyclopentyl, cyclohexyl, cycloheptyl, cyclooctyl, or cyclononyl or bicyclics including bridged or fused systems such as bicyclo[2.2.1]heptanyl, bicyclo[3.2.1]octanyl or bicyclo[5.2.0]nonanyl, etc.), optionally substituted by 1 to 5 suitable substituents. The cycloalkyl group has 3 to 15 carbon atoms. In one embodiment the cycloalkyl may optionally contain one, two or more non-cumulative non-aromatic double or triple bonds and one to three oxo groups. Preferably, the bicycloalkyl group has 6 to 15 carbon atoms. The bicycloalkyl is optionally substituted by 1 to 5 suitable substituents. In one embodiment the bicycloalkyl may optionally contain one, two or more non-cumulative non-aromatic double or triple bonds As used herein, the term "aryl" is defined to include all-carbon monocyclic or fused-ring polycyclic groups having a conjugated pi-electron system. The aryl group has 6, 8, or 10 carbon atoms in the ring(s). More commonly, the aryl group has 6 or 10 carbon atoms in the ring(s). Most commonly, the aryl group has 6 carbon atoms in the ring. For example, as used herein, the term "$(C_6-C_{10})$aryl" means aromatic radicals containing from 6 to 10 carbon atoms such as phenyl, naphthyl, tetrahydronaphthyl, indanyl and the like. The aryl group is optionally substituted by 1 to 5 suitable substituents.

As used herein, the term "heteroaryl" is defined to include monocyclic or fused-ring polycyclic aromatic heterocyclic groups with one or more heteroatoms selected from O, S and N in at least one ring. The heteroaryl group has 5 to 14 ring atoms, including 1 to 13 carbon atoms, and 1 to 5 heteroatoms selected from O, S, and N. Preferably, the heteroaryl group has 5 to 10 ring atoms including one to four heteroatoms. The heteroaryl group also contains one to three oxo groups. More preferably, the heteroaryl group has 5 to 8 ring atoms including one, two or three heteroatoms. Monocyclic heteroaryls of particular interest include those with 5 ring atoms including one to three heteroatoms or those with 6 ring atoms including one or two nitrogen heteroatoms. Fused bicyclic heteroaryls of particular interest include two fused 5 and/or 6 membered monocyclic rings including one to four heteroatoms.

Suitable heteroaryls include pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, pyridone, pyrimidone, pyrazinone, pyrimidinone, and the like. The heteroaryl group is optionally substituted by 1 to 5 suitable substituents.

As used herein, the term "heterocyclic" is defined to include a monocyclic, bridged polycyclic or fused polycyclic, saturated or unsaturated, non-aromatic 3 to 14 membered ring system, 1 to 13 carbon atoms and including 1 to 5 heteroatoms selected from O, S and N. The heterocyclic group also includes one to three oxo groups. Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, 2-azabicyclo[2.2.1]heptanone, 3-azabicyclo[3.1.0]hexane, 3-azabicyclo[4.1.0]heptane and the like. Further examples of said heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, isothiazolidine, 1,3-thiazolidin-3-yl, 1,2-pyrazolidin-2-yl, 1,2-tetrahydrothiazin-2-yl, 1,3-tetrahydrothiazin-3-yl, 1,2-tetrahydrodiazin-2-yl, 1,3-tetrahydrodiazin-1-yl, 1,4-oxazin-2-yl, oxazolidinone, and the like. The heterocycloalkyl ring is optionally substituted by 1 to 5 suitable substituents. Preferred heterocyclics include 5 and 6 membered monocyclic rings or 9 and 10 membered fused bicyclic rings.

As used herein, the term "halo" or "halogen" group is defined to include fluorine, chlorine, bromine or iodine.

As noted above, the compounds of Formula I may exist in the form of pharmaceutically acceptable salts such as, e.g., acid addition salts and base addition salts of the compounds of Formula I. The phrase "pharmaceutically acceptable salt(s)", as used herein, unless otherwise indicated, includes acid addition or base salts which may be present in the compounds of Formula I.

Pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002). Methods for making pharmaceutically acceptable salts of compounds of Formula I are known to one of skill in the art.

As used herein the terms "Formula I" and "Formula I or pharmaceutically acceptable salts thereof" are defined to include all forms of the compound of Formula I, including hydrates, solvates, isomers, crystalline and non-crystalline forms, isomorphs, polymorphs, metabolites, and prodrugs thereof.

Compounds of Formula I or pharmaceutically acceptable salt thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of Formula I may exist as clathrates or other complexes. Included within the scope of the invention are complexes such as clathrates, drug-host inclusion complexes wherein, in contrast to the aforementioned solvates, the drug and host are present in stoichiometric or non-stoichiometric amounts. Also included are complexes of the Formula I containing two or more organic and/or inorganic components which may be in stoichiometric or non-stoichiometric amounts. The resulting complexes may be ionized, partially ionized, or non-ionized. For a review of such complexes, see J. K. Haleblian, *J. Pharm. Sci.* 1975, 64, 1269-1288.

Also included within the scope of the invention are metabolites of compounds of Formula I, that is, compounds formed in vivo upon administration of the drug. The metabolites of Formula I include compounds wherein $R^1$ is hydroxyalkyl.

The compounds of Formula I may have asymmetric carbon atoms. The carbon-carbon bonds of the compounds of Formula I may be depicted herein using a solid line (—), a solid wedge (▬), or a dotted wedge (▬▬). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of Formula I, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the Formula I may exhibit the phenomena of tautomerism and structural isomerism. For example, the compounds of Formula I may exist in several tautomeric forms, including the enol and imine form, and the keto and enamine form and geometric isomers and mixtures thereof. All such tautomeric forms are included within the scope of compounds of Formula I. Tautomers exist as mixtures of a tautomeric set in solution. In solid form, usually one tautomer predominates. Even though one tautomer may be described, the present invention includes all tautomers of the compounds of Formula I.

The present invention also includes isotopically-labeled compounds, which are identical to those recited in Formula I above, but for the fact that one or more atoms are replaced by an atom having an atomic mass or mass number different from the atomic mass or mass number usually found in nature. Examples of isotopes that may be incorporated into compounds of Formula I include isotopes of hydrogen, carbon, nitrogen, oxygen, phosphorus, fluorine and chlorine, such as, but not limited to, $^2H$, $^3H$, $^{13}C$, $^{14}C$, $^{15}N$, $^{17}O$, $^{18}O$, $^{32}$P, $^{35}$S, $^{18}$F, and $^{36}$Cl. Certain isotopically-labeled compounds of Formula I, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labeled compounds of Formula I may generally be prepared by carrying out the procedures disclosed in the Schemes and/or in the Examples and Preparations below, by substituting an isotopically-labeled reagent for a non-isotopically-labeled reagent.

A specific embodiment of the present invention relates to compounds of the Formula I

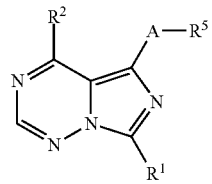

I or a pharmaceutically acceptable salt thereof wherein:
"-A-R$^5$" is:

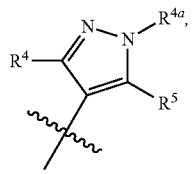

A1R$^5$

R$^1$ is —(C$_1$-C$_6$)alkyl (more specifically methyl or ethyl; even more specifically methyl);
R$^2$ is —NHR$^3$, or —N(R$^3$)$_2$;
Each R$^3$ is independently selected from the group consisting of —(C$_1$-C$_6$)alkyl-R$^9$, —(C$_2$-C$_6$)alkenyl-R$^9$, —(C$_2$-C$_6$) alkynyl-R$^9$, and —(C$_3$-C$_{15}$)cycloalkyl-R$^9$ (more specifically —(C$_1$-C$_6$)alkyl-R$^9$ and even more specifically methyl); or when R$^2$ is —N(R$^3$)$_2$ both of said R$^3$ may be taken together with the nitrogen atom to which they are attached to form a 4- to 6-membered heterocyclic ring optionally substituted with one to three substituents independently selected from the group consisting of hydrogen, fluoro, —CN, —CF$_3$, —CHF$_2$, —CH$_2$F, —OH, —O—(C$_1$-C$_6$)alkyl, NH$_2$, —NH—(C$_1$-C$_6$)alkyl, —N[(C$_1$-C$_6$)alkyl]$_2$, (C$_1$-C$_6$)alkyl, (C$_2$-C$_6$)alkenyl, (C$_2$-C$_6$)alkynyl, —(C=O)—R$^8$, —(C=O)—OR$^8$, —(C=O)—N(R$^8$)$_2$—O—(C=O)—R$^8$, —OR$^8$, —O—(C=O)—OR$^8$, —SR$^8$, —S(O)R$^8$, —S(O)$_2$R$^8$, —S(O)$_2$N(R$^8$)$_2$, —NH—(C=O)—R$^8$, —NH—(C=O)—OR$^8$, —O—(C=O)—N(R$^8$)$_2$, —NH—(C=O)—N(R$^8$)$_2$, —N[(C$_1$-C$_6$)alkyl](C=O)—R$^8$, —N[(C$_1$-C$_6$)alkyl](C=O)—OR$^8$, —N[(C$_1$-C$_6$)alkyl](C=O)—N(R$^8$)$_2$, (C$_3$-C$_{15}$)cycloalkyl, (C$_6$-C$_{10}$)aryl, (C$_1$-C$_{14}$)heterocyclic, and (C$_1$-C$_{14}$)heteroaryl; (more specifically one or two substituents wherein said substituent(s) is hydrogen, fluoro, —CF$_3$, —CHF$_2$, —CH$_2$F, —OH, —O—(C$_1$-C$_6$)alkyl, NH$_2$, —NH—(C$_1$-C$_6$)alkyl, —N[(C$_1$-C$_6$)alkyl]$_2$, (C$_1$-C$_6$)alkyl, or —NH—(C=O)—OR$^8$; even more specifically wherein said substituent(s) is hydrogen, fluoro, methoxy, or methylcarbamate);

R$^4$ is hydrogen;
R$^{4a}$ is (C$_1$-C$_6$)alkyl (more specifically methyl or ethyl; even more specifically methyl);
R$^5$ is:

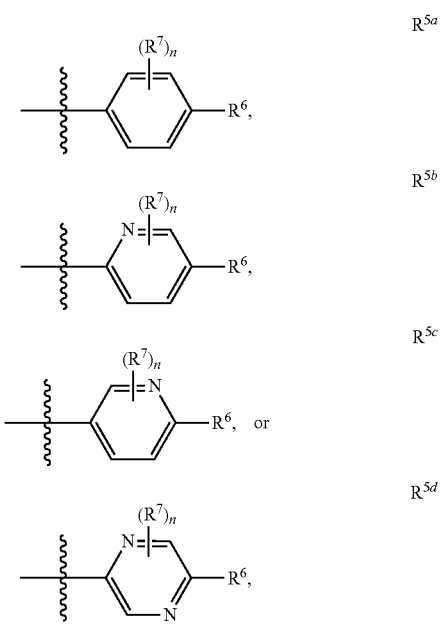

where n is 0, 1, 2, 3, or 4 (more specifically wherein n is 0, 1 or 2)(more specifically wherein R$^7$ is hydrogen, chloro, fluoro, methyl, methoxy, or cyano; and even more specifically wherein R$^6$ is chloro, bromo, methyl, ethyl, methoxy, —CF$_3$, —CF$_2$CH$_3$, —OCF$_3$, —OCHF$_2$, NO$_2$, —(C=O)—CH$_3$, (C$_3$-C$_{15}$)cycloalkyl, or isopropyl;

A specific embodiment of the present invention relates to the so called 5-(1H-pyrazol-4-yl)imidazo[1,5-f][1,2,4]triazine compounds of Formula Ia, wherein Formula I contains the group A1R$^5$:

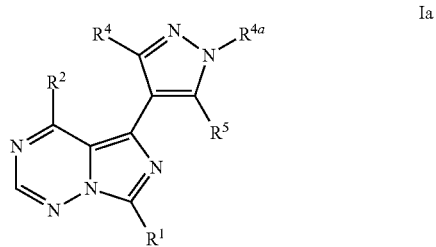

Ia

Another specific embodiment of the present invention relates to the so called 5-(1H-imidazol-5-yl)imidazo[1,5-f][1,2,4]triazine compounds of Formula Ib, wherein Formula I contains the group A2R$^5$.

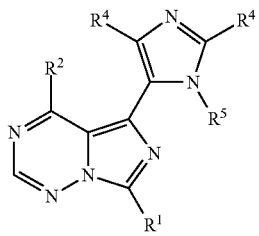

Ib

Another specific embodiment of the present invention relates to the so called 5-(1H-pyrazol-5-yl)imidazo[1,5-f][1,2,4]triazine compounds of Formula Ic, wherein Formula I contains the group A3R⁵.

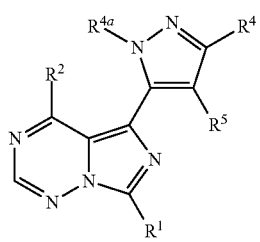

Ic

Another specific embodiment of the present invention relates to the so called 5-(5-phenyl-1H-pyrazol-4-yl)imidazo[1,5-f][1,2,4]triazine compounds of Formula Id, wherein R⁵ is depicted as optionally substituted phenyl.

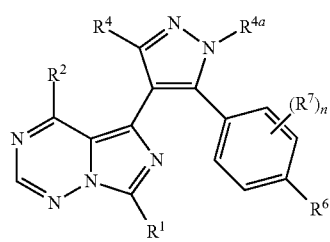

Id

Another specific embodiment of the present invention relates to the so called 5-(1-phenyl-1H-imidazol-5-yl)imidazo[1,5-f][1,2,4]triazine compounds of Formula Ie, wherein R⁵ is depicted as optionally substituted phenyl.

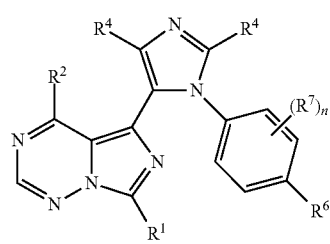

Ie

Another specific embodiment of the present invention relates to the so called 5-(4-phenyl-1H-pyrazol-5-yl)imidazo[1,5-f][1,2,4]triazine compounds of Formula If, wherein R⁵ is depicted as optionally substituted phenyl.

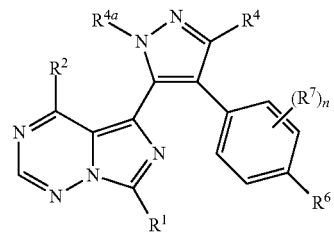

If

Another specific embodiment of the present invention relates to the so called 5-[5-(pyridin-2-yl)-1H-pyrazol-4-yl]imidazo[1,5-f][1,2,4]triazine compounds of Formula Ig, wherein R⁵ is depicted as optionally substituted pyridin-2-yl.

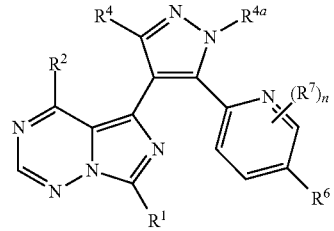

Ig

Another specific embodiment of the present invention relates to the so called 5-[1-(pyridin-2-yl)-1H-imidazol-5-yl]imidazo[1,5-f][1,2,4]triazine compounds of Formula Ih, wherein R⁵ is depicted as optionally substituted pyridin-2-yl.

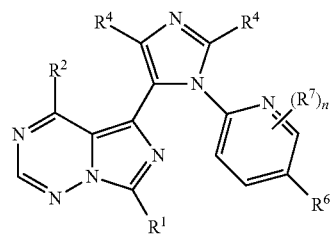

Ih

Another specific embodiment of the present invention relates to the so called 5-[4-(pyridin-2-yl)-1H-pyrazol-5-yl]imidazo[1,5-f][1,2,4]triazine compounds of Formula Ii, respectively, wherein R⁵ is depicted as optionally substituted pyridin-2-yl.

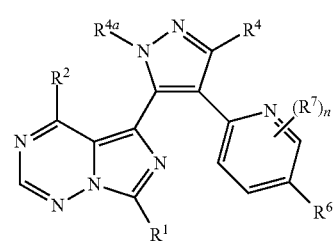

Ii

Another specific embodiment of the present invention relates to the so called 5-[5-(pyridin-3-yl)-1H-pyrazol-4-yl]imidazo[1,5-f][1,2,4]triazine compounds of Formula Ij, wherein R⁵ is depicted as optionally substituted pyridin-3-yl.

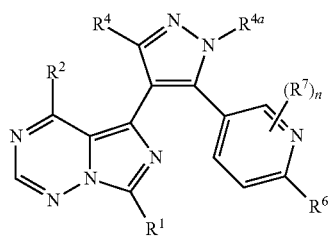

Ij

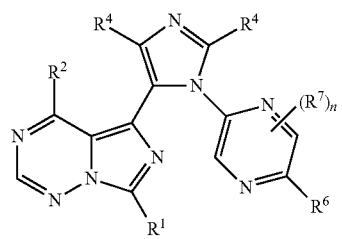

In

Another specific embodiment of the present invention relates to the so called 5-[1-(pyridin-3-yl)-1H-imidazol-5-yl]imidazo[1,5-f][1,2,4]triazine compounds of Formula Ik, wherein $R^5$ is depicted as optionally substituted pyridin-3-yl.

Another specific embodiment of the present invention relates to the so called 5-[4-(pyrazin-2-yl)-1H-pyrazol-5-yl]imidazo[1,5-f][1,2,4]triazine compounds of Formula Io, wherein $R^5$ is depicted as optionally substituted pyrazin-2-yl.

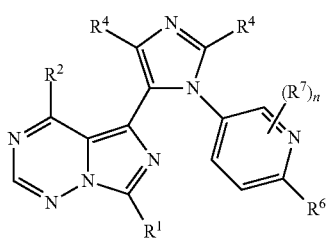

Ik

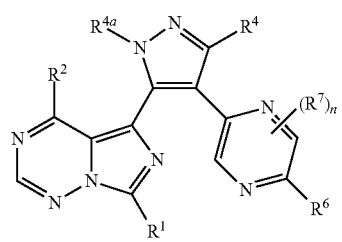

Io

Another specific embodiment of the present invention relates to the so called 5-[4-(pyridin-3-yl)-1H-pyrazol-5-yl]imidazo[1,5-f][1,2,4]triazine compounds of Formula Il, wherein $R^5$ is depicted as optionally substituted pyridin-3-yl.

Another specific embodiment of the present invention relates to the so called 5-[5-(pyrimidin-2-yl)-1H-pyrazol-4-yl]imidazo[1,5-f][1,2,4]triazine compounds of Formula Ip, wherein $R^5$ is depicted as optionally substituted pyrimidin-2-yl.

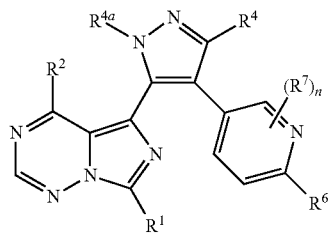

Il

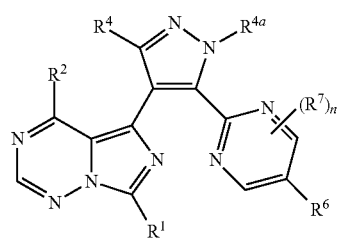

Ip

Another specific embodiment of the present invention relates to the so called 5-[5-(pyrazin-2-yl)-1H-pyrazol-4-yl]imidazo[1,5-f][1,2,4]triazine compounds of Formula Im, wherein $R^5$ is depicted as optionally substituted pyrazin-2-yl.

Another specific embodiment of the present invention relates to the so called 5-[1-(pyrimidin-2-yl)-1H-imidazol-5-yl]imidazo[1,5-f][1,2,4]triazine compounds of Formula Iq, wherein $R^5$ is depicted as optionally substituted pyrimidin-2-yl.

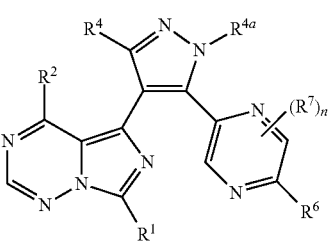

Im

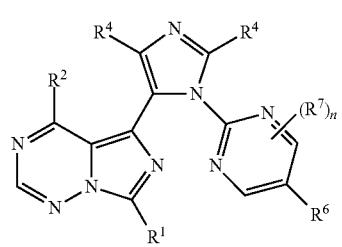

Iq

Another specific embodiment of the present invention relates to the so called 5-[1-(pyrazin-2-yl)-1H-imidazol-5-yl]imidazo[1,5-f][1,2,4]triazine compounds of Formula In, wherein $R^5$ is depicted as optionally substituted pyrazin-2-yl.

Another specific embodiment of the present invention relates to the so called 5-[4-(pyrimidin-2-yl)-1H-pyrazol-5- yl]imidazo[1,5-f][1,2,4]triazine compounds of Formula Ir, wherein $R^5$ is depicted as optionally substituted pyrimidin-2-yl.

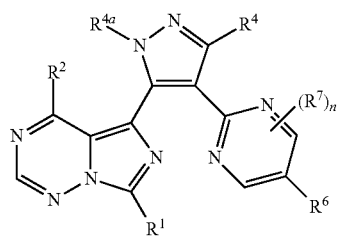

Ir

Another specific embodiment of the present invention relates to the so called 5-[5-(pyridazin-3-yl)-1H-pyrazol-4-yl]imidazo[1,5-f][1,2,4]triazine compounds of Formula Is, wherein $R^5$ is depicted as optionally substituted pyridazin-3-yl.

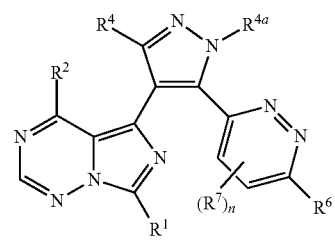

Is

Another specific embodiment of the present invention relates to the so called 5-[1-(pyridazin-3-yl)-1H-imidazol-5-yl]imidazo[5,1-f][1,2,4]triazine compounds of Formula It, wherein $R^5$ is depicted as optionally substituted pyridazin-3-yl.

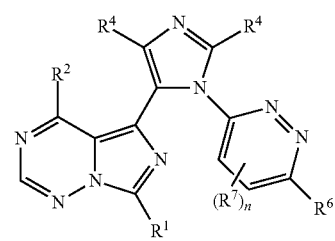

It

Another specific embodiment of the present invention relates to the so called 5-[4-(pyridazin-3-yl)-1H-pyrazol-5-yl]imidazo[5,1-f][1,2,4]triazine compounds of Formula Iu, wherein $R^5$ is depicted as optionally substituted pyridazin-3-yl.

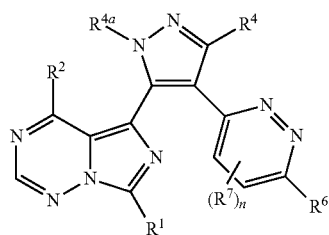

Iu

Another specific embodiment of the present invention relates to the so called 5-[5-(pyrimidin-5-yl)-1H-pyrazol-4-yl]imidazo[1,5-f][1,2,4]triazine compounds of Formula Iv, wherein $R^5$ is depicted as optionally substituted pyrimidin-5-yl.

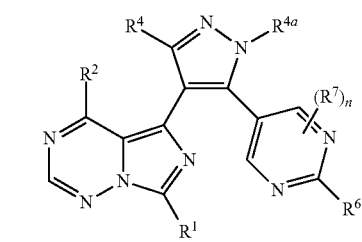

Iv

Another specific embodiment of the present invention relates to the so called 5-[1-(pyrimidin-5-yl)-1H-imidazol-5-yl]imidazo[1,5-f][1,2,4]triazine compounds Iw, wherein $R^5$ is depicted as optionally substituted pyrimidin-5-yl.

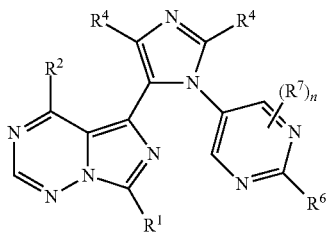

Iw

Another specific embodiment of the present invention relates to the so called 5-[4-(pyrimidin-5-yl)-1H-pyrazol-5-yl]imidazo[1,5-f][1,2,4]triazine compounds of Formula Ix, wherein $R^5$ is depicted as optionally substituted pyrimidin-5-yl.

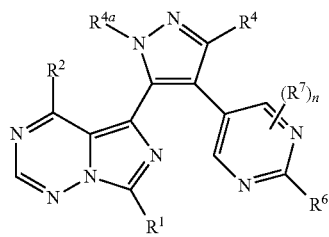

Ix

Another embodiment of particular interest relates to compounds of Formula I (and Formulae Ia-Ix) wherein $R^2$ is —(C$_1$-C$_6$)alkyl-R$^9$, —NHR$^3$, —N(R$^3$)$_2$, —O—(C$_1$-C$_6$)alkyl-R$^9$, or —OR$^8$. Specific R$^2$ groups of particular interest include —NHR$^3$ (particularly wherein R$^3$ is methyl, ethyl or propyl), and —N(R$^3$)$_2$ (particularly wherein the two R$^3$ groups are taken together with the nitrogen atom to which they are attached to form an optionally substituted azetidinyl group, particularly when optionally substituted the substituents are selected from hydrogen, fluoro, difluoro or methoxy). Other more specific R$^2$ include —(C$_1$-C$_6$)alkyl-R$^9$ and —O—(C$_1$-C$_6$)alkyl-R$^9$, particularly wherein R$^9$ is hydrogen, fluoro, —CF$_3$, —CHF$_2$, —CH$_2$F, or —CF$_2$—(C$_1$-C$_6$)alkyl, Separately, the invention also includes those compounds wherein R$^2$ is —OR$^8$, particularly wherein R$^8$ is hydrogen, —CF$_3$, —CHF$_2$, methyl or ethyl.

Another embodiment of particular interest relates to compounds of Formula I (and Formulae Ia-Ix) wherein R$^2$ is (C$_3$-C$_{15}$)cycloalkyl, (C$_6$-C$_{10}$)aryl, (C$_1$-C$_{14}$)heterocyclic, or (C$_1$-C$_{14}$)heteroaryl; wherein said (C$_3$-C$_{15}$)cycloalkyl and (C$_1$-C$_{14}$)heterocyclic may optionally contain one or two double or triple bonds and one to three oxo (O═) groups; more specifically wherein the (C$_1$-C$_{14}$)heterocyclic, or (C$_1$-C$_{14}$)heteroaryl contain one or two nitrogen atoms.

Another embodiment of particular interest relates to compounds of Formula I (and Formulae Ia-Ix) wherein R$^6$ is halo, —CF$_3$, —CHF$_2$, or —CH$_2$F; more specifically wherein R$^6$ is halo. Alternatively compounds of specific interest include the fluoromethyl substituents —CF$_3$, —CHF$_2$, or —CH$_2$F.

Another embodiment of particular interest relates to compounds of Formula I (and Formulae Ia-Ix) wherein R$^6$ is —(C═O)—R$^8$, —(C═O)—OR$^8$, —OR$^8$, —O(C═O)—N(R$^8$)$_2$, —SR$^8$, —S(O)R$^8$, —S(O)$_2$R$^8$, NH$_2$, —NH—(C$_1$-C$_6$)alkyl, —N[(C$_1$-C$_6$)alkyl]$_2$, —NH—(C═O)—R$^8$, —NH—(C═O)—OR$^8$, —O—(C═O)—N(R$^8$)$_2$, —N((C$_1$-C$_6$)alkyl)-(C═O)—R$^8$, or —N((C$_1$-C$_6$)alkyl)-(C═O)—OR$^8$; more specifically wherein R$^6$ is —(C═O)—R$^8$, —(C═O)—OR$^8$, —OR$^8$, or —O(C═O)—N(R$^8$)$_2$. Separately, the present invention contemplate the so called amino compounds NH$_2$, —NH—(C$_1$-C$_6$)alkyl, —N[(C$_1$-C$_6$)alkyl]$_2$, —NH—(C═O)—R$^8$, —NH—(C═O)—OR$^8$, —O—(C═O)—N(R$^8$)$_2$, —N((C$_1$-C$_6$)alkyl)-(C═O)—R$^8$, or —N((C$_1$-C$_6$)alkyl)-(C═O)—OR$^8$. Separately, the present invention contemplate the so called thio compounds —SR$^8$, —S(O)R$^8$, or —S(O)$_2$R$^8$.

Another embodiment of particular interest relates to compounds of Formula I (and Formulae Ia-Ix) wherein R$^6$ is (C$_1$-C$_6$)alkyl, (C$_2$-C$_6$)alkenyl, (C$_2$-C$_6$)alkynyl, (C$_3$-C$_{15}$)cycloalkyl, (C$_6$-C$_{10}$)aryl, or (C$_1$-C$_{14}$)heteroaryl; more specifically wherein R$^6$ is (C$_1$-C$_6$)alkyl, (C$_2$-C$_6$)alkenyl or (C$_2$-C$_6$)alkynyl. Separately, the present invention contemplate the ring compounds (C$_3$-C$_{15}$)cycloalkyl, (C$_1$-C$_{14}$)heterocyclic, (C$_6$-C$_{10}$)aryl, or (C$_1$-C$_{14}$)heteroaryl.

Another embodiment of interest relates to compounds of Formula I (and Formulae Ia-Ix) wherein at least one substituent includes a SF$_5$ moiety.

Each of the foregoing embodiments is intended to be interpreted as a single embodiment as well as an embodiment taken in combination with each of the previous aforesaid embodiments (e.g. each R$^6$ embodiment is taken together with R$^2$ and with Formulae Ia-Ix).

In another embodiment, the invention also relates to the compounds described as Examples 1-86 in the Examples section of the subject application, and pharmaceutically acceptable salts thereof.

In another embodiment the invention relates to a compound of Formula I wherein said compound is:
4-(azetidin-1-yl)-7-methyl-5-[1-methyl-5-(4-methylphenyl)-1H-pyrazol-4-yl]imidazo[5,1-f][1,2,4]triazine;
4-(azetidin-1-yl)-7-methyl-5-{1-methyl-5-[4-(trifluoromethyl)phenyl]-1H-pyrazol-4-yl}imidazo[5,1-f][1,2,4]triazine;
4-(azetidin-1-yl)-7-methyl-5-{1-methyl-5-[6-(trifluoromethyl)pyridin-3-yl]-1H-pyrazol-4-yl}imidazo[5,1-f][1,2,4]triazine;
4-(azetidin-1-yl)-5-[5-(4-chlorophenyl)-1-methyl-1H-pyrazol-4-yl]-7-methylimidazo[5,1-f][1,2,4]triazine;
4-(azetidin-1-yl)-5-[5-(5-chloropyridin-2-yl)-1-methyl-1H-pyrazol-4-yl]-7-methylimidazo[5,1-f][1,2,4]triazine;
5-{5-[4-(difluoromethyl)phenyl]-1-methyl-1H-pyrazol-4-yl}-N,7-dimethylimidazo[5,1-f][1,2,4]triazin-4-amine;
7-methyl-N-(d$_3$)methyl-5-{1-methyl-5-[4-(trifluoromethyl)phenyl]-1H-pyrazol-4-yl}imidazo[5,1-f][1,2,4]triazin-4-amine;
N,7-dimethyl-5-{1-methyl-5-[5-(trifluoromethyl)pyridin-2-yl]-1H-pyrazol-4-yl}imidazo[5,1-f][1,2,4]triazin-4-amine;
4-(azetidin-1-yl)-5-{5-[3-fluoro-5-(trifluoromethyl)pyridin-2-yl]-1-methyl-1H-pyrazol-4-yl}-7-methylimidazo[5,1-t][1,2,4]triazine;
N,7-dimethyl-5-{1-methyl-5-[6-(trifluoromethyl)pyridin-3-yl]-1H-pyrazol-4-yl}imidazo[5,1-f][1,2,4]triazin-4-amine;
4-(azetidin-1-yl)-5-{5-[2-fluoro-6-(trifluoromethyl)pyridin-3-yl]-1-methyl-1H-pyrazol-4-yl}-7-methylimidazo[5,1-t][1,2,4]triazine;
N,7-dimethyl-5-{1-methyl-5-[4-(trifluoromethoxy)phenyl]-1H-pyrazol-4-yl}imidazo[5,1-f][1,2,4]triazin-4-amine;
4-(azetidin-1-yl)-5-{5-[4-(difluoromethyl)phenyl]-1-methyl-1H-pyrazol-4-yl}-7-methylimidazo[5,1-f][1,2,4]triazine;
4-(3-fluoroazetidin-1-yl)-7-methyl-5-{1-methyl-5-[4-(trifluoromethyl)phenyl]-1H-pyrazol-4-yl}imidazo[5,1-f][1,2,4]triazine;
4-(azetidin-1-yl)-5-[5-(4-bromophenyl)-1-methyl-1H-pyrazol-4-yl]-7-methylimidazo[5,1-f][1,2,4]triazine;
4-(azetidin-1-yl)-5-{5-[4-(difluoromethoxy)phenyl]-1-methyl-1H-pyrazol-4-yl}-7-methylimidazo[5,1-f][1,2,4]triazine;
4-azetidin-1-yl-7-methyl-5-{1-methyl-5-[5-(trifluoromethyl)pyrazin-2-yl]-1H-pyrazol-4-yl}imidazo[5,1-f][1,2,4]triazine;
4-azetidin-1-yl-5-[5-(5-bromopyridin-2-yl)-1-methyl-1H-pyrazol-4-yl]-7-methylimidazo[5,1-f][1,2,4]triazine; or
N,7-dimethyl-5-{1-methyl-5-[5-(trifluoromethyl)pyrazin-2-yl]-1H-pyrazol-4-yl}imidazo[5,1-f][1,2,4]triazin-4-amine or the pharmaceutically acceptable salts thereof.

In another embodiment the invention relates to compounds of Formula I yet to be prepared selected from the group
5-(5-(3-fluoro-5-(trifluoromethyl)pyridin-2-yl)-1-methyl-1H-pyrazol-4-yl)-N,7-dimethylimidazo[5,1-f][1,2,4]triazin-4-amine;
4-(azetidin-1-yl)-7-methyl-5-(1-methyl-5-(3-methyl-5-(trifluoromethyl)pyrazin-2-yl)-1H-pyrazol-4-yl)imidazo[5,1-f][1,2,4]triazine;
4-(azetidin-1-yl)-7-methyl-5-(1-methyl-5-(3-methyl-5-(trifluoromethyl)pyridin-2-yl)-1H-pyrazol-4-yl)imidazo[5,1-f][1,2,4]triazine;
N,7-dimethyl-5-(1-methyl-5-(3-methyl-5-(trifluoromethyl)pyrazin-2-yl)-1H-pyrazol-4-yl)imidazo[5,1-f][1,2,4]triazin-4-amine;
5-(5-(3-chloro-5-(trifluoromethyl)pyridin-2-yl)-1-methyl-1H-pyrazol-4-yl)-N, 7-dimethylimidazo[5,1-f][1,2,4]triazin-4-amine;
5-(5-(5-bromo-3-fluoropyridin-2-yl)-1-methyl-1H-pyrazol-4-yl)-N,7-dimethylimidazo[5,1-f][1,2,4]triazin-4-amine;

4-(azetidin-1-yl)-5-(5-(3-chloro-5-(trifluoromethyl)pyridin-2-yl)-1-methyl-1H-pyrazol-4-yl)-7-methylimidazo[5,1-f][1,2,4]triazine;
N,7-dimethyl-5-(1-methyl-5-(3-methyl-5-(trifluoromethyl)pyridin-2-yl)-1H-pyrazol-4-yl)imidazo[5,1-f][1,2,4]triazin-4-amine;
5-(5-(5-bromo-3-chloropyridin-2-yl)-1-methyl-1H-pyrazol-4-yl)-N,7-dimethylimidazo[5,1-f][1,2,4]triazin-4-amine;
5-(5-(5-bromo-3-methylpyridin-2-yl)-1-methyl-1H-pyrazol-4-yl)-N,7-dimethylimidazo[5,1-f][1,2,4]triazin-4-amine;
5-(1,3-dimethyl-5-(5-(trifluoromethyl)pyridin-2-yl)-1H-pyrazol-4-yl)-N,7-dimethylimidazo[5,1-f][1,2,4]triazin-4-amine;
4-(azetidin-1-yl)-5-(1,3-dimethyl-5-(5-(trifluoromethyl)pyridin-2-yl)-1H-pyrazol-4-yl)-7-methylimidazo[1,5-f][1,2,4]triazine;
4-(azetidin-1-yl)-5-(1,3-dimethyl-5-(5-(trifluoromethyl)pyrazin-2-yl)-1H-pyrazol-4-yl)-7-methylimidazo[1,5-f][1,2,4]triazine;
3-(1-methyl-4-(7-methyl-4-(2,2,2-trifluoroethyl)imidazo[5,1-f][1,2,4]triazin-5-yl)-1H-pyrazol-5-yl)aniline;
5-(5-(4-chlorophenyl)-1-methyl-1H-pyrazol-4-yl)-7-methyl-4-phenylimidazo[5,1-f][1,2,4]triazine;
7-cyclopropyl-5-(5-(4-methoxyphenyl)-1-methyl-1H-pyrazol-4-yl)imidazo[5,1-f][1,2,4]triazin-4-yl acetate;
4-(4-(4-methoxy-7-methylimidazo[5,1-f][1,2,4]triazin-5-yl)-1-methyl-1H-pyrazol-5-yl)benzonitrile;
7-methyl-5-(1-methyl-5-(4-(methylsulfonyl)phenyl)-1H-pyrazol-4-yl)imidazo[5,1-f][1,2,4]triazin-4-yl hydrogen carbonate;
methyl 4-(1-methyl-4-(7-methyl-4-(2-methylcyclopentyl)imidazo[5,1-f][1,2,4]triazin-5-yl)-1H-pyrazol-5-yl)benzoate;
4-(4-(4-(cyclopenta-1,3-dien-1-yl)-7-methylimidazo[5,1-f][1,2,4]triazin-5-yl)-1-methyl-1H-pyrazol-5-yl)-N-methylaniline;
5-(5-(3-fluoro-4-(trifluoromethyl)phenyl)-1-methyl-1H-pyrazol-4-yl)-7-methyl-4-(pyrrolidin-3-yl)imidazo[5,1-f][1,2,4]triazine;
5-(5-(4-methoxy-3-methylphenyl)-1-methyl-1H-pyrazol-4-yl)-7-methyl-4-(1-methyl-1H-pyrazol-5-yl)imidazo[5,1-f][1,2,4]triazine;
2-methyl-4-(2-methyl-5-(4-(pyrrolidin-1-yl)-7-(trifluoromethyl)imidazo[5,1-f][1,2,4]triazin-5-yl)-1H-imidazol-1-yl)phenyl acetate;
4-(5-(4-(azetidin-1-yl)-7-methylimidazo[5,1-f][1,2,4]triazin-5-yl)-3-methyl-1H-pyrazol-4-yl)benzonitrile;
4-(azetidin-1-yl)-5-(4-(5-(difluoromethyl)pyridin-2-yl)-3-methyl-1H-pyrazol-5-yl)-7-methylimidazo[5,1-f][1,2,4]triazine;
1-(5-(5-(4-(azetidin-1-yl)-7-methylimidazo[5,1-f][1,2,4]triazin-5-yl)-3-methyl-1H-pyrazol-4-yl)pyridin-2-yl)ethanone;
4-(azetidin-1-yl)-5-(4-(5-ethylpyrazin-2-yl)-3-methyl-1H-pyrazol-5-yl)-7-methylimidazo[5,1-f][1,2,4]triazine;
4-(azetidin-1-yl)-5-(4-(5-chloropyrimidin-2-yl)-3-methyl-1H-pyrazol-5-yl)-7-methylimidazo[5,1-f][1,2,4]triazine;
4-(azetidin-1-yl)-5-(4-(5,6-dimethylpyridazin-3-yl)-3-methyl-1H-pyrazol-5-yl)-7-methylimidazo[5,1-f][1,2,4]triazine;
4-(azetidin-1-yl)-5-(4-(2,4-bis(trifluoromethyl)pyrimidin-5-yl)-3-methyl-1H-pyrazol-5-yl)-7-methylimidazo[5,1-f][1,2,4]triazine;
4-(azetidin-1-yl)-5-(1-(4-fluoro-2-methylpyrimidin-5-yl)-2-methyl-1H-imidazol-5-yl)-7-methylimidazo[5,1-f][1,2,4]triazine;
or the pharmaceutically acceptable salts thereof.

The present invention also relates to compositions comprising a compound of Formula I or an acceptable salt thereof (e.g., pharmaceutical compositions). Accordingly, in one embodiment, the invention relates to a pharmaceutical composition comprising a compound of Formula I, optionally including a pharmaceutically acceptable carrier and, optionally, at least one additional medicinal or pharmaceutical agent. In one embodiment, the additional medicinal or pharmaceutical agent is an anti-schizophrenia agent as described below.

The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages. One of ordinary skill in the art would appreciate that the composition may be formulated in sub-therapeutic dosage such that multiple doses are envisioned.

In one preferred embodiment the composition comprises a therapeutically effective amount of a compound of Formula I and optionally including a pharmaceutically acceptable carrier.

Another embodiment of the invention includes a method for the treating of schizophrenia or psychosis in a mammal, preferably a human, comprising administering to said mammal (preferably a human) a therapeutically effective amount of a compound of Formula I or pharmaceutically acceptable salt thereof.

Another embodiment of the invention includes a method for treating a PDE2 mediated disorder, comprising administering to a mammal (preferably a human) in need thereof an amount of a compound of Formula I effective in inhibiting PDE2; more preferably, administering an amount of a compound of Formula I effective in selectively inhibiting PDE2.

Another embodiment of the invention provides a method for treating neurological disorders (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV associated dementia, Alzheimer's associated dementia, Huntington's associated dementia, Lewy body dementia, vascular dementia, drug related dementia, delirium, and mild cognitive impairment); mental deficiency (including Down syndrome and fragile X syndrome); sleep disorders (including hypersomnia, circadian rhythm sleep disorder, insomnia, parasomnia, and sleep deprivation) and psychiatric disorders (such as anxiety (including acute stress disorder, generalized anxiety disorder, social anxiety disorder, panic disorder, post-traumatic stress disorder and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, and postpartum depression); psychomotor disorders; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, and pagophagia); and pediatric psychiatric disorders (including attention deficit disorder, attention deficit/hyperactive disorder, conduct disorder, and autism) in a mammal, preferably a human, comprising administering to said mammal a therapeutically effective amount of a compound of Formula I or pharmaceutically acceptable salt thereof.

Another embodiment of the invention includes a method for the treatment of schizophrenia.

Another embodiment of the invention includes a method for the treatment of cognitive impairment associated with schizophrenia.

The term "therapeutically effective amount" as used herein refers to that amount of the compound being administered which will relieve to some extent one or more of the symptoms of the disorder being treated. In reference to the treatment of schizophrenia, a therapeutically effective amount refers to that amount which has the effect of relieving to some extent (or, preferably, eliminating) one or more symptoms associated with schizophrenia.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

Administration of the compounds of Formula I may be effected by any method that enables delivery of the compounds to the site of action. These methods include oral routes, intranasal routes, inhaled routes, intraduodenal routes, parenteral injection (including intravenous, subcutaneous, intramuscular, intravascular or infusion), topical, and rectal administration.

In one embodiment of the present invention, the compounds of Formula I may be preferably effected by oral routes.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals. In one embodiment of the present invention, the compounds of Formula I may preferably be used to treat humans.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent is well-known in the relevant art and would be understood to be encompassed by the skilled artisan once provided the teachings disclosed herein.

The amount of the compound of Formula I administered will be dependent on the subject being treated, the severity of the disorder or condition, the rate of administration, the disposition of the compound and the discretion of the prescribing physician. However, an effective dosage is in the range of about 0.01 to about 50 mg per kg body weight per day, preferably about 0.01 to about 5 mg/kg/day, in single or divided doses. For a 70 kg human, this would amount to about 0.7 mg to about 3500 mg/day, preferably about 5 mg to about 2000 mg/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of a compound of Formula I together with an at least one additional pharmaceutical or medicinal agent (e.g., an anti-schizophrenia agent), either sequentially or simultaneously.

As noted above, the compounds of Formula I may be used in combination with one or more additional anti-schizophrenia agents which are described below. When a combination therapy is used, the one or more additional anti-schizophrenia agents may be administered sequentially or simultaneously with the compound of the invention. In one embodiment, the additional anti-schizophrenia agent is administered to a mammal (e.g., a human) prior to administration of the compound of the invention. In another embodiment, the additional anti-schizophrenia agent is administered to the mammal after administration of the compound of the invention. In another embodiment, the additional anti-schizophrenia agent is administered to the mammal (e.g., a human) simultaneously with the administration of the compound of the invention.

The invention also relates to a pharmaceutical composition for the treatment of schizophrenia in a mammal, including a human, which comprises an amount of a compound of Formula I, as defined above (including hydrates, solvates and polymorphs of said compound or pharmaceutically acceptable salts thereof), in combination with one or more (preferably one to three) anti-schizophrenia agents such as ziprasidone, risperdone, olanzapine, quetiapine, aripiprazole, asenapine, blonanserin, or Iloperidone, wherein the amounts of the active agent and the combination when taken as a whole are therapeutically effective for treating schizophrenia.

DETAILED DESCRIPTION OF THE INVENTION

Compounds of the Formula I may be prepared according to the following reaction schemes and accompanying discussion. Unless otherwise indicated, $R^1$ through $R^8$, A, and n, and structural Formula I are as defined above in the reaction schemes and discussion that follow. In general the compounds of this invention can be made by processes which include processes analogous to those known in the chemical arts, particularly in light of the description contained herein. Certain processes for the manufacture of the compounds of this invention are provided as further features of the invention and are illustrated by the following reaction schemes. Other processes may be described in the experimental section.

Scheme 1

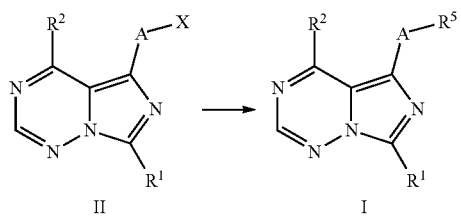

Scheme 2

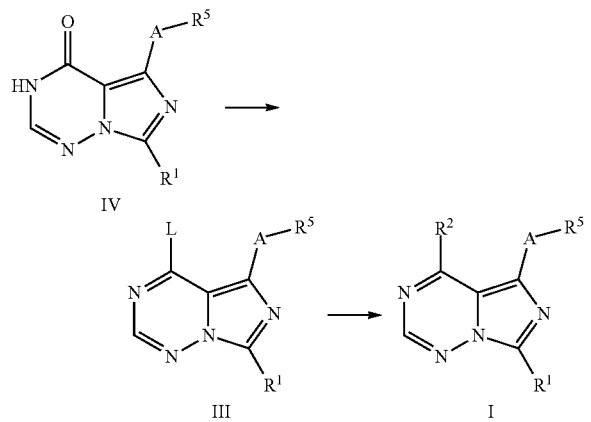

Scheme 3

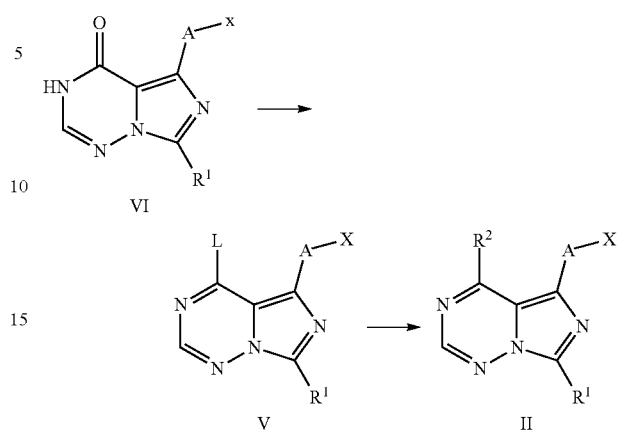

Scheme 4

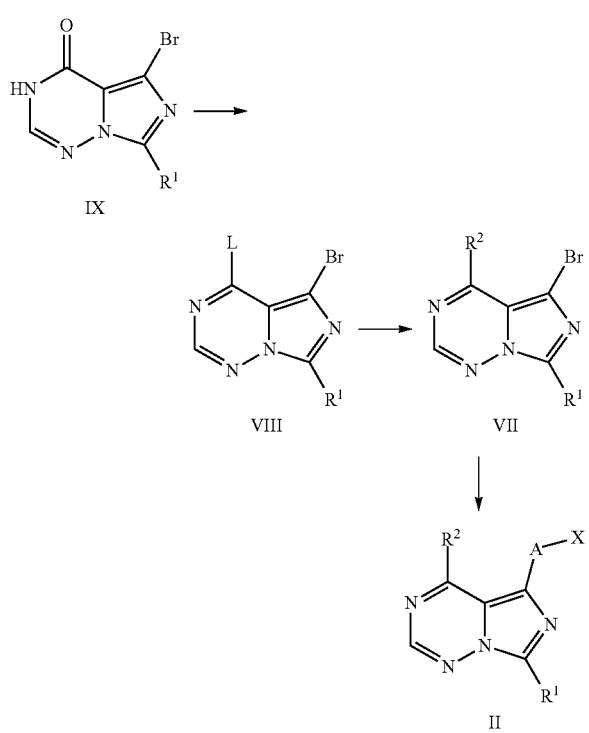

Scheme 5

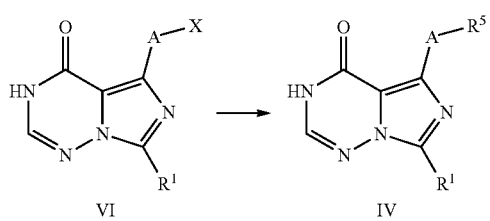

Scheme 1 refers to the preparation of compounds of Formula I. Referring to Scheme 1, compounds of Formula I wherein $R^5$ is bonded to a carbon atom in group A are prepared from compounds of Formula II wherein "A-X" is
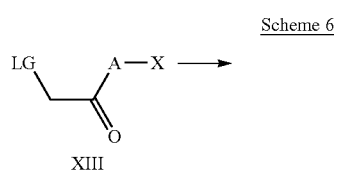
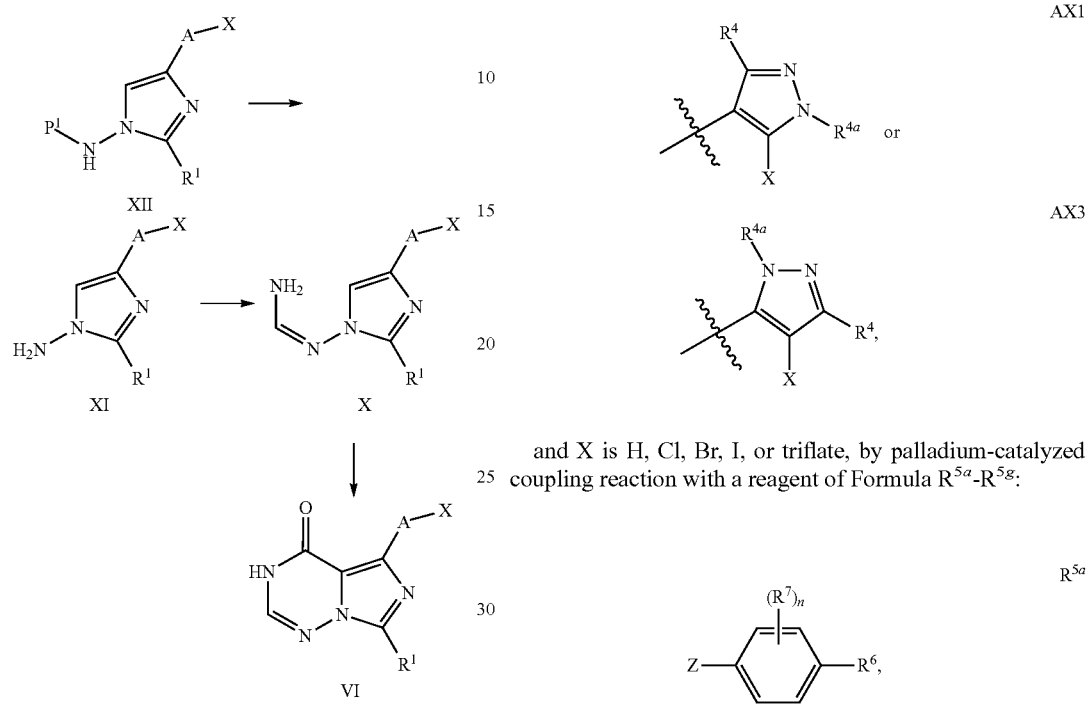
and X is H, Cl, Br, I, or triflate, by palladium-catalyzed coupling reaction with a reagent of Formula $R^{5a}$-$R^{5g}$:
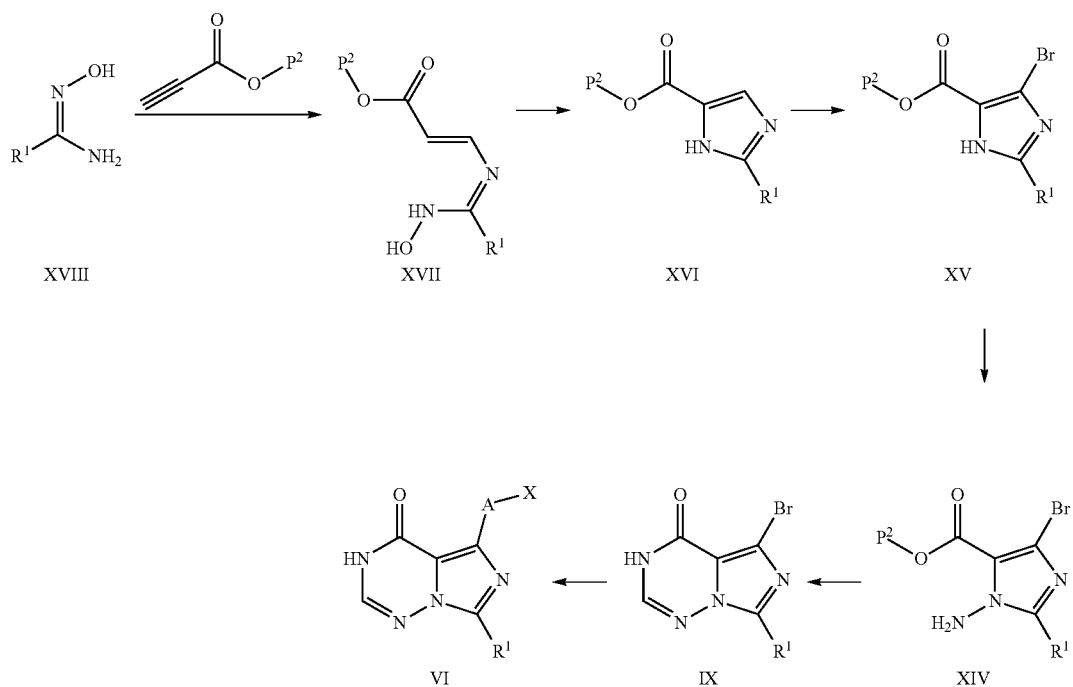

-continued

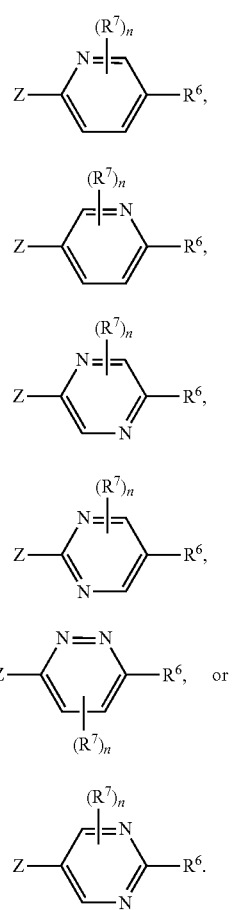

Depending on the type of reaction employed, Z may represent Br, B(OH)$_2$ or B(OR)$_2$, or a trialkyltin moiety. For example, when X is halogen or triflate and the R$^5$ reagent is a boronic acid or boronic ester, a Suzuki reaction may be used [A. Suzuki, *J. Organomet. Chem.* 1999, 576, 147-168; N. Miyaura and A. Suzuki, *Chem. Rev.* 1995, 95, 2457-2483; A. F. Littke et al., *J. Am. Chem. Soc.* 2000, 122, 4020-4028]. More specifically, the heteroaromatic iodide, bromide or triflate of Formula II is combined with 1 to 3 equivalents of aryl or heteroaryl boronic acid or boronic ester and a suitable base, such as 2 to 5 equivalents of sodium carbonate, in a suitable organic solvent such as ethanol. A palladium catalyst is added, such as 0.01 equivalents of tetrakis(triphenylphosphine)palladium(0), and the reaction mixture is heated to temperatures ranging from 60 to 100° C. for 1 to 24 hours. In some cases, it may be advantageous to employ 1 to 2 equivalents of copper(I) chloride and 1 to 2 equivalents of potassium bromide in the Suzuki reaction, in 1,2-dimethoxyethane as solvent. Alternatively, the coupling reaction may be carried out by reaction of Formula II, wherein X is H and Z is Br, with 1 to 3 equivalents of the (R$^5$)—Br reagent, in the presence of 0.01 to 0.5 equivalents of allylpalladium chloride dimer and a suitable base, such as 2 to 4 equivalents of potassium carbonate, in a suitable organic solvent such as 1,4-dioxane. The reaction may be carried out at temperatures ranging from 100 to 160° C. for 24 to 72 hours. When X is halogen or triflate and Z is trialkyltin, a Stille coupling may be employed [V. Farina et al., *Organic Reactions* 1997, 50, 1-652]. More specifically, a compound of Formula II wherein X is bromide, iodide or triflate may be combined with 1.5 to 3 equivalents of the R$^5$ stannane in the presence of a palladium catalyst, such as 0.05 equivalents of dichlorobis(triphenylphosphine)palladium (II), in a suitable organic solvent such as toluene, and the reaction may be heated to temperatures ranging from 100 to 130° C. for 12 to 36 hours. When X is Br, I or triflate and Z is Br or I, a Negishi coupling may be used [E. Erdik, *Tetrahedron* 1992, 48, 9577-9648]. More specifically, a compound of Formula II wherein X is bromide, iodide or triflate may be transmetallated by treatment with 1 to 1.1 equivalents of an alkyllithium reagent followed by a solution of 1.2 to 1.4 equivalents of zinc chloride in an appropriate solvent such as tetrahydrofuran at a temperature ranging from −80 to −65° C. After warming to a temperature between 10 and 30° C., the reaction may be treated with the R$^5$—Z reagent, and heated at 50 to 70° C. with addition of a catalyst such as tetrakis (triphenylphosphine)palladium(0). The reaction may be carried out for times ranging from 1 to 24 hours. None of these reactions are limited to the employment of the solvent, base, or catalyst described above, as many other conditions may be used.

Alternatively, referring to Scheme 1, the polarity of the coupling reaction of AX1 or AX3 with any of R$^{5a}$-R$^{5g}$ may be reversed. In that case, the X group of AX1 or AX3 is a boronic acid, boronate, or trialkyltin moiety, and the Z group of R$^{5a}$-R$^{5g}$ is Cl, Br, I, or triflate. The chemistry employed to create the carbon-carbon bond is the same as that described above.

Referring to Scheme 1, additional compounds of Formula I, wherein R$^5$ is bonded to a nitrogen atom in group A, are prepared from compounds of Formula II wherein "A-X" is

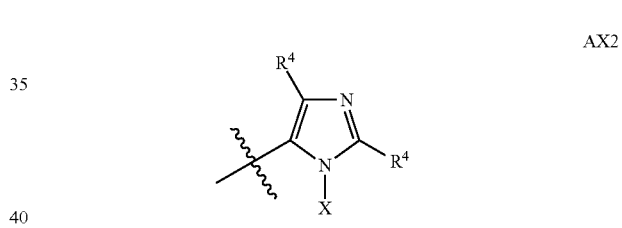

and X is H, by copper-catalyzed coupling with a reagent of Formula R$^{5a}$ through R$^{5g}$ wherein Z is a boronic acid group or Z is Cl or Br, according to the method of P. Y. S. Lam et al., *Tetrahedron Lett.* 1998, 39, 2941-2944 or the method of Z. Xi et al., *Tetrahedron* 2008, 64, 4254-4259.

Scheme 2 refers to an alternate preparation of compounds of Formula I. Referring to Scheme 2, a compound of Formula I, wherein R$^2$ is N(R$^3$)$_2$ or HNR$^3$, can be prepared from a compound of Formula III, wherein L is a triazole or chloro, by reaction with 1.1 to 4 equivalents of a primary or secondary amine, H$_2$NR$^3$ or HN(R$^3$)$_2$, optionally in the presence of a base such as cesium carbonate, in an appropriate organic solvent such as dichloromethane or N,N-dimethylformamide. Suitable temperatures for the aforesaid reaction are between 0° C. and 100° C. Suitable reaction times are from 20 minutes to 48 hours. Alternatively, a compound of Formula I, wherein R$^2$ is aryl or heteroaryl, can be prepared from a compound of Formula III, by reaction with the appropriate aryl or heteroaryl iodide, bromide, trialkyltin derivative, zinc derivative, boronic acid or boronic ester, as described for conversion of Formula II to Formula I in Scheme 1, to generate compounds of Formula I. Alternatively, a compound of Formula I, wherein R$^2$ is alkyl, can be prepared from a compound of Formula III, wherein L is chloro, by reaction with an appropriate zinc reagent in a Negishi reaction, as described above for conversion of Formula II to Formula I in Scheme 1.

(See also R. T. Hendricks et al., *Bioorg. Med. Chem. Lett.* 2009, 19, 410-414.) Alternatively a compound of Formula I, wherein $R^2$ is alkyl, cycloalkyl, or heterocyclic, can be prepared from a compound of Formula III, wherein L is chloro, by reaction with the appropriate Grignard reagent in the presence of iron(III) acetylacetonate, as described by L. K. Ottesen et al., *Organic Lett.* 2006, 8, 1771-1773.

Referring to Scheme 2, a compound of Formula I wherein $R^2$ is —O—($C_1$-$C_6$)alkyl-$R^9$ or —$OR^8$ may be directly prepared from a compound of Formula IV via an alkylation with the corresponding halide, or via a Mitsunobu reaction with the requisite alcohol. See S. B. Bodendiek et al., *Eur. J. Med. Chem.* 2009, 44, 1838-1852; A. F. Khattabi et al., *Synth. Commun.* 2006, 36, 2751-2761; G. Smith et al., *J. Med. Chem.* 2008, 51, 8057-8067.

Compounds of Formula III wherein L is chloro or 1H-1,2, 4-triazol-1-yl may be prepared from a compound of Formula IV by treatment with phosphorus oxychloride, optionally in the presence of 1H-1,2,4-triazole. More specifically, 2 to 4 equivalents of phosphorus oxychloride and 8 to 11 equivalents of 1H-1,2,4-triazole, in an appropriate organic solvent such as acetonitrile or dichloromethane, at a temperature between −10 and 5° C., are treated with 12 to 15 equivalents of triethylamine or N,N-diisopropylethylamine. After addition of 1 equivalent of the imidazotriazinone of Formula IV, the reaction mixture may be maintained at temperatures ranging from 25° C. to reflux for 2 to 24 hours, providing a compound of Formula III wherein L is 1H-1,2,4-triazole. If the 1H-1,2,4-triazole is omitted from the reaction, which in this case may be carried out in toluene as solvent, the product is a compound of Formula III wherein L is chloro. It is not necessary in all cases to isolate the intermediate of Formula III, which may be directly reacted with the appropriate amine reagent. Compounds of Formula III wherein L is triflate may be prepared from a compound of Formula IV by standard methods; see B. T. Shireman et al, *Bioorg. Med. Chem. Lett.* 2008, 18, 2103-2108. These reactions are not limited to the employment of the solvent or base described above, as many other conditions may be used.

Scheme 3 refers to the preparation of compounds of Formula II, wherein $R^2$ is $HNR^3$ or $N(R^3)_2$. Compounds of Formula II may be converted into compounds of Formula I according to the methods of Scheme 1. Referring to Scheme 3, a compound of Formula II may be prepared from a compound of Formula V by methods analogous to those of the conversion of Formula III to Formula I in Scheme 2. Compounds of Formula V, wherein L is chloro or 1H-1,2,4-triazol-1-yl, may be prepared from compounds of Formula VI, wherein X is H, Cl, Br or I, by methods analogous to the conversion of compounds of Formula IV to III in Scheme 2.

Scheme 4 refers to an alternate preparation of compounds of Formula II, wherein $R^2$ is $HNR^3$ or $N(R^3)_2$ and X is H or Cl. Compounds of Formula II may be converted into compounds of Formula I according to the methods of Scheme 1. Referring to Scheme 4, compounds of Formula II may be prepared from a bromo compound of Formula VII by palladium-catalyzed coupling with an appropriately substituted heteroaromatic compound of Formula ZAX:

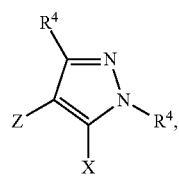

ZAX1

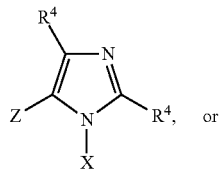

ZAX2

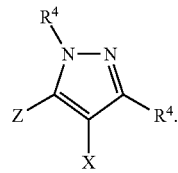

ZAX3

A compound of Formula II, X is H in compounds ZAX1 and ZAX3; in ZAX2, X may be H or an appropriate protecting group for nitrogen well-known to those skilled in the art, such as Boc, p-methoxybenzyl, allyl or 2-(trimethylsilyl)ethoxy]methyl. When Z is $B(OH)_2$ or $B(OR)_2$, the carbon-carbon bond coupling may be carried out under conditions described above for the Suzuki reaction. One of skill in the art would recognize that this chemistry will also be effective if X is $R^5$; in this case, the product will be a compound of Formula I. A compound of Formula VII wherein $R^2$ is $HNR^3$ or $N(R^3)_2$ may be prepared from a compound of Formula VIII by methods analogous to the conversion of compounds of Formula III to Formula I in Scheme 2. A compound of Formula VIII may be prepared from a compound of Formula IX by methods analogous to the conversion of compounds of Formula IV to Formula III in Scheme 2.

Scheme 5 refers to the preparation of compounds of the Formula IV. Compounds of Formula IV may be converted into compounds of Formula I according to the methods of Scheme 2. Referring to Scheme 5, a compound of Formula IV may be prepared from a compound of Formula VI, wherein X is H, Cl, Br, I, triflate, boronic acid, boronate or trialkyltin in the same manner as described for conversion of a compound of Formula II to a compound of Formula I in Scheme 1.

Scheme 6 refers to the preparation of compounds of Formula VI, wherein "A-X" is

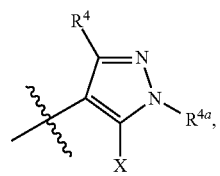

AX1

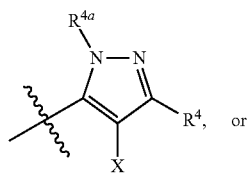

AX3

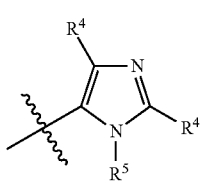

AX4 and X is H, Cl, Br, I, triflate, boronic acid, boronate or trialkyltin. A compound of Formula VI may be converted to a compound of Formula I using the methods described in Scheme 3 followed by Scheme 1, or Scheme 5 followed by Scheme 2. Referring to Scheme 6, a compound of Formula VI may be generated from a compound of Formula X, by the action of 1.1 to 3 equivalents of 1,1'-carbonyldiimidazole or 1,1'-carbonyldi(1,2,4-triazole) in a solvent such as 1,4-dioxane or tetrahydrofuran, at temperatures ranging from 40 to 70° C. for 1 to 4 hours.

A compound of Formula X may be prepared from a compound Formula XI by treatment with 2 to 5 equivalents of formamidine acetate in a solvent such as 2-butanol, at temperatures ranging from 60 to 100° C. for 1 to 12 hours. A compound of Formula XI may be prepared from a compound of Formula XII by removal of the protecting group $P^1$, wherein $P^1$ may be —(C═O)-aryl, —(C═O)-alkyl, —(C═O)O—($C_1$-$C_4$)alkyl or another appropriate protecting group known to one skilled in the art, via basic hydrolysis of the amide or carbamate group or, in the case wherein $P^1$ is —(C═O)O-tert-butyl, reaction with an excess of trifluoroacetic acid in dichloromethane solvent, at a temperature ranging from 15 to 35° C. A compound of Formula XII may be prepared from a compound of Formula XIII, wherein X is H, Cl, Br, I, triflate, boronic acid, boronate or trialkyltin and wherein LG is Cl, Br or I, by reaction with 1.1 to 2 equivalents of an N-protected $R^1$-imidohydrazide compound of Formula

XIX

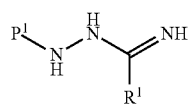

wherein $P^1$ is —(C═O)-aryl, —(C═O)-alkyl, —(C═O)O—($C_1$-$C_4$)alkyl or another appropriate protecting group known to one skilled in the art. This reaction may be carried out in a solvent such as 2-methyltetrahydrofuran and/or 1,2-dimethoxyethane at temperatures ranging from 60 to 90° C., in the presence of a base such as 2 to 4 equivalents of N,N-diisopropylethylamine. The imidohydrazide reagent XIX may be prepared via reaction of the requisite acyl hydrazine with the appropriate iminoether, according to the method of D. Hurtaud et al., *Synthesis* 2001, 2435-2440.

Scheme 7 refers to the preparation of compounds of Formula VI, wherein X is H or Cl. Compounds of Formula VI may be converted to compounds of Formula I according to the methods described in Scheme 3 followed by Scheme 1, or Scheme 5 followed by Scheme 2. A compound of Formula IX may be used to prepare compounds of Formula I as described in Scheme 4 followed by Scheme 1. Referring to Scheme 7, a compound of Formula VI may be synthesized from a compound of Formula IX by palladium-catalyzed reaction with an appropriately substituted heteroaromatic compound of Formula ZAX

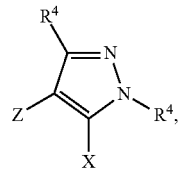

ZAX1

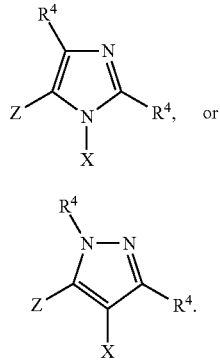

ZAX2

ZAX3

In this case, X is H or Cl in compounds ZAX1 and ZAX3; in ZAX2, X may be H or an appropriate protecting group for nitrogen well-known to those skilled in the art, such as BOC, p-methoxybenzyl, allyl or 2-(trimethylsilyl)ethoxy]methyl; Z is $B(OH)_2$ or $B(OR)_2$. The carbon-carbon coupling reaction may be carried out in similar fashion to that described for conversion of compound VII to a compound of Formula II in Scheme 4.

A compound of Formula IX may be prepared by reaction of a compound of Formula XIV, wherein $P^2$ is ($C_1$-$C_4$)alkyl, with 1 to 30 equivalents of formamide, at temperatures ranging from 100 to 180° C. for 2 to 20 hours. A compound of Formula XIV may be prepared from a compound of Formula XV by deprotonation with a base such as lithium bis(trimethylsilyl)amide and subsequent amination with a reagent such as O-(4-nitrobenzoyl)hydroxylamine or O-(diphenylphosphinyl)hydroxylamine. Caution: O-(diphenylphosphinyl)hydroxylamine is a highly energetic substance that has shown the ability to explosively decompose under ambient conditions. Its use should be carefully monitored. A compound of Formula XV may be prepared by bromination of a compound of Formula XVI according to the method of T. L Grange et al., *Tetrahedron Lett.* 2007, 48, 6301-6303, using bromine in a solvent such as N,N-dimethylformamide at temperatures ranging from 60 to 90° C., under the influence of a base such as potassium bicarbonate. Compounds of Formula XVI may be generated via cyclization of a compound of Formula XVII, carried out for instance by heating in a microwave reactor at 150 to 190° C. for 30 minutes to 3 hours, in an appropriate inert solvent such as 1,4-dioxane. Compounds of Formula XVII are obtained via reaction of a propiolate ester with an N'-hydroxy imidamide of Formula XVIII, which may be carried out at reflux temperature in a solvent such as methanol or ethanol, for a period of 2 to 24 hours. Compounds of Formula XVIII are easily obtained from the corresponding nitriles, as reported by X. Yang et al., *J. Med. Chem.* 2010, 53, 1015-1022.

Compounds of Formula I that have chiral centers may exist as stereoisomers, such as racemates, enantiomers, or diastereomers. Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art. See, e.g. "Stereochemistry of Organic Compounds" by E. L. Eliel (Wiley, New York, 1994), the disclosure of which is incorporated herein by reference in its entirety. Suitable stereoselective techniques are well-known to those of ordinary skill in the art.

Where a compound of Formula I contains an alkenyl or alkenylene group, geometric cis/trans (or Z/E) isomers are possible. Cis/trans isomers may be separated by conventional techniques well known to those skilled in the art, for example, chromatography and fractional crystallization. Salts of the present invention can be prepared according to methods known to those of skill in the art.

The compounds of Formula I that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, isonicotinic acid, acetic acid, lactic acid, pantothenic acid, bitartric acid, ascorbic acid, 2,5-dihydroxybenzoic acid, fumaric acid, gluconic acid, saccharic acid, formic acid, methanesulfonic acid, ethanesulfonic acid, benzenesulfonic acid, p-toluenesulfonic acid and pamoic [i.e., 1,1'-methylene-bis-(2-hydroxy-3-naphthoate)] acids, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Those compounds of Formula I that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of Formula I. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The invention also includes isotopically labeled compounds of Formula I, wherein one or more atoms is replaced by an atom having the same atomic number, but an atomic mass or mass number different from the atomic mass or mass number usually found in nature. Isotopically labeled compounds of Formula I can generally be prepared by conventional techniques known to those skilled in the art or by processes analogous to those described herein, using an appropriate isotopically labeled reagent in place of the non-labeled reagent otherwise employed.

In the following Examples and Preparations "DMSO" means dimethyl sulfoxide, "N" means Normal, "M" means molar, "mL" means milliliter, "mmol" means millimoles, "μmol" means micromoles, "eq." means equivalent, "° C." means degrees Celsius, "Pa" means pascals, "UV" means ultraviolet, "MHz" means megahertz.

EXPERIMENTAL PROCEDURES

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary

Example 1

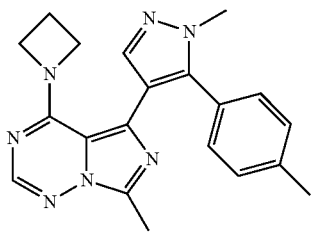 [SMILES: Cc1ccc(-c2c(-c3nc(C)n4ncnc(N5CCC5)c34)cnn2C)cc1]

4-(Azetidin-1-yl)-7-methyl-5-[1-methyl-5-(4-methylphenyl)-1H-pyrazol-4-yl]imidazo[5,1-f][1,2,4]triazine Step 1. Synthesis of 2-bromo-1-[1-methyl-5-(4-methylphenyl)-1H-pyrazol-4-yl]ethanone A. Preparation of 1-methyl-5-(4-methylphenyl)-1H-pyrazole (1-Methyl-1H-pyrazol-5-yl)boronic acid (2.0 g, 16 mmol), 1-bromo-4-methylbenzene (1.96 mL, 15.9 mmol), sodium carbonate (5.05 g, 47.6 mmol) and dichlorobis(triphenylphosphine)palladium(II) (557 mg, 0.794 mmol) were combined in a mixture of water (20 mL) and 1,2-dimethoxyethane (100 mL), and heated at 80° C. for 18 hours. After the reaction mixture had cooled, it was filtered through Celite, and concentrated in vacuo. The residue was partitioned between water and ethyl acetate, and the aqueous layer was extracted with additional ethyl acetate. The combined organic layers were dried over magnesium sulfate, filtered and concentrated under reduced pressure. Chromatography on silica gel (Gradient: 0% to 50% ethyl acetate in heptane) provided the product as a yellow oil. Yield: 1.15 g, 6.68 mmol, 42%. LCMS m/z 173.1 (M+1). $^1$H NMR (400 MHz, CDCl$_3$) δ 2.42 (s, 3H), 3.89 (s, 3H), 6.29 (d, J=2.0 Hz, 1H), 7.30 (br AB quartet, J$_{AB}$=8 Hz, Δv$_{AB}$=18 Hz, 4H), 7.51 (d, J=1.9 Hz, 1H).

B. Preparation of 4-iodo-1-methyl-5-(4-methylphenyl)-1H-pyrazole

N-Iodosuccinimide (95%, 756 mg, 3.19 mmol) was added to a solution of 1-methyl-5-(4-methylphenyl)-1H-pyrazole (500 mg, 2.90 mmol) in acetonitrile (15 mL), and the reaction was allowed to stir for 1 hour at 85° C. Removal of solvent in vacuo provided a residue, which was chromatographed on silica gel (Gradient: 20% to 50% ethyl acetate in heptane) to provide the product as a brown oil. Yield: 630 mg, 2.11 mmol, 73%. LCMS m/z 299.2 (M+1). $^1$H NMR (400 MHz, CDCl$_3$) δ 2.44 (br s, 3H), 3.83 (s, 3H), 7.26-7.33 (m, 4H), 7.57 (s, 1H).

C. Preparation of 1-[1-methyl-5-(4-methylphenyl)-1H-pyrazol-4-yl]ethanone

Tributyl(1-ethoxyvinyl)stannane (95%, 1.39 mL, 3.88 mmol) was added to a mixture of 4-iodo-1-methyl-5-(4-methylphenyl)-1H-pyrazole (768 mg, 2.58 mmol), tetrakis(triphenylphosphine)palladium(0) (298 mg, 0.258 mmol) and lithium chloride (98%, 279 mg, 6.45 mmol) in N,N-dimethylformamide (20 mL), and the reaction was stirred at 90° C. for 18 hours. After cooling, the mixture was filtered through Celite, and concentrated in vacuo; silica gel chromatography (Gradient: 10% to 50% ethyl acetate in heptane) afforded the product as a colorless oil. Yield: 460 mg, 2.15 mmol, 83%. LCMS m/z 215.3 (M+1). $^1$H NMR (400 MHz, CDCl$_3$) δ 2.17 (s, 3H), 2.45 (br s, 3H), 3.69 (s, 3H), 7.28 (br AB quartet, J$_{AB}$=8 Hz, Δv$_{AB}$=28 Hz, 4H), 7.99 (s, 1H).

D. Synthesis of 2-bromo-1-[1-methyl-5-(4-methylphenyl)-1H-pyrazol-4-yl]ethanone

Bromine (97%, 0.104 mL, 1.97 mmol) was added to a solution of 1-[1-methyl-5-(4-methylphenyl)-1H-pyrazol-4-yl]ethanone (420 mg, 1.96 mmol) in glacial acetic acid (10 mL), and the reaction mixture was vigorously stirred for 2 hours at 80° C. After removal of solvent under reduced pressure, the residue was diluted with ethyl acetate, washed with saturated aqueous sodium bicarbonate solution, washed with saturated sodium chloride solution and dried over sodium sulfate. Filtration and concentration of the filtrate in vacuo provided a residue, which was purified via silica gel chromatography (Gradient: 10% to 30% ethyl acetate in heptane) to afford the product as a colorless oil. Yield: 353 mg, 1.20 mmol, 61%. LCMS m/z 293.1 (M+1). $^1$H NMR (400 MHz, CDCl$_3$) δ 2.46 (s, 3H), 3.71 (s, 3H), 3.97 (s, 2H), 7.31 (br AB quartet, J$_{AB}$=8 Hz, Δv$_{AB}$=23 Hz, 4H), 8.05 (s, 1H).

Step 2. Synthesis of N'-ethanimidoylacetohydrazide

A mixture of sodium hydroxide (2.59 g, 64.8 mmol) in anhydrous ethanol (300 mL) was stirred for 20 minutes at 50° C. to effect dissolution. The solution was cooled to 0° C., and ethyl ethanimidoate hydrochloride (8.0 g, 65 mmol) was gradually added; the precipitated salts were removed via filtration, and the filtrate was treated with acetohydrazide (4.80 g, 64.8 mmol) at room temperature. This mixture was heated to 80° C. for 10 minutes, then allowed to cool over 18 hours. The precipitate was collected by filtration and washed with diethyl ether to provide the product as a white solid. Yield: 4.4 g, 38 mmol, 59%. $^1$H NMR (400 MHz, DMSO-d$_6$), characteristic peaks: δ 1.78 (s, 3H), 1.95 (s, 3H).

Step 3. Synthesis of N-{2-methyl-4-[1-methyl-5-(4-methylphenyl)-1H-pyrazol-4-yl]-1H-imidazol-1-yl}acetamide N'-Ethanimidoylacetohydrazide (147 mg, 1.28 mmol) and sodium bicarbonate (99%, 181 mg, 2.13 mmol) were added to a solution of 2-bromo-1-[1-methyl-5-(4-methylphenyl)-1H-pyrazol-4-yl]ethanone (250 mg, 0.853 mmol) in acetonitrile (9 mL), and the mixture was heated at 80° C. for 3 hours. The reaction was allowed to cool to room temperature, and was then diluted with dichloromethane and filtered through Celite. The filtrate was concentrated in vacuo, and the residue was purified by silica gel chromatography (Eluant: 10% methanol in dichloromethane) to provide the product as a yellow oil. Yield: 236 mg, 0.763 mmol, 89%. LCMS m/z 310.5 (M+1). $^1$H NMR (400 MHz, CDCl$_3$), presumed to be a mixture of rotamers: δ 2.10 and 1.77 (2 s, 3H), 2.25 and 2.36 (2 s, 3H), 2.44 and 2.46 (2 s, 3H), 3.69 and 3.72 (2 s, 3H), 6.21 (s, 1H), 7.22-7.33 (4H, m, assumed; partially obscured by solvent peak), 7.96 (br s, 1H).

Step 4. Synthesis of 2-methyl-4-[1-methyl-5-(4-methylphenyl)-1H-pyrazol-4-yl]-1H-imidazol-1-amine Aqueous hydrochloric acid (1 N, 7.0 mL) was added to a solution of N-{2-methyl-4-[1-methyl-5-(4-methylphenyl)-

1H-pyrazol-4-yl]-1H-imidazol-1-yl}acetamide (236 mg, 0.763 mmol) in methanol (1.0 mL), and the mixture was heated at reflux for 30 minutes. Additional 1 N aqueous hydrochloric acid (2.0 mL) was added, and heating was continued for an additional 30 minutes. After cooling, the solution was basified with 1 N aqueous sodium hydroxide solution, and the mixture was extracted twice with ethyl acetate containing 1% methanol. The combined organic layers were washed with saturated aqueous sodium chloride solution, dried over sodium sulfate, filtered, and concentrated in vacuo to afford the product as a yellow solid. Yield: 148.5 mg, 0.5555 mmol, 73%. LCMS m/z 268.5 (M+1). $^1$H NMR (400 MHz, CDCl$_3$) δ 2.39 (s, 3H), 2.45 (br s, 3H), 3.70 (s, 3H), 4.45 (br s, 2H), 6.26 (s, 1H), 7.24-7.32 (m, 4H, assumed; partially obscured by solvent peak), 7.97 (s, 1H).

Step 5. Synthesis of N-{2-methyl-4-[1-methyl-5-(4-methylphenyl)-1H-pyrazol-4-yl]-1H-imidazol-1-yl}imidoformamide Ethyl imidoformate hydrochloride (608 mg, 5.55 mmol) was added to a solution of 2-methyl-4-[1-methyl-5-(4-methylphenyl)-1H-pyrazol-4-yl]-1H-imidazol-1-amine (148 mg, 0.554 mmol) in ethanol (5 mL), and the reaction mixture was heated at 75° C. for 66 hours. Additional ethyl imidoformate hydrochloride (300 mg, 2.74 mmol) was added, and heating was continued for 8 hours. A final charge of ethyl imidoformate hydrochloride (300 mg, 2.74 mmol) was followed by maintaining the reaction at 75° C. for an additional 18 hours. The reaction mixture was cooled, concentrated in vacuo and diluted with ethyl acetate. This organic layer was washed with saturated aqueous sodium bicarbonate solution, washed with saturated aqueous sodium chloride solution and dried over sodium sulfate. Filtration and removal of solvent under reduced pressure, followed by purification using silica gel chromatography (Eluant: 10% methanol in dichloromethane) provided the product as a yellow solid. Yield: 70 mg, 0.24 mmol, 43%. LCMS m/z 295.5 (M+1). $^1$H NMR (400 MHz, CD$_3$OD), presumed to be a mixture of rotamers or tautomers: δ 2.20 and 2.25 (2 s, 3H), 2.43 (br s, 3H), 3.68 (s, 3H), 6.14 and 6.30 (2 s, 1H), 7.26-7.30 (m, 3H), 7.35 (br d, J=8 Hz, 2H), 7.84 and 7.81 (2 s, 1H).

Step 6. Synthesis of 7-methyl-5-[1-methyl-5-(4-methylphenyl)-1H-pyrazol-4-yl]imidazo[5,1-f][1,2,4]triazin-4(3H)-one Sodium hydride (60% dispersion in mineral oil, 24 mg, 0.60 mmol) was added to a solution of N-{2-methyl-4-[1-methyl-5-(4-methylphenyl)-1H-pyrazol-4-yl]-1H-imidazol-1-yl}imidoformamide (70 mg, 0.24 mmol) in 1,4-dioxane (4.0 mL), and the mixture was heated at 75° C. for 10 minutes. The reaction was cooled, treated with 1,1'-carbonyldiimidazole (135 mg, 0.833 mmol), allowed to stir at room temperature for 30 minutes, and then heated to 100° C. for 18 hours. After the reaction cooled to room temperature, it was quenched with water and diluted with ethyl acetate. The organic layer was washed with water, then with saturated aqueous sodium chloride solution, dried over sodium sulfate, filtered, and concentrated in vacuo. Silica gel chromatography (Gradient: 0% to 10% methanol in ethyl acetate) afforded the product as a white solid. Yield: 55 mg, 0.17 mmol, 71%. LCMS m/z 321.5 (M+1). $^1$H NMR (400 MHz, DMSO-d$_6$) δ 2.34 (br s, 3H), 2.36 (s, 3H), 3.71 (s, 3H), 7.22 (br d, J=8 Hz, 2H), 7.30 (d, J=8.2 Hz, 2H), 7.79 (s, 1H), 7.95 (s, 1H).

Step 7. Synthesis of 7-methyl-5-[1-methyl-5-(4-methylphenyl)-1H-pyrazol-4-yl]-4-(1H-1,2,4-triazol-1-yl)imidazo[5,1-f][1,2,4]triazine 1H-1,2,4-Triazole (162 mg, 2.34 mmol) was pulverized, mixed with dichloromethane (4.0 mL) and cooled to 0° C. Phosphorus oxychloride (58.2 µL, 0.624 mmol) was added, followed after 1 minute by the drop-wise addition of triethylamine (0.349 mL, 2.50 mmol). After 10 minutes at 0° C., the ice bath was removed; 5 minutes later, 7-methyl-5-[1-methyl-5-(4-methylphenyl)-1H-pyrazol-4-yl]imidazo[5,1-f][1,2,4]triazin-4(3H)-one (50 mg, 0.16 mmol) was added. The reaction mixture was maintained at room temperature for 4 hours, then cooled to 0° C. and quenched with water, then treated with saturated aqueous sodium bicarbonate solution. The mixture was extracted with ethyl acetate, and the combined organic layers were washed with water, washed with saturated aqueous sodium chloride solution, dried over sodium sulfate, filtered, and concentrated in vacuo. This crude material was taken directly to the following step. LCMS m/z 372.5 (M+1). $^1$H NMR (400 MHz, DMSO-d$_6$) δ 2.27 (br s, 3H), 2.70 (s, 3H), 3.73 (s, 3H), 6.86 (br d, J=8.2 Hz, 2H), 7.06 (br d, J=8.0 Hz, 2H), 7.37 (s 1H), 8.14 (s, 1H), 8.53 (s, 1H), 8.84 (s, 1H).

Step 8. Synthesis of 4-(azetidin-1-yl)-7-methyl-5-[1-methyl-5-(4-methylphenyl)-1H-pyrazol-4-yl]imidazo[5,1-f][1,2,4]triazine Azetidine (27.0 µL, 0.400 mmol) and cesium carbonate (97%, 202 mg, 0.601 mmol) were added to a solution of 7-methyl-5-[1-methyl-5-(4-methylphenyl)-1H-pyrazol-4-yl]-4-(1H-1,2,4-triazol-1-yl)imidazo[5,14][1,2,4]triazine (material from the previous reaction, ≤0.16 mmol) in N,N-dimethylformamide (3.0 mL), and the reaction mixture was stirred for 1 hour at room temperature. The reaction was diluted with ethyl acetate, washed with water, washed with saturated aqueous sodium chloride solution, dried over sodium sulfate, filtered, and concentrated under reduced pressure. Purification using silica gel chromatography (Gradient: 0% to 5% methanol in dichloromethane), followed by azeotroping with heptane, provided the product as a white solid. Yield: 35 mg, 0.097 mmol, 61% over 2 steps. LCMS m/z 360.2 (M+1). $^1$H NMR (400 MHz, CDCl$_3$) δ 2.20-2.28 (m, 2H), 2.35 (s, 3H), 2.64 (s, 3H), 3.5-3.9 (v br m, 2H), 3.90 (s, 3H), 3.9-4.3 (v br m, 2H), 7.21 (AB quartet, J$_{AB}$=8.1 Hz, Δν$_{AB}$=32.1 Hz, 4H), 7.64 (s, 1H), 7.78 (s, 1H).

Example 2

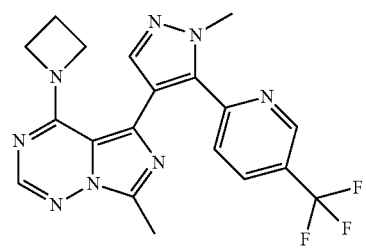 [SMILES: Cc1nc(-c2cnn(C)c2-c2ccc(C(F)(F)F)cn2)c2c(N3CCC3)ncnn12]

4-(Azetidin-1-yl)-7-methyl-5-{1-methyl-5-[5-(trifluoromethyl)pyridin-2-yl]-1H-pyrazol-4-Yl}imidazo[5,1-f][1,2,4]triazine

Step 1. Synthesis of tert-butyl 2-ethanimidoylhydrazinecarboxylate

Sodium hydroxide (16.0 g, 400 mmol) was dissolved in absolute ethanol (1000 mL) at 60° C. The solution was cooled to 0° C., and treated portion-wise with ethyl ethanimidoate hydrochloride (50 g, 400 mmol); after 10 minutes, tert-butyl hydrazinecarboxylate (52.9 g, 400 mmol) was added in a single portion. The reaction was warmed to 70° C. and was stirred at 70° C. for 2.5 hours. The mixture was then cooled to 20° C. and filtered. The filtrate was concentrated in vacuo and treated with tert-butyl methyl ether (500 mL) and ethanol (20 mL). After seeding, the mixture was allowed to stir for 18 hours, after which time the precipitated solid was collected via filtration and washed with ice-cold tert-butyl methyl ether (500 mL). The solid was dissolved in 2-methyltetrahydrofuran:methanol (9:1 mixture, 300 mL), and the solution was concentrated to dryness. The residue was washed with diethyl ether (3×200 mL) and dried, affording the product as a very pale yellow solid. Yield; 50.2 g, 290 mmol, 72%. LCMS m/z 174.3 (M+1). $^1$H NMR (500 MHz, CD$_3$OD) δ 1.47 (s, 9H), 1.88 (s, 3H).

Step 2. Synthesis of 2-bromo-1-(1-methyl-1H-pyrazol-4-yl)ethanone

A. Synthesis of 1-(1-methyl-1H-pyrazol-4-yl)ethanone

4-Bromo-1-methyl-1H-pyrazole (41.3 mL, 400 mmol), was dissolved in tetrahydrofuran (750 mL) and cooled to −78° C. N-Butyllithium (2.5 M solution in hexanes, 160 mL, 400 mmol) was added drop-wise over 30 minutes, and the resulting mixture was stirred for 1 hour at −78° C. After drop-wise addition of a solution of N-methoxy-N-methylacetamide (40.9 mL, 400 mmol) in tetrahydrofuran (100 mL) to the −78° C. reaction mixture, the cooling bath was allowed to warm to 0° C. over 4 hours. The reaction was then quenched with saturated aqueous sodium chloride solution (50 mL), and volatiles were removed in vacuo. The residue was diluted with ethyl acetate (1000 mL), treated with magnesium sulfate, and stirred for 30 minutes before being filtered and concentrated in vacuo. Purification was carried out via silica gel chromatography (material was loaded in a minimum amount of dichloromethane; Gradient: 5% to 100% ethyl acetate in heptane) to provide a pale yellow oil that solidified on standing. Yield: 28.5 g, 230 mmol, 57%. $^1$H NMR (500 MHz, CDCl$_3$) δ 2.37 (s, 3H), 3.90 (s, 3H), 7.83 (s, 1H), 7.84 (s, 1H).

B. Synthesis of 2-bromo-1-(1-methyl-1H-pyrazol-4-yl)ethanone

A solution of 1-(1-methyl-1H-pyrazol-4-yl)ethanone (28.5 g, 230 mmol) in dichloromethane (400 mL) was diluted with absolute ethanol (100 mL) and treated portion-wise with pyridinium tribromide (95%, 77.3 g, 230 mmol). The reaction was stirred at room temperature for 3 hours, during which time it solidified; the mixture was diluted with dichloromethane (300 mL) and water (400 mL), treated with sodium sulfite (5 g) and stirred for 10 minutes. The organic layer was dried over magnesium sulfate, filtered and concentrated in vacuo. The residue was washed with water (200 mL), collected by filtration, washed again with water, and dried to afford the product as an off-white solid. Yield: 41.6 g, 205 mmol, 89%. $^1$H NMR (500 MHz, CDCl$_3$) δ 7.97-7.98 (m, 1H), 7.95 (br s, 1H), 4.17 (s, 2H), 3.95-3.96 (m, 3H).

Step 3. Synthesis of tert-butyl[2-methyl-4-(1-methyl-1H-pyrazol-4-yl)-1H-imidazol-1-yl]carbamate tert-Butyl 2-ethanimidoylhydrazinecarboxylate (17.3 g, 99.9 mmol), 2-bromo-1-(1-methyl-1H-pyrazol-4-yl)ethanone (16.89 g, 83.18 mmol) and N,N-diisopropylethylamine (31.9 mL, 183 mmol) were combined in ice-cold 2-methyltetrahydrofuran (400 mL) and 1,2-dimethoxyethane (100 mL), and the reaction mixture was heated to reflux. After 2.5 hours, the reaction was cooled and washed with 50% saturated aqueous sodium chloride solution (75 mL). The aqueous layer was extracted with 2-methyltetrahydrofuran (100 mL), and the combined organic layers were dried over magnesium sulfate, filtered and concentrated in vacuo. The residue was dissolved in warm ethyl acetate (60 mL), allowed to cool to room temperature, then cooled to 5° C. for 30 minutes. The resulting solid was collected by filtration and washed with a small quantity of cold ethyl acetate, then washed with diethyl ether, to provide the product as a very pale yellow solid. Yield: 16.0 g, 57.7 mmol, 69%. LCMS m/z 278.5 (M+1). $^1$H NMR (500 MHz, CDCl$_3$) δ 1.49 (br s, 9H), 2.23 (s, 3H), 3.84 (s, 3H), 6.87 (s, 1H), 7.51 (s, 1H), 7.60 (s, 1H), 8.67 (br s, 1H).

Step 4. Synthesis of 2-methyl-4-(1-methyl-1H-pyrazol-4-yl)-1H-imidazol-1-amine, trifluoroacetate salt A solution of tert-butyl [2-methyl-4-(1-methyl-1H-pyrazol-4-yl)-1H-imidazol-1-yl]carbamate (8.0 g, 29 mmol) in methylene chloride (200 mL) and trifluoroacetic acid (40 mL) was stirred at room temperature for 2.5 hours. After removal of solvents in vacuo, the residue was stirred in 1:1 ethyl acetate/heptane for 18 hours. The resulting solid was isolated by filtration to provide the product as a white solid. Yield: 5.3 g, 18 mmol, 62%. The mother liquor was concentrated in vacuo, and the residue was stirred for 30 minutes in a 1:1:1 mixture of ethyl acetate/heptane/diethyl ether (50 mL); filtration provided additional product as a white solid. Combined yield: 7.8 g, 26.8 mmol, 92%. $^1$H NMR (400 MHz, DMSO-d$_6$) δ 2.54 (s, 3H), 3.89 (s, 3H), 6.55 (br s, 2H), 7.65 (s, 1H), 7.85 (d, J=0.7 Hz, 1H), 8.11 (br s, 1H).

Step 5. Synthesis of N-[2-methyl-4-(1-methyl-1H-pyrazol-4-yl)-1H-imidazol-1-yl]imidoformamide 2-Methyl-4-(1-methyl-1H-pyrazol-4-yl)-1H-imidazol-1-amine, trifluoroacetate salt (103.0 g, 353.7 mmol) and formamidine acetate (98%, 131 g, 1.23 mol) were combined in 2-butanol (350 mL). The reaction was heated to 100° C. for 3 hours, at which time it was allowed to cool to room temperature and diluted with a 2:1 mixture of 10 N sodium hydroxide solution/saturated aqueous sodium chloride solution (300 mL). After vigorous stirring, the layers were separated, and the aqueous layer was extracted with 2-butanol (4×250 mL). The combined organic layers were concentrated in vacuo, and the resulting solid was slurried with acetonitrile (550 mL), stirred for 2 hours at room temperature and filtered. The collected solids were washed with dry acetonitrile (3×100 mL), then dried in vacuo at 40° C. for 2 hours to provide the product as an off-white solid. Yield: 61.5 g, 301 mmol, 85%. The mother liquor was concentrated to dryness, then dissolved in acetonitrile (200 mL) and allowed to stand for 18 hours. The resulting solid was isolated by filtration to provide additional product as an off-white solid. Combined yield: 64.8 g, 317 mmol, 90%. $^1$H NMR (500 MHz, CD$_3$OD), presumed to be a mixture of rotamers or tautomers: δ 2.25 and 2.29 (2 s, 3H), 3.88 and 3.88 (2 s, 3H), 7.03 and 7.19 (2 s, 1H), 7.39 and 7.94 (2 s, 1H), 7.69 and 7.67 (2 s, 1H), 7.77 and 7.75 (2 s, 1H).

Step 6. Synthesis of 7-methyl-5-(1-methyl-1H-pyrazol-4-yl)imidazo[5,1-f][1,2,4]triazin-4(3H)-one (C1)

N-[2-Methyl-4-(1-methyl-1H-pyrazol-4-yl)-1H-imidazol-1-yl]imidoformamide (58.3 g, 285 mmol) was combined with 1,1'-carbonyldiimidazole (98%, 59.0 g, 357 mmol) in tetrahydrofuran (1140 mL) at 63° C., and the suspension was stirred for 2.5 hours at 65° C. The mixture was cooled and concentrated in vacuo; the resulting solid was slurried with methanol (400 mL), warmed to reflux for 20 minutes and cooled to 7° C. The solid was collected to provide C1 as a pale yellow solid. Yield: 45.9 g, 199 mmol, 70%. LCMS m/z 231.1 (M+1). $^1$H NMR (500 MHz, DMSO-d$_6$) δ 2.48 (s, 3H), 3.88 (s, 3H), 7.79 (s, 1H), 8.08 (s, 1H), 8.37 (s, 1H), 11.59 (br s, 1H).

Step 7. Synthesis of 4-(azetidin-1-yl)-7-methyl-5-(1-methyl-1H-pyrazol-4-yl)imidazo[5,1-f][1,2,4]triazine (C2)

Finely ground 1H-1,2,4-triazole (278 g, 4.02 mol) was mixed with acetonitrile (700 mL), cooled to 0° C., and treated drop-wise with phosphorus oxychloride (62.4 mL, 669 mmol) while maintaining the internal temperature below 15° C. The suspension was stirred for 10 minutes, then slowly treated drop-wise with triethylamine (607 mL, 4.35 mol) under vigorous stirring, while keeping the internal temperature below 48° C. The reaction was stirred for 15 minutes as it cooled to 41° C., and was then treated portion-wise with 7-methyl-5-(1-methyl-1H-pyrazol-4-yl)imidazo[5,1-f][1,2,4]triazin-4(3H)-one (77.1 g, 335 mmol). At the completion of the addition, the reaction was warmed to 73° C. for 1 hour, then cooled to room temperature, at which point thin layer chromatography (Eluant: 10% methanol in ethyl acetate) indicated complete conversion to the triazole-substituted intermediate. The reaction slurry was treated successively with triethylamine (279 mL, 2.00 mol) and azetidine hydrochloride (94.0 g, 1.00 mol); over 10 minutes, the internal temperature rose from 18° C. to 38° C. The mixture was stirred for 1 hour, cooled to 15-20° C. and filtered. The filter cake was washed with acetonitrile (600 mL), and the filtrate was concentrated in vacuo. The resulting paste was diluted with water (650 mL) followed by aqueous sodium hydroxide solution (10 N, 450 mL). This slurry was extracted with dichloromethane (3×350 mL), and the combined organic layers were dried over sodium sulfate and filtered. This filtrate was passed through a plug of silica gel (230-400 mesh, 150 g), eluting with dichloromethane (1 L) followed by 10% methanol in ethyl acetate (1 L). The combined eluants containing product were concentrated in vacuo, and the residue was washed with tert-butyl methyl ether (350 mL), collected by filtration, and washed with diethyl ether. This solid was dissolved in water (200 mL) and diluted once more with aqueous sodium hydroxide solution (5 N, 250 mL). The mixture was extracted with dichloromethane (3×250 mL), and the combined organic layers were dried over sodium sulfate, filtered and concentrated in vacuo. The solid was washed with tert-butyl methyl ether (350 mL) and collected by filtration to afford C2 as a pale tan solid. Yield: 82.15 g, 305 mmol, 91%. $^1$H NMR (500 MHz, CDCl$_3$) δ 2.23-2.30 (m, 2H), 2.65 (s, 3H), 3.96 (s, 3H), 3.98-4.07 (m, 4H), 7.61 (br s, 1H), 7.61 (br s, 1H), 7.85 (s, 1H).

Step 8. Synthesis of 4-(azetidin-1-yl)-7-methyl-5-{1-methyl-5-[5-(trifluoromethyl)pyridin-2-yl]-1H-pyrazol-4-yl}imidazo[5,1-f][1,2,4]triazine 4-(Azetidin-1-yl)-7-methyl-5-(1-methyl-1H-pyrazol-4-yl)imidazo[5,1-f][1,2,4]triazine (10.0 g, 37.1 mmol), 2-bromo-5-(trifluoromethyl)pyridine (16.8 g, 74.3 mmol) and ground potassium carbonate (15.4 g, 111 mmol) were combined in a reaction flask, purged with nitrogen, and treated with degassed 1,4-dioxane (600 mL). To this mixture was added allylpalladium(II) chloride dimer (693 mg, 1.86 mmol), and the system was again purged with nitrogen. The reaction was heated to 102° C. for 36 hours, then cooled and concentrated in vacuo. The residue was partitioned between ethyl acetate (400 mL) and aqueous hydrochloric acid solution (1 N, 200 mL). The aqueous phase was neutralized with solid sodium bicarbonate and extracted with ethyl acetate (4×50 mL). The combined organic layers were washed with 1 N aqueous citric acid, then with saturated aqueous sodium bicarbonate solution. After treatment with Darco® activated carbon, the organic layer was dried over sodium sulfate, filtered, and concentrated in vacuo. The residue was taken up in a minimal amount of dichloromethane and concentrated under reduced pressure until it became a thick oil. Diethyl ether (100 mL) was added, and upon stirring of the mixture, a solid began to precipitate; stirring was continued for 1 hour at room temperature, and then the white solid was collected by filtration and washed with diethyl ether. Additional product in the mother liquor was isolated by concentrating the filtrate in vacuo and chromatographing the residue on an alumina column (Eluant: 70% ethyl acetate in heptane). The product from the column was recrystallized from warm 20% ethyl acetate in heptane to yield additional product as a white solid. Combined yield: 5.3 g, 12.8 mmol, 35%. This material was combined with the product of a similar reaction (total 15.5 g, 37.4 mmol), and further purified as follows. The material was dissolved in a mixture of ethyl acetate (100 mL) and 2-methyltetrahydrofuran (150 mL) at room temperature. SiliaBond® thiol (SiliCycle, 1.35 mmol/g, 15 g) was added, and the mixture was stirred for 20 hours, then filtered through Celite. The filtrate was treated with Darco® activated carbon (500 mg) and stirred for 15 minutes before being filtered and concentrated under reduced pressure. The resulting oil was azeotroped with a 1:1 mixture of heptane and ethyl acetate to provide an off-white solid, which was mixed with heptane (100 mL) and stirred at room temperature for 6 hours. Filtration provided the product as a white solid. Purification yield: 14.4 g, 34.7 mmol, 93%. LCMS m/z 415.0 (M+1). $^1$H NMR (400 MHz, CDCl$_3$) δ 2.17-2.26 (m, 2H), 2.70 (s, 3H), 3.3-3.8

(v br m, 2H), 3.8-4.3 (v br m, 2H), 4.18 (s, 3H), 7.63-7.66 (m, 1H), 7.66 (s, 1H), 7.79-7.83 (m, 2H), 8.95-8.96 (m, 1H).

Example 3

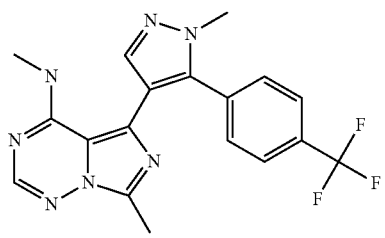 [SMILES: CNc1ncnn2c(C)nc(-c3cnn(C)c3-c3ccc(C(F)(F)F)cc3)c12]

N,7-Dimethyl-5-{1-methyl-5-[4-(trifluoromethyl)phenyl]-1H-pyrazol-4-yl}imidazo[5,1-f][1,2,4]triazin-4-amine

Step 1. Synthesis of ethyl 5-bromo-1-methyl-1H-pyrazole-4-carboxylate

Copper(II) bromide (99%, 20.0 g, 88.6 mmol) and tert-butyl nitrite (90%, 14.1 mL, 107 mmol) were combined in acetonitrile (65 mL) and heated to 65° C. Ethyl 5-amino-1-methyl-1H-pyrazole-4-carboxylate (10.0 g, 59.1 mmol) was slowly added portion-wise {Caution: gas evolution!} and the reaction was maintained at 65° C. for 24 hours. The mixture was cooled to room temperature, poured into aqueous hydrochloric acid (3 N, 600 mL), diluted with ethyl acetate (300 mL) and stirred for 10 minutes. The aqueous layer was extracted with ethyl acetate (150 mL), and the combined organic layers were dried over magnesium sulfate, filtered and concentrated in vacuo. The residue was purified via silica gel chromatography (Gradient: 5% to 100% ethyl acetate in heptane, with a 5-minute hold at 32%), affording the product as a pale yellow solid. Yield: 9.10 g, 39.0 mmol, 66%. LCMS m/z 233.3 (M+1). $^1$H NMR (500 MHz, CDCl$_3$) δ 1.36 (t, J=7.1 Hz, 3H), 3.92 (s, 3H), 4.32 (q, J=7.1 Hz, 2H), 7.93 (s, 1H).

Step 2. Synthesis of 5-bromo-1-methyl-1H-pyrazole-4-carboxylic acid

A suspension of ethyl 5-bromo-1-methyl-1H-pyrazole-4-carboxylate (8.00 g, 34.3 mmol) in tetrahydrofuran (60 mL), water (20 mL) and ethanol (20 mL) was treated with lithium hydroxide monohydrate (3.17 g, 75.5 mmol) and stirred for 4 hours at room temperature. Removal of solvents under reduced pressure provided a white solid residue, which was diluted with water (50 mL), washed with diethyl ether (50 mL) and adjusted to pH 2.5 with aqueous 6 N hydrochloric acid. The thick suspension was extracted with 2-methyltetrahydrofuran (2×125 mL), and the combined organic layers were dried over magnesium sulfate, filtered and concentrated in vacuo to provide the product as an off-white solid. Yield: 6.49 g, 31.7 mmol, 92%. LCMS m/z 205.2 (M+1). $^1$H NMR (500 MHz, DMSO-d$_6$) δ 3.86 (s, 3H), 7.91 (s, 1H), 12.64 (br s, 1H).

Step 3. Synthesis of 2-bromo-1-(5-bromo-1-methyl-1H-pyrazol-4-yl)ethanone

A solution of 5-bromo-1-methyl-1H-pyrazole-4-carboxylic acid (6.4 g, 31 mmol) in methanol (100 mL) was placed in a water bath, treated in a single portion with sodium methoxide (95%, 1.86 g, 32.7 mmol) and stirred for 30 minutes at room temperature. After removal of volatiles in vacuo, the sodium salt was concentrated twice from heptane (100 mL). It was then suspended in dichloromethane (100 mL) and treated with oxalyl chloride (3.15 mL, 35.9 mmol) followed by N,N-dimethylformamide (2 drops). The reaction was stirred for 20 hours at room temperature, then concentrated under reduced pressure. The solid residue was suspended in acetonitrile (100 mL), treated drop-wise with a solution of (trimethylsilyl)diazomethane in diethyl ether (2 M, 39.0 mL, 78.0 mmol) and stirred for 3 hours. The mixture was cooled to 0° C. and hydrogen bromide (33% in acetic acid, 21.9 mL, 125 mmol) was added drop-wise. After 1 hour at 0° C., the reaction mixture was concentrated, and the solid residue was mixed with heptane (250 mL) and reconcentrated. The residue was diluted with ethyl acetate (100 mL), and vigorously stirred with saturated aqueous sodium bicarbonate solution (100 mL). The organic layer was dried over magnesium sulfate, filtered and concentrated in vacuo; the crude product was purified via silica gel chromatography (Gradient: 12% to 100% ethyl acetate in heptane) to afford the product as an off-white solid, of approximately 85% purity by LCMS analysis. Yield: 8.10 g, approximately 78% (corrected for purity). LCMS m/z 282.8 (M+1). $^1$H NMR (500 MHz, CDCl$_3$) δ 3.93 (s, 3H), 4.25 (s, 2H), 8.01 (s, 1H).

Step 4. Synthesis of tert-butyl [4-(5-bromo-1-methyl-1H-pyrazol-4-yl)-2-methyl-1H-imidazol-1-yl]carbamate tert-Butyl 2-ethanimidoylhydrazinecarboxylate (5.9 g, 34 mmol), 2-bromo-1-(5-bromo-1-methyl-1H-pyrazol-4-yl)ethanone (from the previous step, 8.00 g, approximately 24 mmol) and N,N-diisopropylethylamine (10.9 mL, 62.6 mmol) were heated to reflux in a mixture of 2-methyltetrahydrofuran (200 mL) and 1,2-dimethoxyethane (50 mL). After 2.5 hours, the reaction was cooled and washed with 50% saturated aqueous sodium chloride solution (75 mL). The aqueous layer was extracted with 2-methyltetrahydrofuran (50 mL), and the combined organic layers were dried over magnesium sulfate, filtered and concentrated in vacuo. The residue was chromatographed (Gradient: 0% to 8% methanol in dichloromethane), and the purified material (7.5 g) was dissolved in diethyl ether (25 mL), treated with hexane (4 drops), and allowed to crystallize. The resulting solid was collected and washed with a small amount of cold diethyl ether to provide the product as a very pale pink solid. Yield: 6.49 g, 18.2 mmol, 59% over 2 steps. LCMS m/z 358.4 (M+1). $^1$H NMR (500 MHz, CDCl$_3$) δ 1.49 (br s, 9H), 2.16 (br s, 3H), 3.85 (s, 3H), 7.17 (s, 1H), 7.89 (s, 1H), 8.8-9.3 (v br s, 1H).

Step 5. Synthesis of 4-(5-bromo-1-methyl-1H-pyrazol-4-yl)-2-methyl-1H-imidazol-1-amine, trifluoroacetate salt tert-Butyl [4-(5-bromo-1-methyl-1H-pyrazol-4-yl)-2-methyl-1H-imidazol-1-yl]carbamate (5.00 g, 14.0 mmol) was dissolved in dichloromethane (120 mL), treated with trifluoroacetic acid (20.9 mL, 281 mmol), and stirred for 2.5 hours. After removal of volatiles in vacuo, the oily residue was diluted with diethyl ether (100 mL). The resulting suspension was stirred for 30 minutes at room temperature, and then the solid was collected and washed with diethyl ether to provide the product as an off-white solid. Yield: 4.98 g, 13.5 mmol, 96%. LCMS m/z 256.3 (M+1). $^1$H NMR (500 MHz, CD$_3$OD) δ 2.65 (s, 3H), 3.95 (s, 3H), 7.68 (s, 1H), 7.86 (s, 1H).

Step 6. Synthesis of N-[4-(5-bromo-1-methyl-1H-pyrazol-4-yl)-2-methyl-1H-imidazol-1-yl]imidoformamide 4-(5-Bromo-1-methyl-1H-pyrazol-4-yl)-2-methyl-1H-imidazol-1-amine, trifluoroacetate salt (4.90 g, 113.2 mmol) was combined with formamidine acetate (98%, 4.92 g, 46.3 mmol) in 2-butanol (40 mL), and the reaction mixture was heated at 100° C. for 6 hours, then allowed to cool to room temperature and stir for 18 hours. The off-white solid was collected by filtration and washed with 2-propanol followed by diethyl ether. The solid was then triturated with aqueous ammonium hydroxide (7.5 M, 40 mL); filtration provided a white solid, which was washed with 2-propanol followed by diethyl ether to provide the product. Yield: 2.70 g, 9.54 mmol, 72%. $^1$H NMR (500 MHz, CD$_3$OD), presumed to be a mixture of rotamers or tautomers: δ 2.26 and 2.31 (2 s, 3H), 3.89 and 3.89 (2 s, 3H), 7.26 and 7.40 (2 s, 1H), 7.41 and 7.96 (2 br s, 1H), 7.85 and 7.82 (2 s, 1H).

Step 7. Synthesis of 5-(5-bromo-1-methyl-1H-pyrazol-4-yl)-7-methylimidazo[5,1-f][1,2,4]triazin-4(3H)-one (C3)

1,1'-Carbonylbis(1H-1,2,4-triazole) (90%, 2.69 g, 14.8 mmol) and N-[4-(5-bromo-1-methyl-1H-pyrazol-4-yl)-2-methyl-1H-imidazol-1-yl]imidoformamide (2.69 g, 9.50 mmol) were combined in 1,4-dioxane (63 mL) and the mixture was stirred for 3.5 hours at room temperature, then heated to 50° C. for 1 hour. Additional 1,1'-carbonylbis(1H-1,2,4-triazole) (90%, 1.34 g, 7.35 mmol) was added, and heating was continued for 30 minutes. After another addition of 1,1'-carbonylbis(1H-1,2,4-triazole) (90%, 269 mg, 1.48 mmol), heating at 50° C. was carried out for an additional 75 minutes. The reaction was allowed to cool to room temperature, and was then concentrated to half its original volume; the precipitate was collected and washed with ethyl acetate to afford a white solid. This was dissolved in methanol (50 mL), concentrated to dryness and triturated with water (25 mL). After collection of the solid, it was washed with 2-propanol followed by diethyl ether to provide C3 as a white solid. Yield: 1.95 g, 6.31 mmol, 66%. LCMS m/z 309.4 (M+1). $^1$H NMR (500 MHz, DMSO-d$_6$) δ 2.53 (s, 3H), 3.87 (s, 3H), 7.87 (s, 1H), 8.17 (s, 1H), 11.69 (br s, 1H).

Step 8. Synthesis of 5-(5-bromo-1-methyl-1H-pyrazol-4-yl)-7-methyl-4-(1H-1,2,4-triazol-1-yl)imidazo[5,1-f][1,2,4]triazine 1H-1,2,4-Triazole (4.49 g, 65.0 mmol) was mixed with acetonitrile (40 mL) and cooled to 0° C. Phosphorus oxychloride (1.78 mL, 19.4 mmol) was added, followed by drop-wise addition of triethylamine (10.9 mL, 78.2 mmol). The temperature was maintained at 15-20° C. for 30 minutes after the completion of the addition. At this point, 5-(5-bromo-1-methyl-1H-pyrazol-4-yl)-7-methylimidazo[5,1-f][1,2,4]triazin-4(3H)-one (2.0 g, 6.5 mmol) was added, and the reaction mixture was allowed to warm to room temperature, then heated to 70° C. for 18 hours. The reaction was cooled and poured into a 10° C. solution of potassium phosphate (97%, 6.56 g, 30.0 mmol) in water (30 mL). After stirring for 5 minutes, the mixture was treated with solid sodium chloride (5 g) and stirred for an additional 5 minutes. The layers were separated, and the aqueous layer was extracted twice with ethyl acetate. The combined organic layers were washed with saturated aqueous sodium chloride solution, dried over sodium sulfate, and filtered. Removal of solvents in vacuo provided the crude product as an orange paste (2.1 g; contained some triethylamine by $^1$H NMR), which was used in the next reaction without additional purification. $^1$H NMR (400 MHz, CDCl$_3$), product peaks: δ 2.86 (s, 3H), 3.89 (s, 3H), 7.66 (s, 1H), 7.94 (s, 1H), 8.36 (s, 1H), 8.95 (s, 1H).

Step 9. Synthesis of 5-(5-bromo-1-methyl-1H-pyrazol-4-yl)-N,7-dimethylimidazo[5,1-f][1,2,4]triazin-4-amine (C4)

Methylamine (4.31 mL of a 2 M solution in tetrahydrofuran, 8.62 mmol) was added to a mixture of cesium carbonate (9.78 g, 30.0 mmol) and 5-(5-bromo-1-methyl-1H-pyrazol-4-yl)-7-methyl-4-(1H-1,2,4-triazol-1-yl)imidazo[5,14][1,2,4]triazine (from the previous reaction, 2.1 g) in N,N-dimethylformamide (12 mL), and the reaction was stirred at room temperature for 1 hour. It was quenched with a 1:1 mixture of water and saturated aqueous sodium chloride solution, then extracted with ethyl acetate (2×20 mL) and with tetrahydrofuran (10 mL). The combined organic layers were dried over sodium sulfate, filtered and concentrated in vacuo to provide C4. Yield: 1.65 g, 5.12 mmol, 78% over 2 steps. LCMS m/z 322.1 (M+1). $^1$H NMR (500 MHz, CDCl$_3$) δ 2.70 (s, 3H), 3.10 (d, J=4.9 Hz, 3H), 4.00 (s, 3H), 5.46-5.52 (m, 1H), 7.69 (s, 1H), 7.97 (s, 1H).

Step 10. Synthesis of N,7-dimethyl-5-{1-methyl-5-[4-(trifluoromethyl)phenyl]-1H-pyrazol-4-yl}imidazo[5,1-f][1,2,4]triazin-4-amine 5-(Bromo-1-methyl-1H-pyrazol-4-yl)-N,7-dimethylimidazo[5,1-f][1,2,4]triazin-4-amine (13.26 g, 41.16 mmol) and [4-(trifluoromethyl)phenyl]boronic acid (98%, 9.72 g, 50.2 mmol) were combined in ethanol (126 mL), and the resulting slurry was treated with a solution of potassium phosphate (98%, 11.13 g, 51.39 mmol) in water (42 mL) and warmed to 70° C. over 40 minutes while a vigorous nitrogen flow was applied through a bubbler. After addition of tetrakis(triphenylphosphine)palladium(0) (482 mg, 0.417 mmol), the reaction mixture was heated at reflux for 3.5 hours, then cooled to room temperature and stirred for an additional 16 hours. The mixture was filtered through a plug of cotton, and the filtrate was concentrated in vacuo, then reconcentrated with 2-methyltetrahydrofuran (2×200 mL). The residue was reconstituted in 2-methyltetrahydrofuran (150 mL) and extracted with aqueous hydrochloric acid (1 M, 70 mL, stirred for 20 minutes). The aqueous layer (pH ~2-3) was discarded. [This step removes most of the debrominated starting material; it is important that the pH of the HCl wash is ≥2.] The organic layer was then extracted twice with 1 M aqueous hydrochloric acid: first with 100 mL (stirring for 40 minutes), then with 75 mL (stirring for 20 minutes). The 100 mL aqueous layer was back-extracted with 2-methyltetrahydrofuran (80 mL, stirred for 30 minutes) to remove some color. The two hydrochloric acid layers were combined and treated with aqueous sodium hydroxide solution (5 M, 35.5 mL), which adjusted the pH to 6. The resulting mixture was extracted with 2-methyltetrahydrofuran (130 mL); the organic layer was passed through a plug of sodium sulfate (74 g) and concentrated in vacuo to a volume of roughly 150 mL. This was treated with Darco® G-60 activated carbon (5.03 g), and spun on a rotary evaporator in a 50° C. water bath for 1 hour. The warm solution was filtered through a pad of Celite, rinsing with 2-methyltetrahydrofuran, and the filtrate was concentrated under reduced pressure. The resulting pale yellow foam was treated with tert-butyl methyl ether (150 mL) and swirled in a 50° C. water bath for 5 minutes, then was cooled to room temperature with stirring over 1 hour. The resulting slurry was cooled in an ice bath and held for an additional 30 minutes. The solids were collected by filtration and rinsed with chilled tert-butyl methyl ether (cooled with a bath of ice-saturated aqueous sodium chloride solution; 79 mL), then slurried in heptane (150 mL). This mixture was concentrated in vacuo to a small volume and reconcentrated with heptane (2×150 mL), to a final volume of approximately 50 mL. Filtration provided the product as a white solid. Yield: 11.91 g, 30.75 mmol, 75%. LCMS m/z 388.2 (M+1). $^1$H NMR (400 MHz, CDCl$_3$) δ 2.65 (br s, 3H), 3.00 (d, J=5.0 Hz, 3H), 3.95 (s, 3H), 5.49-5.57 (m, 1H), 7.61 (br AB quartet, J$_{AB}$=8.2 Hz, Δv$_{AB}$=41.4 Hz, 4H), 7.73 (s, 1H), 7.91 (br s, 1H).

Example 4

4-(Azetidin-1-yl)-5-[5-(4-chlorophenyl)-1-methyl-1H-pyrazol-4-yl]-7-methylimidazo[5,1-f][1,2,4]triazine

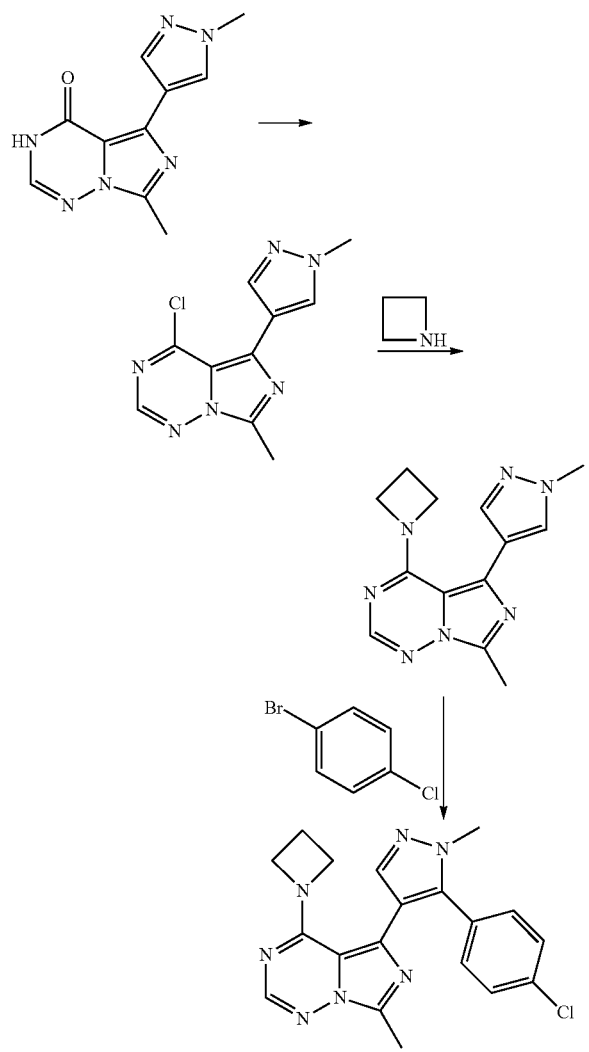

Step 1. Synthesis of 4-chloro-7-methyl-5-(1-methyl-1H-pyrazol-4-yl)imidazo[5,1-f][1,2,4]triazine Phosphorus oxychloride (16.07 g, 104.8 mmol) was added over 5 minutes to a slurry of 7-methyl-5-(1-methyl-1H-pyrazol-4-yl)imidazo[5,1-f][1,2,4]triazin-4(3H)-one (11.98 g, 52.03 mmol) in toluene (180 mL). N,N-Diisopropylethylamine (27.04 g, 209.2 mmol) was added, and the reaction mixture was heated at 100° C. for 15 hours. The mixture was cooled to room temperature, at which point LCMS analysis indicated that the reaction was not complete; additional phosphorus oxychloride (3.98 g, 26.0 mmol) was added, and the reaction was heated at 100° C. for 22 hours. The mixture was cooled to room temperature, diluted with dichloromethane (24 mL) and stirred for 48 hours at room temperature. Over 50 minutes, the reaction mixture was added to a mixture of triethylamine (58 mL), toluene (60 mL) and water (120 mL), while the internal temperature was maintained below 34° C. Stirring was continued for an additional 15 minutes. The aqueous layer was extracted once with toluene (120 mL), and the combined organic layers were washed with saturated aqueous sodium chloride solution (200 mL) and dried by passing through a plug of sodium sulfate (71 g). The filtrate was concentrated in vacuo to provide crude product as a dark orange solid (9.77 g); this was treated with tetrahydrofuran (60 mL) and warmed to reflux for 15 minutes to provide a solution. This was cooled to room temperature over 30 minutes, granulated for 30 minutes, then cooled in an ice bath and stirred for 30 minutes. The resulting solid was collected by filtration and the filter cake was rinsed with pre-chilled tert-butyl methyl ether (cooled with a bath of ice-saturated aqueous sodium chloride solution; 65 mL). The product was obtained as a bright orange solid. Yield: 7.59 g, 30.5 mmol, 59%. LCMS m/z 249.0 (M+1). $^1$H NMR (400 MHz, CDCl$_3$) δ 2.75 (s, 3H), 3.99 (s, 3H), 7.90 (s, 1H), 8.00 (s, 1H), 8.12 (s, 1H).

Step 2. Synthesis of 4-(azetidin-1-yl)-7-methyl-5-(1-methyl-1H-pyrazol-4-yl)imidazo[5,1-f][1,2,4]triazine A solution of azetidine (9.21 g, 161 mmol) in dichloromethane (75 mL) was added to a solution of 4-chloro-7-methyl-5-(1-methyl-1H-pyrazol-4-yl)imidazo[5,1-f][1,2,4]triazine (38.14 g, 153.4 mmol) in dichloromethane (310 mL). After stirring for 5 minutes, the reaction was treated with aqueous sodium bicarbonate solution (0.89 M, 260 mL, 231 mmol) and vigorously stirred for 2 hours. After the phases separated, a white solid was collected by filtration and mixed with water and dichloromethane; it did not completely dissolve. Filtration provided a second water/dichloromethane mixture, which was combined with the original filtrate. The layers were separated, and the aqueous layer was extracted with dichloromethane (3×100 mL). The combined organic layers were washed with saturated aqueous sodium chloride solution (250 mL), then dried over sodium sulfate and filtered. The filtrate was concentrated on a rotary evaporator at 45° C. until solid began to form in the flask. tert-Butyl methyl ether (400 mL) was added with stirring, and the mixture was granulated for 1 hour. Filtration provided the product as a white solid. Yield: 36.07 g, 133.9 mmol, 87%. $^1$H NMR (400 MHz, CDCl$_3$) δ 2.23-2.31 (m, 2H), 2.65 (s, 3H), 3.97 (s, 3H), 3.98-4.08 (m, 4H), 7.61 (s, 1H), 7.62 (s, 1H), 7.85 (s, 1H).

Step 3. Synthesis of 4-(azetidin-1-yl)-5-[5-(4-chlorophenyl)-1-methyl-1H-pyrazol-4-yl]-7-methylimidazo[5,1-f][1,2,4]triazine 4-(Azetidin-1-yl)-7-methyl-5-(1-methyl-1H-pyrazol-4-yl)imidazo[5,1-f][1,2,4]triazine (10.0 g, 37.1 mmol), 1-bromo-4-chlorobenzene (14.2 g, 74.2 mmol), freshly ground potassium carbonate (15.4 g, 111 mmol) and allylpalladium(II) chloride dimer (970 mg, 2.60 mmol) were combined in a reaction flask; the flask was then evacuated under vacuum and flushed with nitrogen. 1,4-Dioxane (180 mL) was added, and the reaction was stirred at room temperature. The mixture was degassed under vacuum, and nitrogen was bubbled through it for 5 minutes. The evacuation-nitrogen purge procedure was repeated an additional two times. The reaction was heated to 100° C. for 72 hours, then cooled to room temperature and combined with an identical reaction carried out on 5.0 g of 4-(azetidin-1-yl)-7-methyl-5-(1-methyl-1H-pyrazol-4-yl)imidazo[5,1-f][1,2,4]triazine. The combined reaction mixtures were concentrated in vacuo, and after suspension in ethyl acetate, the residue was applied to a pad of silica gel topped with Celite. The pad was eluted with ethyl acetate (1.5 L) followed by a 9:1 mixture of ethyl acetate/methanol (1 L). The combined eluants were concentrated in vacuo to provide an oil (25 g), which was dissolved in ethyl acetate (500 mL) and extracted with aqueous hydrochloric acid (1 M, 300 mL). The aqueous layer was basified with aqueous 1 M sodium hydroxide solution, and extracted with ethyl acetate (2×250 mL). The two organic layers were combined and washed with aqueous citric acid (1 M, 200 mL), and the aqueous citric acid layer was extracted with ethyl acetate (8×100 mL). The combined organic layers were then washed with a 1:1 mixture of saturated aqueous sodium bicarbonate solution/saturated aqueous sodium chloride solution, dried over magnesium sulfate, filtered and concentrated under reduced pressure. The resulting solid was stirred in a hot mixture of heptane (~100 mL) and ethyl acetate (~15 mL), cooled to room temperature and stirred for 16 hours. The solid was isolated via filtration to provide a white powder (10.6 g). To remove residual palladium (0.3% by QTI Analytical Services analysis), this material was dissolved in a mixture of ethyl acetate (100 mL) and 2-methyltetrahydrofuran (150 mL) at room temperature and treated with SiliaBond® thiol (SiliCycle, 1.35 mmol/g, 5 g, 6.75 mmol of activity). The mixture was stirred for 20 hours, then filtered through Celite. The filtrate was treated with Darco® activated carbon (500 mg) and stirred for 15 minutes before being filtered and concentrated under reduced pressure. The resulting oil was azeotroped with a 1:1 mixture of heptane and ethyl acetate to provide a white solid (9.9 g), which was triturated with a mixture of heptane (80 mL) and ethyl acetate (10 mL) at reflux, then cooled to room temperature and stirred for an additional 36 hours. Filtration provided the product as a white solid. Yield: 9.48 g, 25.0 mmol, 67%. LCMS m/z 380.0 (M+1). $^1$H NMR (500 MHz, CDCl$_3$) δ 2.21-2.28 (m, 2H), 2.63 (s, 3H), 3.4-4.4 (v br m, 4H), 3.90 (s, 3H), 7.31-7.36 (m, 4H), 7.64 (s, 1H), 7.80 (s, 1H).

Example 5

4-(Azetidin-1-yl)-5-[5-(5-chloropyridin-2-yl)-1-methyl-1H-pyrazol-4-yl]-7-methylimidazo[5,1-f][1,2,4]triazine

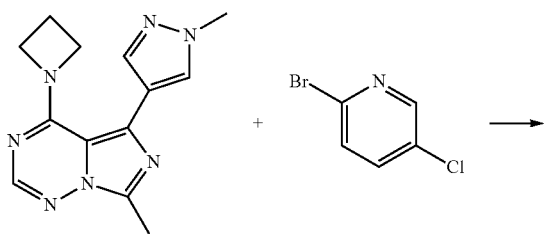

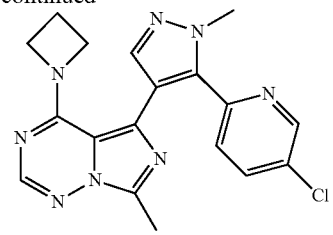

Synthesis of the title product was carried out according to the procedure for the synthesis of 4-(azetidin-1-yl)-7-methyl-5-{1-methyl-5-[5-(trifluoromethyl)pyridin-2-yl]-1H-pyrazol-4-yl}imidazo[5,1-f][1,2,4]triazine in Example 2, except that 2-bromo-5-chloropyridine was used in place of 2-bromo-5-(trifluoromethyl)pyridine. In this case, after the citric acid wash, the organic layer was dried, filtered and concentrated under reduced pressure to provide a pale yellow solid, which was then recrystallized from methanol. The solid was dissolved in 2-methyltetrahydrofuran (300 mL), treated with silica gel and stirred for 18 hours. Darco® activated carbon (2 g) was added, and the mixture was stirred for 30 minutes, at which time it was filtered through a pad of Celite and concentrated in vacuo to provide the product as a white solid. Yield: 17.6 g, 46.2 mmol, 52%. LCMS m/z 381.0 (M+1). $^1$H NMR (400 MHz, CDCl$_3$) δ 2.16-2.25 (m, 2H), 2.69 (s, 3H), 3.3-3.8 (v br m, 2H), 3.8-4.3 (v br m, 2H), 4.12 (s, 3H), 7.40 (dd, J=8.5, 0.7 Hz, 1H), 7.54 (dd, J=8.5, 2.5 Hz, 1H), 7.64 (s, 1H), 7.81 (s, 1H), 8.65 (dd, J=2.5, 0.7 Hz, 1H).

Example 6

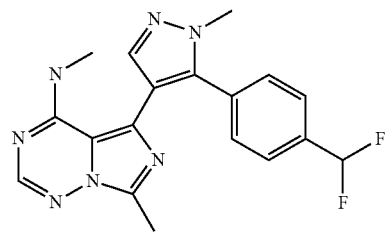 [SMILES: CNc1ncnn2c(C)nc(-c3cnn(C)c3-c3ccc(C(F)F)cc3)c12]

5-{5-[4-(Difluoromethyl)phenyl]-1-methyl-1H-pyrazol-4-yl}-N,7-dimethylimidazo[5,1-f][1,2,4]triazin-4-amine Step 1. Synthesis of 2-[4-(difluoromethyl)phenyl]-4,4,5,5-tetramethyl-1,3,2-dioxaborolane (C5)

A. Synthesis of 1-bromo-4-(difluoromethyl)benzene (Diethylamino)sulfur trifluoride (46 g, 0.29 mol) was added portion-wise over 20 minutes to a solution of 4-bromobenzaldehyde (37.7 g, 0.204 mmol) in dichloromethane (170 mL), and the reaction mixture was heated at reflux for 1 hour. It was then allowed to cool to room temperature, stirred for 18 hours, and slowly added over 30 minutes to a stirring solution of saturated aqueous sodium bicarbonate (377 mL) at 0° C. The biphasic mixture was allowed to warm to room temperature, and stirred for 15 minutes. The aqueous layer was extracted with dichloromethane (2×80 mL) and the combined organic layers were washed with saturated aqueous sodium chloride solution (80 mL), dried over magnesium sulfate and concentrated in vacuo to provide a golden oil. The reaction was repeated an additional 10 times on 60 gram batches of 4-bromobenzaldehyde (total starting material: 638 g, 3.45 mol), and the resulting oils were combined and purified by distillation (b.p. 102° C. at 37 mm Hg) to provide the product as a colorless oil. Yield: 577.3 g, 2.79 mol, 81%. $^1$H NMR (400 MHz, CDCl$_3$) δ 6.62 (t, J=56.3 Hz, 1H), 7.40 (br d, J=8.4 Hz, 2H), 7.61 (br d, J=8.6 Hz, 2H).

B. Synthesis of 2-[4-(difluoromethyl)phenyl]-4,4,5,5-tetramethyl-1,3,2-dioxaborolane

[1,1'-Bis(diphenylphosphino)ferrocene]dichloropalladium(II) (25.25 g, 34.5 mmol) was added in one portion to a degassed mixture of 1-bromo-4-(difluoromethyl)benzene (160 g, 0.77 mol), 4,4,4',4',5,5,5',5'-octamethyl-2,2'-bi-1,3,2-dioxaborolane (392.5 g, 1.55 mol) and potassium acetate (303 g, 3.09 mol) in 1,4-dioxane (2.42 L), and the reaction was heated to 100° C. for 18 hours. The mixture was then cooled to room temperature and filtered through Celite, washing with ethyl acetate (3 L). The filtrate was concentrated in vacuo to give a dark brown oil. The reaction was repeated an additional 3 times, on batches of 50 g, 160 g and 156 g of 1-bromo-4-(difluoromethyl)benzene (total starting material, 526 g, 2.54 mol), and the combined crude products were purified twice by chromatography on silica gel (Gradient: 0% to 3% ethyl acetate in heptane) to provide a yellow-white solid (803 g). This was recrystallized from methanol (1.6 L) at −20° C., and the filtrate was concentrated to one-half its original volume, cooled, and the resulting solid was collected by filtration. The combined solids (426 g) were recrystallized from heptane (500 mL) at −20° C., then melted and poured into methanol (200 mL) cooled in a methanol-ice bath. The mixture was broken up and filtered to yield C5 as a solid. Yield: 250.7 g, 0.987 mmol, 39%. $^1$H NMR (400 MHz, CDCl$_3$) δ 1.37 (s, 12H), 6.65 (t, J=56.4 Hz, 1H), 7.52 (br d, J=8.1 Hz, 2H), 7.92 (br d, J=8.0 Hz, 2H).

Step 2. Synthesis of 5-{5-[4-(difluoromethyl)phenyl]-1-methyl-1H-pyrazol-4-yl}-N,7-dimethylimidazo[5,1-f][1,2,4]triazin-4-amine

[5-(5-Bromo-1-methyl-1H-pyrazol-4-yl)-N,7-dimethylimidazo[5,14][1,2,4]triazin-4-amine (13.01 g, 40.38 mmol) and 2-[4-(difluoromethyl)phenyl]-4,4,5,5-tetramethyl-1,3,2-dioxaborolane (12.75 g, 50.18 mmol) were combined in ethanol (126 mL), and the resulting slurry was treated with a solution of potassium phosphate (98%, 11.04 g, 50.97 mmol) in water (42 mL) and warmed to 70° C. over 30 minutes while a vigorous nitrogen flow was applied through a bubbler. After addition of tetrakis(triphenyl phosphine) palladium(0) (481 mg, 0.416 mmol), the reaction mixture was heated at reflux for 4 hours, then cooled to room temperature and stirred for an additional 16 hours. The mixture was filtered through a plug of cotton, and the filtrate was concentrated in vacuo, then reconcentrated with 2-methyltetrahydrofuran (2×150 mL). The residue was reconstituted in 2-methyltetrahydrofuran (150 mL) and extracted with aqueous hydrochloric acid (1 M, 70 mL, stirred for 20 minutes). The aqueous layer (pH ~2-3) was discarded. The organic layer was extracted twice with 1 M aqueous hydrochloric acid: first with 100 mL (stirring for 1 hour), then with 75 mL (stirring for 20 minutes). The 100 mL aqueous layer was back-extracted with 2-methyltetrahydrofuran (75 mL, stirred for 20 minutes) to remove a light yellow color; from this organic layer precipitated a solid, which was collected and rinsed with tert-butyl methyl ether to provide X-ray quality crystals. Single crystal X-ray analysis revealed this material to be the monohydrate of the hydrochloride salt of the product. The two hydrochloric acid layers were combined and treated with aqueous sodium hydroxide solution (5 M, 35.5 mL), which adjusted the pH to 6. The resulting mixture was extracted with 2-methyltetrahydrofuran (150 mL); the organic layer was passed through a plug of sodium sulfate (58 g) and concentrated in vacuo to a volume of roughly 150 mL. This yellow solution was treated with Darco® G-60 activated carbon (5.03 g), and spun on a rotary evaporator in a 50° C. water bath for 1.5 hours. The warm solution was filtered through a pad of Celite, and the filtrate was concentrated under reduced pressure. The resulting light yellow solid was treated with tert-butyl methyl ether (250 mL) and spun on a rotary evaporator in a 55° C. water bath for 1 hour. Roughly 100 mL of solvent was removed using the rotary evaporator, and the resulting mixture was cooled to room temperature with stirring over 1 hour. The slurry was then cooled in an ice bath and stirred for an additional 30 minutes. The solids were collected by filtration and rinsed with chilled tert-butyl methyl ether (cooled in ice-saturated aqueous sodium chloride solution bath; 50 mL) to provide the product as a powdery white solid. Yield: 11.27 g, 30.51 mmol, 76%. LCMS m/z 370.2 (M+1). $^1$H NMR (400 MHz, CDCl$_3$) δ 2.65 (br s, 3H), 2.98 (d, J=5.1 Hz, 3H), 3.94 (s, 3H), 5.48-5.55 (m, 1H), 6.65 (t, J=56.3 Hz, 1H), 7.52 (br AB quartet, J$_{AB}$=8.4 Hz, Δv$_{AB}$=17.9 Hz, 4H), 7.73 (s, 1H), 7.90 (br s, 1H).

Example 7

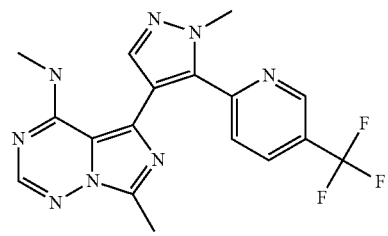 [SMILES: CNc1ncnn2c(C)nc(-c3cnn(C)c3-c3ccc(C(F)(F)F)cn3)c12]

N,7-Dimethyl-5-{1-methyl-5-[5-(trifluoromethyl)pyridin-2-yl]-1H-pyrazol-4-yl}imidazo[5,1f][1,2,4]triazin-4-amine Step 1. Synthesis of N-(4-methoxybenzyl)-N,7-dimethyl-5-(1-methyl-1H-pyrazol-4-yl)imidazo[5,1-f][1,2,4]triazin-4-amine (C6)

The product was synthesized in a manner similar to that described for the preparation of 4-(azetidin-1-yl)-7-methyl-5-(1-methyl-1H-pyrazol-4-yl)imidazo[5,1-f][1,2,4]triazine in Example 2, except that 1-(4-methoxyphenyl)-N-methylmethanamine was utilized in place of azetidine hydrochloride, and the workup was modified somewhat: after the slurry was extracted with dichloromethane, the combined organic layers were washed with 1 N aqueous sodium hydroxide solution, washed with saturated aqueous sodium chloride solution, and dried over sodium sulfate. After filtration, the filtrate was concentrated in vacuo and passed through a short column of silica gel (Eluant: 5% methanol in ethyl acetate). The eluant was concentrated under reduced pressure, and the resulting solid was washed with tert-butyl methyl ether followed by diethyl ether, to provide C6. Yield: 36.0 g, 99.1 mmol, 76%. LCMS m/z 364.2 (M+1). $^1$H NMR (400 MHz, CDCl₃) δ 2.67 (s, 3H), 2.84 (s, 3H), 3.77 (s, 3H), 3.88 (s, 3H), 4.66 (s, 2H), 6.82 (br d, J=8.7 Hz, 2H), 7.07 (br d, J=8.6 Hz, 2H), 7.58 (s, 1H), 7.62 (s, 1H), 7.89 (s, 1H).

Step 2. Synthesis of N-(4-methoxybenzyl)-N,7-dimethyl-5-{1-methyl-5-[5-(trifluoromethyl)pyridin-2-yl]-1H-pyrazol-4-yl}imidazo[5,1-f][1,2,4]triazin-4-amine N-(4-Methoxybenzyl)-N,7-dimethyl-5-(1-methyl-1H-pyrazol-4-yl)imidazo[5,1-f][1,2,4]triazin-4-amine (10.0 g, 27.5 mmol), 2-bromo-5-(trifluoromethyl)pyridine (12.4 g, 54.9 mmol) and powdered potassium carbonate (11.4 g, 82.5 mmol) were combined in 1,4-dioxane (90 mL) and heated at reflux for 10 minutes. Allylpalladium chloride dimer (98%, 514 mg, 1.38 mmol) was added, and the reaction was heated for 22 hours at 160° C. in a sealed tube capped with a Q-Tube™ (Q Labtech). The reaction was cooled to room temperature and concentrated in vacuo. The residue was suspended in ethyl acetate, filtered through Celite and concentrated under reduced pressure. Silica gel chromatography (Gradient: 50% to 100% ethyl acetate in heptane) provided a pale brown foam (7.85 g), which was crystallized from heptane (~100 mL) and ethyl acetate (~5 mL) to provide the product as a pale brown powder. Yield: 7.00 g, 13.8 mmol, 50%. LCMS m/z 509.1 (M+1). ¹H NMR (500 MHz, CDCl₃) δ 2.54 (s, 3H), 2.72 (s, 3H), 3.75 (s, 3H), 4.14 (s, 3H), 4.34 (br s, 2H), 6.76 (br d, J=8.8 Hz, 2H), 6.94 (br d, J=8.5 Hz, 2H), 7.39 (d, J=8.3 Hz, 1H), 7.72 (s, 1H), 7.76 (dd, J=8.3, 2.2 Hz, 1H), 7.85 (s, 1H), 8.95-8.96 (m, 1H).

Step 3. Synthesis of N,7-dimethyl-5-{1-methyl-5-[5-(trifluoromethyl)pyridin-2-yl]-1H-pyrazol-4-yl}imidazo[5,1-f][1,2,4]triazin-4-amine N-(4-Methoxybenzyl)-N,7-dimethyl-5-{1-methyl-5-[5-(trifluoromethyl)pyridin-2-yl]-1H-pyrazol-4-yl}imidazo[5,1-f][1,2,4]triazin-4-amine (7.00 g, 13.8 mmol) was dissolved in dichloromethane (46 mL) and treated with trifluoroacetic acid (40 mL, 520 mmol) and methoxybenzene (99.7%, 7.0 mL, 64 mmol). The reaction mixture was heated at 40° C. for 4 hours, then concentrated in vacuo. Aqueous 1 N sodium hydroxide solution was added, and the mixture was extracted with ethyl acetate. The organic layer was concentrated under reduced pressure to provide crude product (12 g), which was combined with the crude product from two additional runs of this reaction (total starting material: 18.09 g, 35.57 mmol). The combined material was dissolved in hot methanol, allowed to cool slightly, and treated with Darco® activated carbon (8 g); this mixture was heated for 1 hour at 50° C. and filtered through Celite. The volume of the filtrate was reduced, and the solution was left to crystallize for 18 hours. The resulting beige crystals were determined by ¹H NMR to contain residual methoxybenzene. Trituration with diethyl ether provided the product as a white solid. Combined yield: 8.73 g, 22.5 mmol, 63%. LCMS m/z 389.2 (M+1). ¹H NMR (400 MHz, CD₃OD) δ 2.58 (s, 3H), 2.85 (s, 3H), 4.15 (s, 3H), 7.38 (br d, J=8.3 Hz, 1H), 7.73 (s, 1H), 7.85 (s, 1H), 7.98-8.01 (m, 1H), 9.02-9.04 (m, 1H).

Alternate Preparation of N-(4-methoxybenzyl)-N,7-dimethyl-5-{1-methyl-5-[5-(trifluoromethyl)pyridin-2-yl]-1H-pyrazol-4-yl}imidazo[5,1-f][1,2,4]triazin-4-amine Step 1. Synthesis of 5-(5-bromo-1-methyl-1H-pyrazol-4-yl)-4-chloro-7-methylimidazo[5,1-f][1,2,4]triazine A mixture of 5-(5-bromo-1-methyl-1H-pyrazol-4-yl)-7-methylimidazo[5,1-f][1,2,4]triazin-4(3H)-one (10.00 g, 32.35 mmol) in toluene (100 mL) was treated with phosphorus oxychloride (9.05 mL, 97.1 mmol). After drop-wise addition of N,N-diisopropylethylamine (28.2 mL, 162 mmol), the mixture was heated at 105° C. for 24 hours. The reaction was allowed to cool to room temperature, and then was diluted with dichloromethane (20 mL) and added over 10 minutes to a solution comprised of triethylamine (30 mL), toluene (50 mL) and water (80 mL), while keeping the internal temperature below 36° C. After an additional 20 minutes of stirring, the phases were separated, and the aqueous layer (pH ~7) was extracted with toluene (100 mL). The combined organic layers were washed with aqueous citric acid solution (1 M, 150 mL), then washed with saturated aqueous sodium chloride solution, dried over magnesium sulfate and filtered. The filtrate was concentrated in vacuo to provide the product as a solid. Yield: 9.80 g, 29.9 mmol, 92%. LCMS m/z 328.9 (M+1). ¹H NMR (400 MHz, CDCl₃) δ 2.78 (s, 3H), 3.97 (s, 3H), 7.75 (s, 1H), 8.18 (s, 1H).

Step 2. Synthesis of 5-(5-bromo-1-methyl-1H-pyrazol-4-yl)-N-(4-methoxybenzyl)-N,7-dimethylimidazo[5,1-f][1,2,4]triazin-4-amine A solution of 5-(5-bromo-1-methyl-1H-pyrazol-4-yl)-4-chloro-7-methylimidazo[5,1-f][1,2,4]triazine (9.80 g, 29.9 mmol) in dichloromethane (100 mL) was treated with 1-(4-methoxyphenyl)-N-methylmethanamine (4.52 g, 29.9 mmol). After stirring at room temperature for 10 minutes, the reaction was diluted with saturated aqueous sodium bicarbonate solution (100 mL) and stirred for an additional hour. The organic layer was then washed with saturated aqueous sodium chloride solution, dried over magnesium sulfate, filtered, and concentrated under reduced pressure to afford the product as a solid. Yield: 12.9 g, 29.2 mmol, 98%. LCMS m/z 443.9 (M+1). ¹H NMR (400 MHz, CDCl₃) δ 2.71 (s, 3H), 2.79 (s, 3H), 3.78 (s, 3H), 3.89 (s, 3H), 4.67 (br s, 2H), 6.82 (br d, J=8.7 Hz, 2H), 7.10 (br d, J=8.6 Hz, 2H), 7.64 (s, 1H), 7.92 (s, 1H).

Step 3. Synthesis of N-(4-methoxybenzyl)-N,7-dimethyl-5-{1-methyl-5-[5-(trifluoromethyl)pyridin-2-yl]-1H-pyrazol-4-yl}imidazo[5,1-f][1,2,4]triazin-4-amine A solution of 5-(5-bromo-1-methyl-1H-pyrazol-4-yl)-N-(4-methoxybenzyl)-N,7-dimethylimidazo[5,1-f][1,2,4]triazin-4-amine (3.35 g, 7.57 mmol) in tetrahydrofuran (75 mL) was cooled to −78° C. and treated over 5 minutes with n-hexyllithium (2.3 M solution in hexane, 3.46 mL, 7.96 mmol). The reaction mixture was stirred for 30 minutes, and then treated in one portion with a −78° C. solution of zinc chloride (99.5%, 1.30 g, 9.49 mmol) in tetrahydrofuran (20 mL). After stirring for 5 minutes at −78° C., the reaction was warmed to room temperature over 30 minutes. After addition of 2-bromo-5-(trifluoromethyl)pyridine (2.57 g, 11.4 mmol), the reaction mixture was heated to 50° C., treated with tetrakis(triphenylphosphine)palladium(0) (99.9%, 87.9 mg, 0.076 mmol), and maintained at reflux for 4 hours. The reaction was cooled and concentrated in vacuo; the residue was dissolved in ethyl acetate and washed sequentially with water, saturated aqueous ammonium chloride solution, and saturated aqueous sodium bicarbonate solution. After drying over magnesium sulfate, the product solution was filtered and concentrated in vacuo. Purification via silica gel chromatography (Gradient: 0% to 100% ethyl acetate in heptane) provided a pale yellow oil (2.3 g), which was crystallized from heptane to afford the product as a white powder. Yield: 1.58 g, 3.11 mmol, 41%.

APCI m/z 509.5 (M+1). $^1$H NMR (400 MHz, CDCl$_3$) δ 2.54 (s, 3H), 2.72 (s, 3H), 3.76 (s, 3H), 4.14 (s, 3H), 4.34 (br s, 2H), 6.76 (br d, J=8.8 Hz, 2H), 6.94 (br d, J=8.5 Hz, 2H), 7.39 (d, J=8.3 Hz, 1H), 7.72 (s, 1H), 7.76 (dd, J=8.4, 2.2 Hz, 1H), 7.85 (s, 1H), 8.94-8.96 (m, 1H).

Example 8

4-(Azetidin-1-yl)-5-[5-(4-methoxy-2-methylphenyl)-1-methyl-1H-pyrazol-4-yl]-7-methylimidazo[5,1-f][1,2,4]triazine

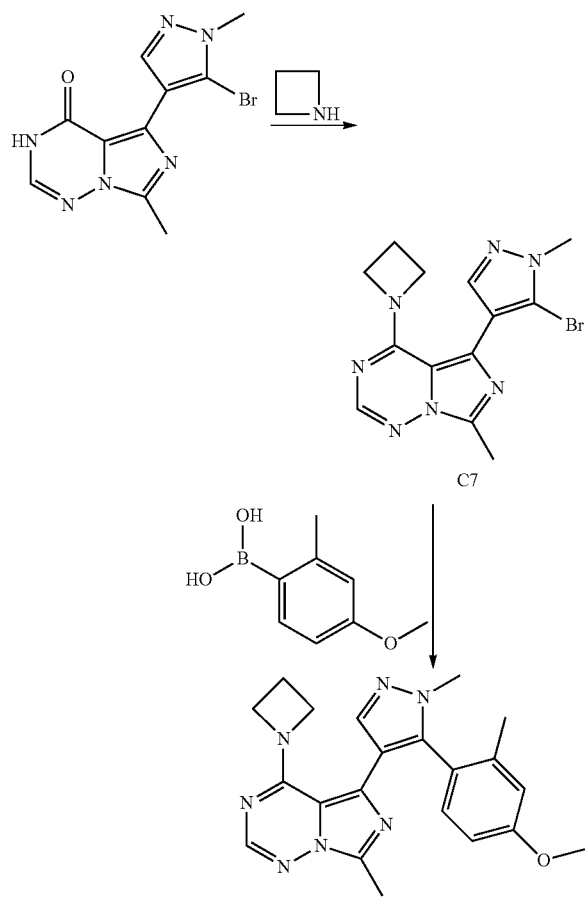

Step 1. Synthesis of 4-(azetidin-1-yl)-5-(5-bromo-1-methyl-1H-pyrazol-4-yl)-7-methylimidazo[5,1-f][1,2,4]triazine (C7)

A mixture of 5-(5-bromo-1-methyl-1H-pyrazol-4-yl)-7-methylimidazo[5,1-f][1,2,4]triazin-4(3H)-one (5.02 g, 16.2 mmol) and toluene (100 mL) was treated with phosphorus oxychloride (7.50 mL, 80.5 mmol) and heated to 45° C. N,N-Diisopropylethylamine (17.0 mL, 97.6 mmol) was added in four equal portions, waiting for the exotherm to subside before adding another portion. The reaction mixture was heated to 95° C. for 42 hours, cooled to 35° C. and added to an aqueous solution of potassium phosphate (2.5 M, 45.0 mL), also at 35° C., in four portions; during this addition the temperature rose to 63° C. The resulting mixture was filtered through Celite, which was then rinsed with additional toluene. The organic layer of the filtrate was washed with aqueous citric acid solution (0.57 M, 30 mL), then washed with saturated aqueous sodium chloride solution (25 mL) and dried over sodium sulfate. After filtration, the filtrate was concentrated in vacuo to a volume of approximately 100 mL. This was added to a solution of azetidine (2.34 g, 41.0 mmol) in tetrahydrofuran (20 mL), and the reaction mixture was stirred for 1 hour at room temperature, at which time it was poured in four portions into an aqueous sodium bicarbonate solution (0.65 M, 125 mL) with vigorous stirring. The aqueous layer was extracted with toluene (3×50 mL) and the combined organic layers were washed with saturated aqueous sodium chloride solution (25 mL), dried over sodium sulfate, filtered and concentrated in vacuo to a volume of approximately 75 mL. Heptane (100 mL) was added with vigorous stirring, and the mixture was granulated at room temperature for 2 hours, then cooled in an ice bath for 15 minutes. The resulting solid was collected by vacuum filtration to provide C7. Yield: 4.45 g, 12.8 mmol, 79%. $^1$H NMR (400 MHz, CDCl$_3$) δ 2.24-2.33 (m, 2H), 2.68 (s, 3H), 3.5-4.5 (v br m, 4H), 3.96 (s, 3H), 7.65 (s, 1H), 7.88 (s, 1H).

Step 2. Synthesis of 4-(azetidin-1-yl)-5-[5-(4-methoxy-2-methylphenyl)-1-methyl-1H-pyrazol-4-yl]-7-methylimidazo[5,1-f][1,2,4]triazine 4-(Azetidin-1-yl)-5-(5-bromo-1-methyl-1H-pyrazol-4-yl)-7-methylimidazo[5,1-f][1,2,4]triazine (200 mg, 0.574 mmol) was combined with (4-methoxy-2-methylphenyl)boronic acid (180 mg, 1.08 mmol), potassium phosphate dihydrate (98%, 571 mg, 2.25 mmol), tetrakis(triphenylphosphine)palladium(0) (99.9%, 65.9 mg, 0.057 mmol) and N,N-dimethylformamide (12 mL) and heated in a microwave reactor at 150° C. for 60 minutes. This reaction mixture was combined with crude reaction products from three other identical reactions, and poured into water. The mixture was extracted with ethyl acetate, and the combined organic layers were washed with water, then with saturated aqueous sodium chloride solution. After drying over sodium sulfate, the organic extracts were filtered and concentrated in vacuo. Purification via silica gel chromatography (Eluants: heptane/ethyl acetate/methanol mixtures, 90:15:10 followed by 60:30:10, 45:55:10, 30:70:10 ratios) provided the product as a solid. Combined yield: 508 mg, 1.30 mmol, 56%. LCMS m/z 390.2 (M+1). $^1$H NMR (400 MHz, CDCl$_3$) δ 2.08 (s, 3H), 2.26-2.35 (m, 2H), 2.60 (s, 3H), 3.69 (s, 3H), 3.79 (s, 3H), 3.8-4.2 (v br m, 4H), 6.72-6.76 (m, 2H), 7.17-7.24 (br m, 1H), 7.67 (s, 1H), 7.78 (s, 1H).

Example 9

[4-(Methylamino)-5-{1-methyl-5-[4-(trifluoromethyl)phenyl]-1H-pyrazol-4-yl}imidazo[5,1-f][1,2,4]triazin-7-yl]methanol

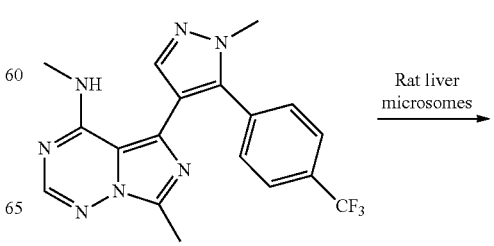

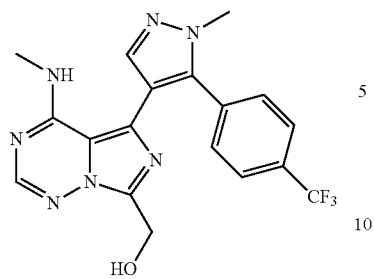

N,7-Dimethyl-5-{1-methyl-5-[4-(trifluoromethyl)phenyl]-1H-pyrazol-4-yl}imidazo[5,1-f][1,2,4]triazin-4-amine, at a substrate concentration of 50 μM, was incubated for 1 hour with rat liver microsomes and NADPH (1 mM) (21.1 mg/mL protein concentration; 25 mL incubation volume). Incubations were extracted with 4 volumes of acetonitrile. Following centrifugation at 3400 rpm, the supernatant was evaporated at 25° C. in a Turbovap. The residue was reconstituted with 5% aqueous acetonitrile and subjected to preparative reverse-phase HPLC purification (Column: Zorbax Rx-C8 [Agilent], 250×9.6 mm, 5 μm; Mobile phase A: aqueous 5 mM ammonium formate, pH 3; Mobile phase B: acetonitrile; Gradient: 10% to 90% B; UV detection at 254 mm). The fractions containing the M+16 metabolite were dried down to provide the product as a solid. MS m/z 404 (M+H). $^1$H NMR (600 MHz, DMSO-$d_6$) δ 2.71 (d, J=4.8 Hz, 3H), 3.86 (s, 3H), 4.69 (s, 2H), 6.68 (br q, J=4.7 Hz, 1H), 7.55 (d, J=8.0 Hz, 2H), 7.70 (s, 1H), 7.76 (d, J=8.0 Hz, 2H), 7.85 (s, 1H).

Example 10

7-Methyl-N-(methyl-$d_3$)-5-{1-methyl-5-[4-(trifluoromethyl)phenyl]-1H-pyrazol-4-yl}imidazo[5,1-f][1,2,4]triazin-4-amine

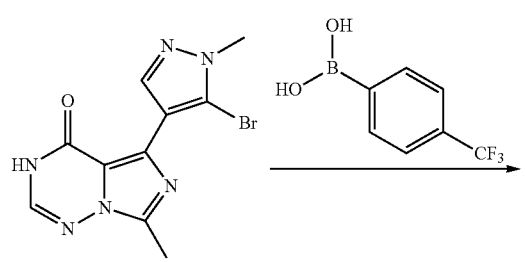

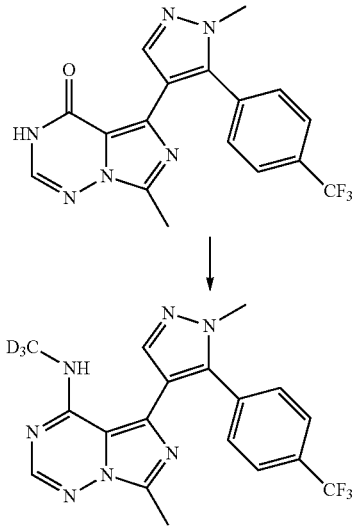

Step 1. Synthesis of 7-methyl-5-{1-methyl-5-[4-(trifluoromethyl)phenyl]-1H-pyrazol-4-yl}imidazo[5,1-f][1,2,4]triazin-4(3H)-one 5-(5-Bromo-1-methyl-1H-pyrazol-4-yl)-7-methylimidazo[5,1-f][1,2,4]triazin-4(3H)-one (200 mg, 0.647 mmol), [4-(trifluoromethyl)phenyl]boronic acid (96%, 128 mg, 0.647 mmol), tetrakis(triphenylphosphine)palladium(0) (60.1 mg, 0.052 mmol) and sodium carbonate (206 mg, 1.94 mmol) were combined in ethanol (4 mL) and subjected to microwave irradiation at 130° C. for 45 minutes, then heated at 100° C. for 18 hours. The solvent was removed in vacuo, and the residue was partitioned between ethyl acetate and water. The aqueous layer was extracted three times with ethyl acetate, and the combined organic layers were concentrated in vacuo and purified via silica gel chromatography (Gradient: 50% to 100% [5% methanol/5% triethylamine/90% ethyl acetate] in heptane) to provide the product. Yield: 90 mg, 0.24 mmol, 37%. LCMS m/z 375.4 (M+1). $^1$H NMR (400 MHz, CD$_3$OD) δ 2.47 (s, 3H), 3.84 (s, 3H), 7.56 (br d, J=8 Hz, 2H), 7.63 (s, 1H), 7.71 (br d, J=8 Hz, 2H), 7.98 (s, 1H).

Step 2. Synthesis of 7-methyl-N-methyl-$d_3$)-5-{1-methyl-5-[4-(trifluoromethyl)phenyl]-1H-pyrazol-4-yl}imidazo[5,1-f][1,2,4]triazin-4-amine 7-Methyl-5-{1-methyl-5-[4-(trifluoromethyl)phenyl]-1H-pyrazol-4-yl}imidazo[5,1-f][1,2,4]triazin-4(3H)-one was converted to the product according to the general procedure for the synthesis of 4-(azetidin-1-yl)-7-methyl-5-(1-methyl-1H-pyrazol-4-yl)imidazo[1,5-f][1,2,4]triazine in Example 2, except that methyl-$d_3$-amine was used in place of azetidine hydrochloride. In this case, the reaction was worked up via removal of solvent in vacuo, followed by addition of water and extraction with ethyl acetate. The combined organic layers were concentrated under reduced pressure and purified using silica gel chromatography (Gradient: 0% to 100% [5% methanol/5% triethylamine/90% ethyl acetate] in heptane) to afford the product as a gummy oil. Yield: 20 mg, 0.051 mmol, 42%. LCMS m/z 391.4 (M+1). $^1$H NMR (400 MHz, CD$_3$OD)

δ 2.57 (s, 3H), 3.94 (s, 3H), 7.51 (br d, J=8.1 Hz, 2H), 7.70 (br d, J=8.2 Hz, 2H), 7.75 (s, 1H), 7.79 (s, 1H)

Example 11

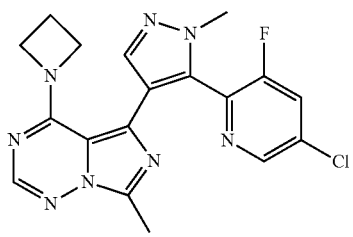 [SMILES: Cc1nc(-c2cnn(C)c2-c2ncc(Cl)cc2F)c2c(N3CCC3)ncnn12]

4-(Azetidin-1-yl)-5-[5-(5-chloro-3-fluoropyridin-2-yl)-1-methyl-1H-pyrazol-4-yl]-7-methylimidazo[5,1-f][1,2,4]triazine Step 1. Synthesis of 5-chloro-3-fluoro-2-(trimethylstannyl)pyridine 2,5-Dichloro-3-fluoropyridine (98%, 254 mg, 1.50 mmol) was dissolved in anhydrous 1,4-dioxane (10 mL) in a sealable tube. Hexamethyldistannane (99%, 0.346 mL, 1.65 mmol), dichlorobis(triphenylphosphine)palladium(II) (99%, 138 mg, 0.195 mmol) and triphenylarsine (97%, 47.4 mg, 0.150 mmol) were added; the tube was then flushed with nitrogen, sealed and heated at 80° C. for 16 hours. After cooling, the reaction mixture was concentrated in vacuo and the residue was chromatographed twice on basic alumina (Gradient: 0% to 20% ethyl acetate in heptane), affording the product. Yield: 390 mg, 1.32 mmol, 88%. LCMS m/z 296.0 (M+1). $^1$H NMR (400 MHz, CDCl$_3$) δ 0.34-0.49 (m, 9H), 7.29 (dd, J=6.5, 1.9 Hz, 1H), 8.59 (dd, J=2.0, 2.0 Hz, 1H).

Step 2. Synthesis of 4-(azetidin-1-yl)-5-[5-(5-chloro-3-fluoropyridin-2-yl)-1-methyl-1H-pyrazol-4-yl]-7-methylimidazo[5,1-f][1,2,4]triazine 4-(Azetidin-1-yl)-5-(5-bromo-1-methyl-1H-pyrazol-4-yl)-7-methylimidazo[5,1-f][1,2,4]triazine (35 mg, 0.10 mmol) and 5-chloro-3-fluoro-2-(trimethylstannyl)pyridine (59.5 mg, 0.202 mmol) were combined in toluene (1 mL) in a sealable tube and treated with dichlorobis(triphenylphosphine)palladium(II) (99%, 3.50 mg, 0.0050 mmol). The tube was sealed, and the reaction mixture was heated at 120° C. for 24 hours. The reaction was cooled, filtered through Celite and the pad was washed with ethyl acetate. After removal of solvent from the filtrate under reduced pressure, the residue was purified via silica gel chromatography (Eluant: 1% methanol in ethyl acetate) to provide the product as a solid. Yield: 20 mg, 0.050 mmol, 50%. LCMS m/z 399.1 (M+1). $^1$H NMR (400 MHz, CDCl$_3$) δ 2.21-2.30 (m, 2H), 2.59 (s, 3H), 3.86-4.14 (br m, 4H), 3.98 (s, 3H), 7.40 (dd, J=9.0, 2.0 Hz, 1H), 7.72 (s, 1H), 7.80 (s, 1H), 8.51-8.53 (m, 1H).

Example 12

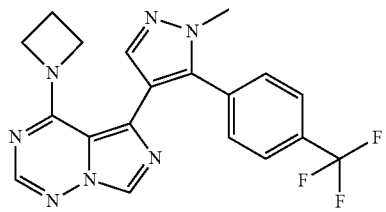 [SMILES: Cn1ncc(-c2ncn3ncnc(N4CCC4)c23)c1-c1ccc(C(F)(F)F)cc1]

4-(Azetidin-1-yl)-5-{1-methyl-5-[4-(trifluoromethyl)phenyl]-1H-pyrazol-4-yl}imidazo[5,1-f][1,2,4]triazine, trifluoroacetate salt Step 1. Synthesis of methyl 2-{[(4-methoxybenzyl)amino]methylene}hydrazine carboxylate Methyl 2-(ethoxymethylene)hydrazinecarboxylate (prepared according to the method of N. Shao et al., Tetrahedron Lett. 2006, 47, 6743-6746; 5.00 g, 34.2 mmol) and 4-methoxybenzylamine (4.44 mL, 34.2 mmol) were dissolved in ethanol (20 mL), and the reaction was heated to 50° C. for 2 hours, then allowed to stir at room temperature for 18 hours. Filtration provided the product as a solid. Yield: 4.80 g, 20.2 mmol, 59%. $^1$H NMR (400 MHz, CD$_3$OD) δ 3.69 (br s, 3H), 3.78 (s, 3H), 4.27 (br s, 2H), 6.80 and 7.62 (2 br s, 1H), 6.89 (br d, J=8.5 Hz, 2H), 7.19-7.28 (br m, 2H).

Step 2. Synthesis of methyl 2-[2-(5-bromo-1-methyl-1H-pyrazol-4-yl)-2-oxoethyl]-2-formylhydrazinecarboxylate Methyl 2-{[(4-methoxybenzyl)amino]methylene}hydrazinecarboxylate (3.28 g, 13.8 mmol), 2-bromo-1-(5-bromo-1-methyl-1H-pyrazol-4-yl)ethanone (3.90 g, 13.8 mmol) and sodium carbonate (1.16 g, 13.8 mmol) were combined in a mixture of N,N-diisopropylethylamine (99.5%, 2.30 mL, 13.8 mmol) and acetonitrile (30 mL). The reaction was heated at 80° C. for 18 hours, at which time water was added, and heated was continued for 10 minutes. After removal of solvent in vacuo, the aqueous residue was partitioned between water and ethyl acetate (100 mL). The aqueous layer was extracted with ethyl acetate (4×100 mL), and the combined organic layers were dried over sodium sulfate, filtered, and concentrated under reduced pressure. Purification using silica gel chromatography (Gradient: 0% to 100% ethyl acetate in heptane) provided the product (1.20 g), contaminated with some impurities. This material was taken directly to the following step. LCMS m/z 319.0 (M+1). $^1$H NMR (400 MHz, CD$_3$OD) δ, product peaks: 3.74 (s, 3H), 3.92 (s, 3H), 4.82 (br s, 2H), 8.14 (s, 1H), 8.24 (s, 1H).

Step 3. Synthesis of methyl [4-(5-bromo-1-methyl-1H-pyrazol-4-yl)-1H-imidazol-1-yl]carbamate Methyl 2-[2-(5-bromo-1-methyl-1H-pyrazol-4-yl)-2-oxoethyl]-2-formylhydrazine carboxylate (1.20 g, 3.76 mmol) was mixed with ammonium acetate (1.16 g, 15.0 mmol), formamide (4 mL) and acetonitrile (5 mL). The reaction was heated to 130° C., and the acetonitrile was allowed to boil off for 10 minutes. Heating was continued for an additional 4 hours. After addition of water, the crude mixture was extracted eight times with ethyl acetate. The combined organic layers were dried over sodium sulfate, filtered and concentrated in vacuo; purification via silica gel chromatography (Gradient: 0% to 100% [10% methanol in ethyl acetate] in heptane) afforded the product as a pinkish solid. Yield: 800 mg, 2.67 mmol, 19% over two steps. LCMS m/z 299.8 (M+1). $^1$H NMR (400 MHz, CD$_3$OD) δ 3.80 (br s, 3H), 3.90 (s, 3H), 7.52 (d, J=1.3 Hz, 1H), 7.77 (d, J=1.3 Hz, 1H), 7.85 (s, 1H).

Step 4. Synthesis of 4-(5-bromo-1-methyl-1H-pyrazol-4-yl)-1H-imidazol-1-amine

A mixture of methyl [4-(5-bromo-1-methyl-1H-pyrazol-4-yl)-1H-imidazol-1-yl]carbamate (400 mg, 1.33 mmol) and aqueous sodium hydroxide solution (1 M, 1.33 mL, 1.33 mmol) was heated at 100° C. for 18 hours. After cooling, the aqueous mixture was extracted five times with 2-butanol, and the combined organic layers were dried over sodium sulfate, filtered and concentrated in vacuo to provide the product as a beige solid. Yield: 310 mg, 1.28 mmol, 96%. $^1$H NMR (400 MHz, CD$_3$OD) δ 3.89 (s, 3H), 7.46 (d, J=1.2 Hz, 1H), 7.61 (d, J=1.3 Hz, 1H), 7.82 (s, 1H).

Step 5. Synthesis of 5-(5-bromo-1-methyl-1H-pyrazol-4-yl)imidazo[5,1-f][1,2,4]triazin-4(3H)-one Formamidine acetate (98%, 132 mg, 1.24 mmol) and 4-(5-bromo-1-methyl-1H-pyrazol-4-yl)-1H-imidazol-1-amine (300 mg, 1.24 mmol) were combined in 2-butanol (10 mL) and heated at 110° C. for 3 hours. Additional formamidine acetate (98%, 132 mg, 1.24 mmol) was added, and heating was continued for an additional 18 hours. After the reaction cooled, water and ethyl acetate were added. The aqueous layer was extracted twice with ethyl acetate, and the combined organic layers were dried over sodium sulfate, filtered and concentrated in vacuo to provide the intermediate amidine as a white solid (260 mg, 0.966 mmol). LCMS m/z 269.1 (M+1). This was dissolved in 1,4-dioxane (4 mL) and treated with 1,1'-carbonylbis(1H-1,2,4-triazole) (212 mg, 1.16 mmol); the reaction was heated at 70° C. for 18 hours, then concentrated under reduced pressure. After addition of dichloromethane and methanol to the residue, the mixture was filtered, and the filtrate was applied to a silica gel column and eluted (Gradient: 0% to 100% [90:5:5 ethyl acetate/triethylamine/methanol] in heptane) to afford the product. Yield: 55 mg, 0.19 mmol, 19%. LCMS m/z 295.0 (M+1). $^1$H NMR (400 MHz, CD$_3$OD) δ 3.95 (s, 3H), 7.73 (s, 1H), 8.10 (s, 1H), 8.34 (s, 1H).

Step 6. Synthesis of 4-(azetidin-1-yl)-5-(5-bromo-1-methyl-1H-pyrazol-4-yl)imidazo[5,1-f][1,2,4]triazine (C8)

Phosphorus oxychloride (0.046 mL, 0.503 mmol) was added to a mixture of 5-(5-bromo-1-methyl-1H-pyrazol-4-yl)imidazo[5,1-f][1,2,4]triazin-4(3H)-one (50 mg, 0.17 mmol) in toluene (1 mL). After addition of N,N-diisopropylethylamine (99.5%, 0.149 mL, 0.84 mmol), the reaction was allowed to stir at room temperature for 18 hours. After removal of solvent in vacuo, the residue was dissolved in dichloromethane and treated with azetidine (0.023 mL, 0.34 mmol). After 66 hours, the reaction was concentrated under reduced pressure and the residue was purified by silica gel chromatography (Gradient: 0% to 10% methanol in ethyl acetate) to provide C8. Yield: 25 mg, 0.075 mmol, 44%. LCMS m/z 336.1 (M+1). $^1$H NMR (400 MHz, CD$_3$OD) δ 2.26-2.34 (m, 2H), 3.5-4.4 (v br m, 4H), 3.97 (s, 3H), 7.70 (s, 1H), 7.84 (s, 1H), 8.47 (s, 1H).

Step 7. Synthesis of 4-(azetidin-1-yl)-5-{1-methyl-5-[4-(trifluoromethyl)phenyl]-1H-pyrazol-4-yl}imidazo[5,1-f][1,2,4]triazine, trifluoroacetate salt 4-(Azetidin-1-yl)-5-(5-bromo-1-methyl-1H-pyrazol-4-yl)imidazo[5,14][1,2,4]triazine (15 mg, 0.045 mmol), [4-(trifluoromethyl)phenyl]boronic acid (9.50 mg, 0.0500 mmol), tetrakis(triphenylphosphine)palladium(0) (4.6 mg, 0.0040 mmol) and sodium carbonate (9.5 mg, 0.090 mmol) were combined in ethanol (4 mL), and the reaction mixture was heated at reflux for 18 hours. After filtration, the filtrate was concentrated in vacuo and purified via reversed-phase HPLC (Column: Waters Sunfire C18, 19×100 mm, 5 µm; Mobile phase A: 0.05% TFA in water (v/v); Mobile phase B: 0.05% TFA in acetonitrile (v/v); Gradient: 5% to 100% B). Yield: 4.5 mg, 0.011 mmol, 24%. Retention time: 2.32 minutes (Column: Waters Atlantis dC18, 4.6×50 mm, 5 µm; Mobile phase A: 0.05% TFA in water (v/v); Mobile phase B: 0.05% TFA in acetonitrile (v/v); Gradient: linear, 5% to 95% B over 4.0 minutes; Flow rate: 2 mL/minute). LCMS m/z 400.2 (M+1).

Method A

Suzuki reaction under microwave conditions: alternate synthesis of N,7-dimethyl-5-{1-methyl-5-[4-(trifluoromethyl)phenyl]-1H-pyrazol-4-yl}imidazo[5,1-f][1,2,4]triazin-4-amine

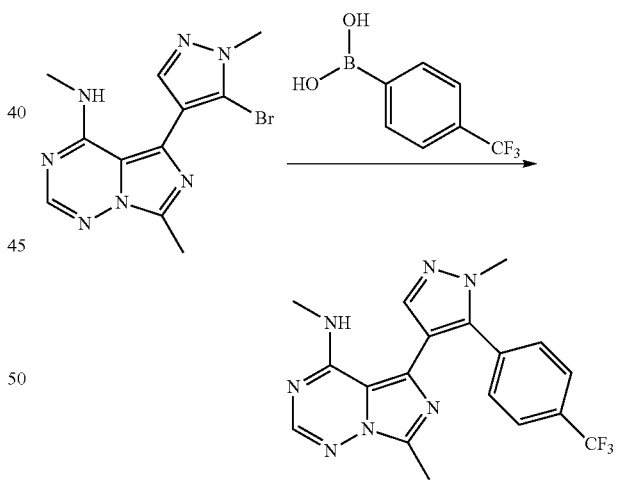

5-(5-Bromo-1-methyl-1H-pyrazol-4-yl)-N,7-dimethylimidazo[5,1-f][1,2,4]triazin-4-amine (500 mg, 1.55 mmol), [4-(trifluoromethyl)phenyl]boronic acid (590 mg, 3.11 mmol), sodium carbonate (329 mg, 3.10 mmol), tetrakis (triphenylphosphine)palladium(0) (179 mg, 0.155 mmol) and ethanol (10 mL) were combined in a microwave vessel. The reaction was subjected to microwave irradiation at 130° C. for 45 minutes at 200 W. The reaction was dried over sodium sulfate, filtered and concentrated in vacuo. Purification via silica gel chromatography (Eluant: 20% tetrahydrofuran in dichloromethane) provided the product as a light yellow solid. Yield: 423 mg, 1.13 mmol, 73%. LCMS m/z 388.2 (M+1). ¹H NMR (400 MHz, CDCl₃) δ 2.62 (s, 3H), 2.99 (d, J=4.9 Hz, 3H), 3.96 (s, 3H), 5.46-5.53 (m, 1H), 7.60 (br AB quartet, $J_{AB}$=8 Hz, $\Delta v_{AB}$=48 Hz, 4H), 7.73 (s, 1H), 7.90 (s, 1H).

Method B

Fluorination of carbonyl group: alternate synthesis of 5-{5-[4-(difluoromethyl)phenyl]-1-methyl-1H-pyrazol-4-yl}-N,7-dimethylimidazo[5,1-f][1,2,4]triazin-4-amine

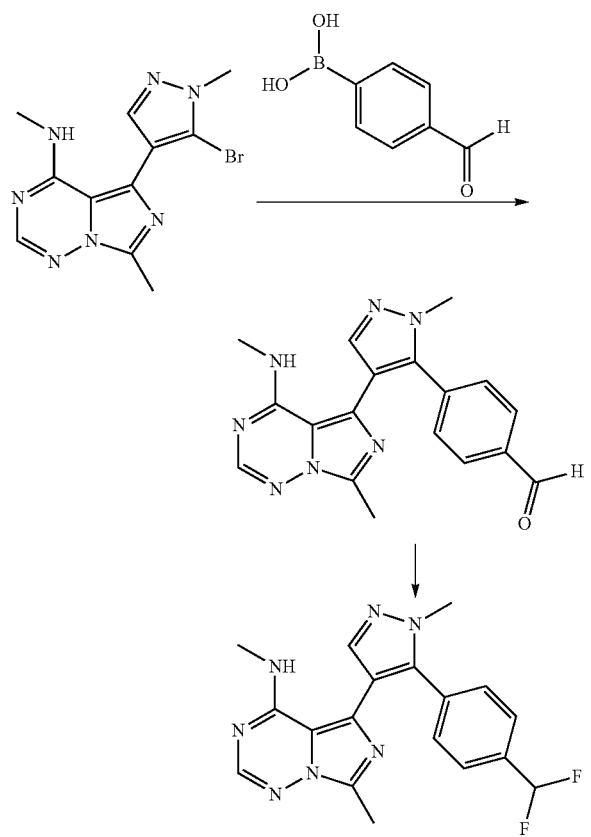

Step 1. Synthesis of 4-{1-methyl-4-[7-methyl-4-(methylamino)imidazo[5,1-f][1,2,4]triazin-5-yl]-1H-pyrazol-5-yl}benzaldehyde 5-Bromo-1-methyl-1H-pyrazol-4-yl)-N,7-dimethylimidazo[5,1-f][1,2,4]triazin-4-amine (1.18 g, 3.66 mmol), (4-formylphenyl)boronic acid (604 mg, 4.03 mmol), tetrakis(triphenylphosphine)palladium(0) (423 mg, 0.366 mmol) and sodium carbonate (776 mg, 7.32 mmol) were combined in ethanol (20 mL), and the reaction mixture was heated at reflux for 18 hours. After cooling, solvent was removed in vacuo, and the residue was partitioned between ethyl acetate and water. The organic layer was dried over sodium sulfate, filtered, and concentrated under reduced pressure. Purification via silica gel chromatography (Gradient: 0% to 100% [18:1:1 ethyl acetate/methanol/triethylamine] in heptane) provided the crude product (900 mg), which was taken directly to the next step. LCMS m/z 348.2 (M+1). ¹H NMR (400 MHz, CD₃OD), product peaks only: δ 2.57 (s, 3H), 2.82 (s, 3H), 3.95 (s, 3H), 7.51 (br d, J=8.2 Hz, 2H), 7.75 (s, 1H), 7.78 (s, 1H), 7.92 (br d, J=8.5 Hz, 2H), 9.98 (s, 1H).

Step 2. Synthesis of 5-{5-[4-(difluoromethyl)phenyl]-1-methyl-1H-pyrazol-4-yl}-N,7-dimethylimidazo[5,1-f][1,2,4]triazin-4-amine 4-{1-Methyl-4-[7-methyl-4-(methylamino)imidazo[5,1-f][1,2,4]triazin-5-yl]-1H-pyrazol-5-yl}benzaldehyde (from the previous step, 900 mg) was dissolved in dichloromethane (8.6 mL) and treated with (diethylamino)sulfur trifluoride (0.34 mL, 2.6 mmol). After the reaction had stirred for 18 hours, additional (diethylamino)sulfur trifluoride (0.40 mL, 3.0 mmol) was added, and stirring was continued for 3 hours. One more charge of (diethylamino)sulfur trifluoride (0.40 mL, 3.0 mmol) was followed by 1 hour of stirring. The reaction was then diluted with dichloromethane and aqueous sodium bicarbonate solution, and the aqueous layer was extracted with ethyl acetate (4×400 mL). The combined organic layers were dried over sodium sulfate, filtered and concentrated in vacuo; purification via silica gel chromatography (Gradient: 0% to 100% {18:1:1 ethyl acetate/methanol/triethylamine} in heptane) provided the product as a beige foam. Yield: 370 mg, 1.00 mmol, 27% over 2 steps. LCMS m/z 370.1 (M+1). ¹H NMR (400 MHz, CD₃OD) δ 2.57 (s, 3H), 2.82 (s, 3H), 3.93 (s, 3H), 6.76 (t, J=56.1 Hz, 1H), 7.50 (br AB quartet, $J_{AB}$=8 Hz, $\Delta v_{AB}$=54 Hz, 4H), 7.74 (s, 1H), 7.78 (s, 1H).

TABLE 1

| Ex No | Structure | Method of Prep; starting material | IUPAC Name | ¹H NMR (400 MHz, CDCl₃), δ (ppm); LCMS, observed ion m/z (M + 1) or HPLC retention time (minutes); MS observed ion m/z (M + 1) (unless otherwise indicated) |
|---|---|---|---|---|
| 13 | 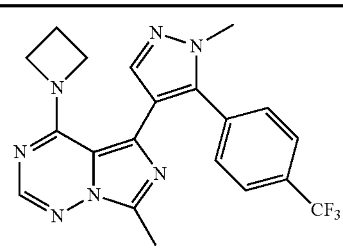 | Ex 1 | 4-(azetidin-1-yl)-7-methyl-5-{1-methyl-5-[4-(trifluoromethyl)phenyl]-1H-pyrazol-4-yl}imidazo[5,1-f][1,2,4]triazine | 2.22-2.31 (m, 2H), 2.64 (s, 3H), 3.5-4.4 (v br m, 4H), 3.93 (s, 3H), 7.55 (br d, J = 8 Hz, 2H), 7.65 (br d, J = 8 Hz, 2H), 7.67 (s, 1H), 7.82 (s, 1H); 414.5 |

TABLE 1-continued

| Ex No | Structure | Method of Prep; starting material | IUPAC Name | $^1$H NMR (400 MHz, CDCl$_3$), δ (ppm); LCMS, observed ion m/z (M + 1) or HPLC retention time (minutes); MS observed ion m/z (M + 1) (unless otherwise indicated) |
|---|---|---|---|---|
| 14 | 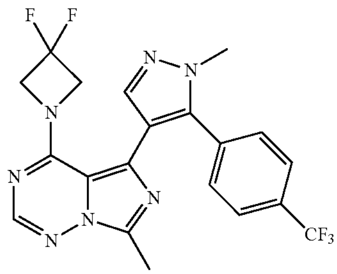 [SMILES: Cc1nc(-c2cnn(C)c2-c2ccc(C(F)(F)F)cc2)c2c(N3CC(F)(F)C3)ncnn12] | Ex 1 | 4-(3,3-difluoroazetidin-1-yl)-7-methyl-5-{1-methyl-5-[4-(trifluoromethyl)phenyl]-1H-pyrazol-4-yl}imidazo[5,1-f][1,2,4]triazine | 2.68 (s, 3H), 3.96 (s, 3H), 4.08-4.21 (br m, 4H), 7.53 (br d, J = 8 Hz, 2H) 7.66 (br d, J = 8 Hz, 2H), 7.71 (s, 1H), 7.87 (s, 1H); 450.5 |
| 15 | 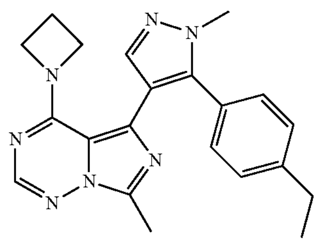 [SMILES: CCc1ccc(-c2c(-c3nc(C)n4ncnc(N5CCC5)c34)cnn2C)cc1] | Ex 2$^1$; C2 | 4-(azetidin-1-yl)-5-[5-(4-ethylphenyl)-1-methyl-1H-pyrazol-4-yl]-7-methylimidazo[5,1-f][1,2,4]triazine | $^1$H NMR (500 MHz, CDCl$_3$): 1.22 (t, J = 7.6 Hz, 3H), 2.19-2.26 (m, 2H), 2.63 (s, 3H), 2.64 (q, J = 7.7 Hz, 2H), 3.5-3.9 (v br m, 2H), 3.90 (s, 3H), 3.9-4.3 (v br m, 2H), 7.18 (br d, J = 8.3 Hz, 2H), 7.27 (br d, J = 8.2 Hz, 2H), 7.62 (s, 1H), 7.77 (s, 1H); 374.1 |
| 16 | 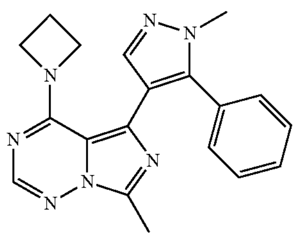 [SMILES: Cc1nc(-c2cnn(C)c2-c2ccccc2)c2c(N3CCC3)ncnn12] | Ex 2$^1$; C2 | 4-(azetidin-1-yl)-7-methyl-5-(1-methyl-5-phenyl-1H-pyrazol-4-yl)imidazo[5,1-f][1,2,4]triazine | $^1$H NMR (500 MHz, CDCl$_3$): 2.20-2.27 (m, 2H), 2.63 (s, 3H), 3.5-3.9 (v br m, 2H), 3.91 (s, 3H), 3.9-4.3 (v br m, 2H), 7.32-7.38 (m, 5H), 7.65 (s, 1H), 7.77 (s, 1H); 346.1 |
| 17 | 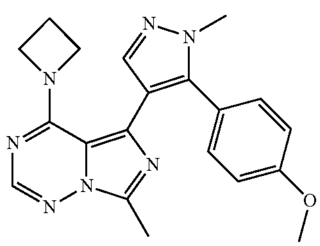 [SMILES: COc1ccc(-c2c(-c3nc(C)n4ncnc(N5CCC5)c34)cnn2C)cc1] | Ex 2; C2 | 4-(azetidin-1-yl)-5-[5-(4-methoxyphenyl)-1-methyl-1H-pyrazol-4-yl]-7-methylimidazo[5,1-f][1,2,4]triazine | 2.17-2.27 (m, 2H), 2.61 (s, 3H), 3.5-4.3 (v br m, 4H), 3.77 (s, 3H), 3.87 (s, 3H), 6.86 (br d, J = 8.8 Hz, 2H), 7.27 (br d, J = 8.8 Hz, 2H), 7.61 (s, 1 H), 7.76 (s, 1 H); 376.1 |
| 18 | 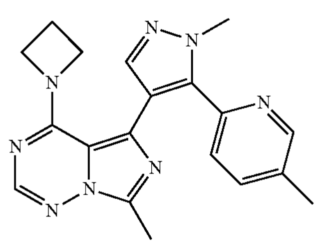 [SMILES: Cc1ccc(-c2c(-c3nc(C)n4ncnc(N5CCC5)c34)cnn2C)nc1] | Ex 2$^1$; C2 | 4-(azetidin-1-yl)-7-methyl-5-[1-methyl-5-(5-methylpyridin-2-yl)-1H-pyrazol-4-yl]imidazo[5,1-f][1,2,4]triazine | 2.15-2.24 (m, 2H), 2.34 (br s, 3H), 2.69 (s, 3H), 3.5-3.8 (v br m, 2H), 3.9-4.2 (v br m, 2H), 4.11 (s, 3H), 7.25-7.28 (m, 1H, assumed; partially obscured by solvent peak), 7.34-7.38 (m, 1H), 7.64 (s, 1H), 7.78 (s, 1H), 8.51-8.53 (br s, 1H); 361.5 |
| 19 | 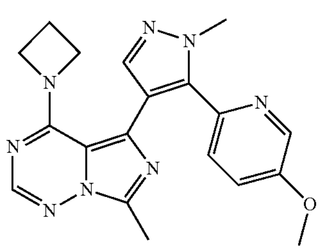 [SMILES: COc1ccc(-c2c(-c3nc(C)n4ncnc(N5CCC5)c34)cnn2C)nc1] | Ex 2$^1$; C2 | 4-(azetidin-1-yl)-5-[5-(5-methoxypyridin-2-yl)-1-methyl-1H-pyrazol-4-yl]-7-methylimidazo[5,1-f][1,2,4]triazine | 2.16-2.24 (m, 2H), 2.69 (s, 3H), 3.5-3.8 (v br m, 2H), 3.85 (s, 3H), 3.9-4.2 (v br m, 2H), 4.09 (s, 3H), 7.05 (dd, J = 8.7, 3.0 Hz, 1 H), 7.32 (d, J = 8.8 Hz, 1H), 7.63 (s, 1H), 7.78 (s, 1H), 8.38 (d, J = 2.9 Hz, 1 H); 377.5 |

TABLE 1-continued

| Ex No | Structure | Method of Prep; starting material | IUPAC Name | $^{1}$H NMR (400 MHz, CDCl$_3$), δ (ppm); LCMS, observed ion m/z (M + 1) or HPLC retention time (minutes); MS observed ion m/z (M + 1) (unless otherwise indicated) |
|---|---|---|---|---|
| 20 | 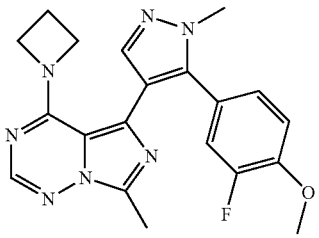 [SMILES: COc1ccc(-c2c(-c3nc(C)n4ncnc(N5CCC5)c34)cnn2C)cc1F] | Ex 2[1]; C2 | 4-(azetidin-1-yl)-5-[5-(3-fluoro-4-methoxyphenyl)-1-methyl-1H-pyrazol-4-yl]-7-methylimidazo[5,1-f][1,2,4]triazine | 2.24-2.32 (m, 2H), 2.66 (s, 3H), 3.5-3.9 (v br m, 2H), 3.90 (s, 3H), 3.91 (s, 3H), 3.9-4.3 (v br m, 2H), 6.95 (dd, J = 8.9, 8.5 Hz, 1H), 7.09-7.15 (m, 2H), 7.63 (s, 1H), 7.83 (s, 1H); APCl m/z 394.2 (M + 1) |
| 21 | 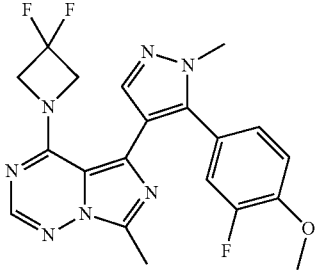 [SMILES: COc1ccc(-c2c(-c3nc(C)n4ncnc(N5CC(F)(F)C5)c34)cnn2C)cc1F] | Ex 2[1]; C1 | 4-(3,3-difluoroazetidin-1-yl)-5-[5-(3-fluoro-4-methoxyphenyl)-1-methyl-1H-pyrazol-4-yl]-7-methylimidazo[5,1-f][1,2,4]triazine | 2.68 (s, 3H), 3.90 (s, 3H), 3.93 (s, 3H), 4.07-4.24 (br m, 4H), 6.95 (dd, J = 8.6, 8.4 Hz, 1H), 7.07 (ddd, J = 8.5, 2.1, 1.2 Hz, 1H), 7.13 (dd, J = 11.7, 2.1 Hz, 1H), 7.67 (s, 1H), 7.86 (s, 1 H) |
| 22 | 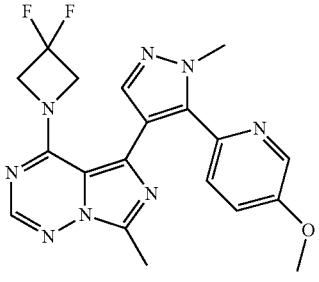 [SMILES: COc1ccc(-c2c(-c3nc(C)n4ncnc(N5CC(F)(F)C5)c34)cnn2C)nc1] | Ex 2[1]; C1 | 4-(3,3-difluoroazetidin-1-yl)-5-[5-(5-methoxypyridin-2-yl)-1-methyl-1H-pyrazol-4-yl]-7-methylimidazo[5,1-f][1,2,4]triazine | 2.71 (s, 3H), 3.86 (s, 3H), 4.09 (s, 3H), 4.07-4.23 (br m, 4H), 7.06 (dd, J = 8.7, 3.0 Hz, 1H), 7.27-7.29 (m, 1H, assumed; partially obscured by solvent peak), 7.66 (s, 1H), 7.84 (s, 1 H), 8.39 (br d, J = 3.0 Hz, 1H); 413.5 |
| 23 | 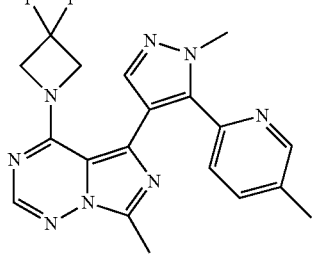 | Ex 2[1]; C1 | 4-(3,3-difluoroazetidin-1-yl)-7-methyl-5-[1-methyl-5-(5-methylpyridin-2-yl)-1H-pyrazol-4-yl]imidazo[5,1-f][1,2,4]triazine | 2.34 (s, 3H), 2.71 (s, 3H), 4.05-4.22 (v br m, 4H), 4.10 (s, 3H), 7.24-7.27 (m, 1H, assumed; partially obscured by solvent peak), 7.36-7.40 (m, 1H), 7.67 (s, 1H), 7.84 (s, 1H), 8.52-8.54 (m, 1H); 397.5 |
| 24 | 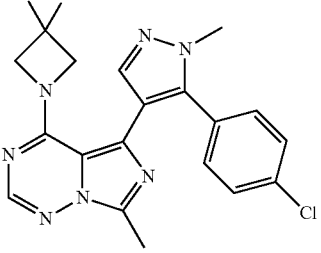 | Ex 2[1]; C1 | 5-[5-(4-chlorophenyl)-1-methyl-1H-pyrazol-4-yl]-4-(3,3-difluoroazetidin-1-yl)-7-methylimidazo[5,1-f][1,2,4]triazine | 2.67 (s, 3H), 3.93 (s, 3H), 4.06-4.22 (br m, 4H), 7.33 (br AB quartet, $J_{AB}$ = 8.8 Hz, $\Delta v_{AB}$ = 26.4 Hz, 4H), 7.69 (s, 1H), 7.86 (s, 1H); APCl m/z 416.3, 418.4 (M + 1) |

TABLE 1-continued

| Ex No | Structure | Method of Prep; starting material | IUPAC Name | $^1$H NMR (400 MHz, CDCl$_3$), δ (ppm); LCMS, observed ion m/z (M + 1) or HPLC retention time (minutes); MS observed ion m/z (M + 1) (unless otherwise indicated) |
|---|---|---|---|---|
| 25 | 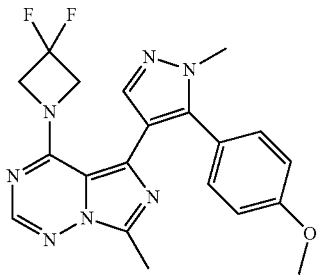 [SMILES: COc1ccc(-c2c(-c3nc(C)n4ncnc(N5CC(F)(F)C5)c34)cnn2C)cc1] | Ex 2[1]; C1 | 4-(3,3-difluoroazetidin-1-yl)-5-[5-(4-methoxyphenyl)-1-methyl-1H-pyrazol-4-yl]-7-methylimidazo[5,1-f][1,2,4]triazine | 2.68 (s, 3H), 3.81 (s, 3H), 3.92 (s, 3H), 4.03-4.24 (br m, 4H), 6.89 (br d, J = 8.9 Hz, 2H), 7.25 (br d, J = 9.0 Hz, 2H), 7.68 (s, 1H), 7.83 (s, 1H); APCl m/z 412.4 (M + 1) |
| 26 | 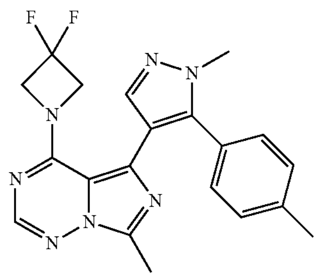 [SMILES: Cc1ccc(-c2c(-c3nc(C)n4ncnc(N5CC(F)(F)C5)c34)cnn2C)cc1] | Ex 2[1]; C1 | 4-(3,3-difluoroazetidin-1-yl)-7-methyl-5-[1-methyl-5-(4-methylphenyl)-1H-pyrazol-4-yl]imidazo[5,1-f][1,2,4]triazine | 2.35(br s, 3H), 2.68 (s, 3H), 3.93 (s, 3H), 4.03-4.25 (br m, 4H), 7.19 (br AB quartet, J$_{AB}$ = 8 Hz, Δν$_{AB}$ = 16 Hz, 4H), 7.68 (s, 1H), 7.83 (s, 1H); 396.1 |
| 27 | 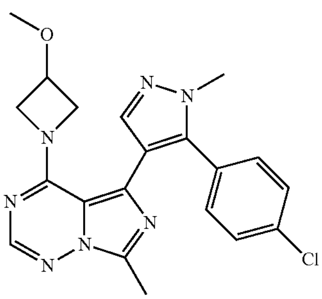 [SMILES: COC1CN(c2ncnn3c(C)nc(-c4cnn(C)c4-c4ccc(Cl)cc4)c23)C1] | Ex 2[1]; C1 | 5-[5-(4-chlorophenyl)-1-methyl-1H-pyrazol-4-yl]-4-(3-methoxyazetidin-1-yl)-7-methylimidazo[5,1-f][1,2,4]triazine | $^1$H NMR (500 MHz, CDCl$_3$), characteristic peaks: 2.64 (s, 3H), 3.25 (s, 3H), 3.91 (s, 3H), 7.33 (AB quartet, J$_{AB}$ = 8.5 Hz, Δν$_{AB}$ = 22.5 Hz, 4H), 7.66 (s, 1H), 7.81 (s, 1H); 410.6 |
| 28 | 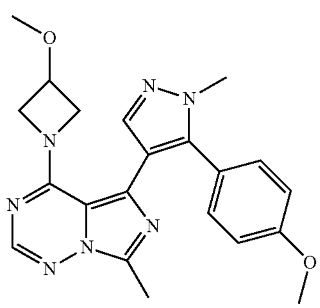 [SMILES: COc1ccc(-c2c(-c3nc(C)n4ncnc(N5CC(OC)C5)c34)cnn2C)cc1] | Ex 2[1]; C1 | 4-(3-methoxyazetidin-1-yl)-5-[5-(4-methoxyphenyl)-1-methyl-1H-pyrazol-4-yl]-7-methylimidazo[5,1-f][1,2,4]triazine | $^1$H NMR (500 MHz, CDCl$_3$), characteristic peaks: 2.65 (s, 3H), 3.25 (s, 3H), 3.80 (s, 3H), 3.90 (s, 3H), 4.09-4.12 (m, 1H), 6.88 (br d, J = 8.8 Hz, 2H), 7.26-7.28 (m, 2H, assumed; partially obscured by solvent peak), 7.65 (s, 1H), 7.79 (s, 1H); 406.6 |
| 29 | 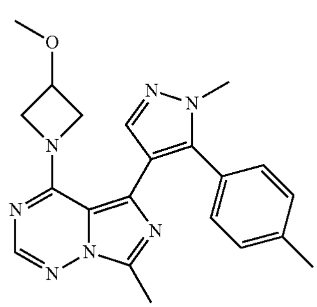 [SMILES: COC1CN(c2ncnn3c(C)nc(-c4cnn(C)c4-c4ccc(C)cc4)c23)C1] | Ex 2[1]; C1 | 4-(3-methoxyazetidin-1-yl)-7-methyl-5-[1-methyl-5-(4-methylphenyl)-1H-pyrazol-4-yl]imidazo[5,1-f][1,2,4]triazine | Characteristic peaks: 2.34 (s, 3H), 2.64 (s, 3H), 3.25 (s, 3H), 3.91 (s, 3H), 7.15-7.24 (m, 4H), 7.65 (s, 1H), 7.78 (s, 1H); 390.6 |

TABLE 1-continued

| Ex No | Structure | Method of Prep; starting material | IUPAC Name | ¹H NMR (400 MHz, CDCl₃), δ (ppm); LCMS, observed ion m/z (M + 1) or HPLC retention time (minutes); MS observed ion m/z (M + 1) (unless otherwise indicated) |
|---|---|---|---|---|
| 30 | 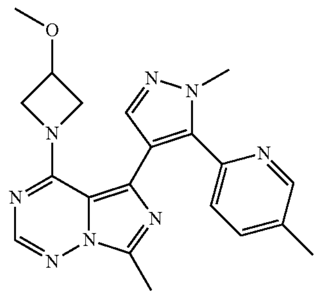 [SMILES: COC1CN(c2ncnn3c(C)nc(-c4cnn(C)c4-c4ccc(C)cn4)c23)C1] | Ex 2¹; C1 | 4-(3-methoxyazetidin-1-yl)-7-methyl-5-[1-methyl-5-(5-methylpyridin-2-yl)-1H-pyrazol-4-yl]imidazo[5,1-f][1,2,4]triazine | Characteristic peaks: 2.33 (br s, 3H), 2.69 (s, 3H), 3.22 (s, 3H), 4.11 (s, 3H), 7.33-7.37 (m, 1H), 7.65 (s, 1H), 7.79 (s, 1H), 8.51-8.52 (m, 1H); 391.6 |
| 31 | 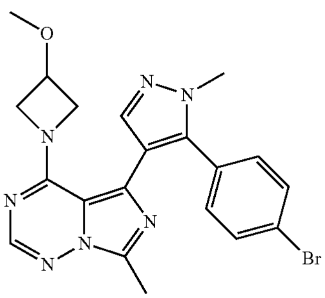 [SMILES: COC1CN(c2ncnn3c(C)nc(-c4cnn(C)c4-c4ccc(Br)cc4)c23)C1] | Ex 2¹; C1 | 5-[5-(4-bromophenyl)-1-methyl-1H-pyrazol-4-yl]-4-(3-methoxyazetidin-1-yl)-7-methylimidazo[5,1-f][1,2,4]triazine | Characteristic peaks: 2.64 (s, 3H), 3.25 (s, 3H), 3.91 (s, 3H), 7.24 (d, J = 8.7 Hz, 2H), 7.51 (d, J = 8.7 Hz, 2H), 7.66 (s, 1H), 7.81 (s, 1 H); 454.6 |
| 32 | 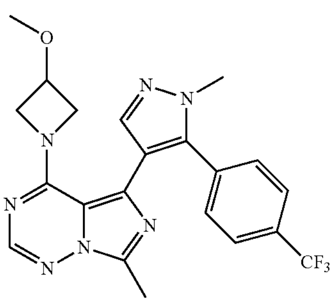 [SMILES: COC1CN(c2ncnn3c(C)nc(-c4cnn(C)c4-c4ccc(C(F)(F)F)cc4)c23)C1] | Ex 2¹; C1 | 4-(3-methoxyazetidin-1-yl)-7-methyl-5-{1-methyl-5-[4-(trifluoromethyl)phenyl]-1H-pyrazol-4-yl}imidazo[5,1-f][1,2,4]triazine | Characteristic peaks: 2.65 (s, 3H), 3.26 (s, 3H), 3.93 (s, 3H), 4.10-4.13 (m, 1H), 7.52 (br d, J = 8 Hz, 2H), 7.64 (br d, J = 8 Hz, 2H), 7.68 (s, 1H), 7.82 (s, 1H); 444.6 |
| 33 | 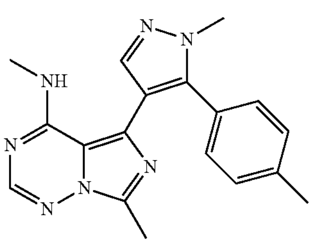 [SMILES: CNc1ncnn2c(C)nc(-c3cnn(C)c3-c3ccc(C)cc3)c12] | Ex 8²; C4 | N,7-dimethyl-5-[1-methyl-5-(4-methylphenyl)-1H-pyrazol-4-yl]imidazo[5,1-f][1,2,4]triazin-4-amine | ¹H NMR (500 MHz, CDCl₃): 2.36 (s, 3H), 2.63 (s, 3H), 2.89 (d, J = 5.0 Hz, 3H), 3.93 (s, 3H), 5.40-5.45 (m, 1H), 7.20 (br AB quartet, $J_{AB}$ = 8.3 Hz, $\Delta v_{AB}$ = 18.3 Hz, 4H), 7.72 (s, 1H), 7.84 (s, 1H); 334.5 |
| 34 | 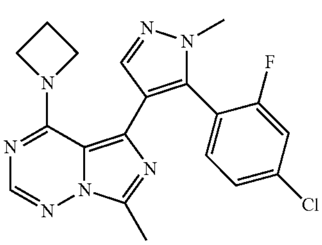 [SMILES: Cc1nc(-c2cnn(C)c2-c2ccc(Cl)cc2F)c2c(N3CCC3)ncnn12] | Ex 10; C3 | 4-(azetidin-1-yl)-5-[5-(4-chloro-2-fluorophenyl)-1-methyl-1H-pyrazol-4-yl]-7-methylimidazo[5,1-f][1,2,4]triazine | ¹H NMR (400 MHz, CD₃OD): 2.23-2.32 (m, 2H), 2.56 (s, 3H), 3.6-4.3 (v br m, 4H), 3.85 (d, J = 1.4 Hz, 3H), 7.19-7.27 (m, 2H), 7.37 (dd, J = 10.2, 1.8 Hz, 1H), 7.73 (s, 1H), 7.74 (s, 1 H); 398.4, 400.4 |

TABLE 1-continued

| Ex No | Structure | Method of Prep; starting material | IUPAC Name | $^1$H NMR (400 MHz, CDCl$_3$), δ (ppm); LCMS, observed ion m/z (M + 1) or HPLC retention time (minutes); MS observed ion m/z (M + 1) (unless otherwise indicated) |
|---|---|---|---|---|
| 35 | 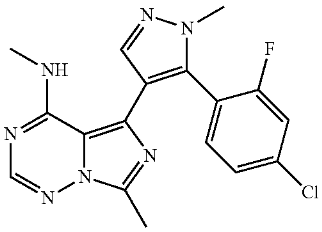 [SMILES: CNc1ncnn2c(C)nc(-c3cnn(C)c3-c3ccc(Cl)cc3F)c12] | Ex 10; C3 | 5-[5-(4-chloro-2-fluorophenyl)-1-methyl-1H-pyrazol-4-yl]-N,7-dimethylimidazo[5,1-f][1,2,4]triazin-4-amine | $^1$H NMR (400 MHz, CD$_3$OD): 2.55 (s, 3H), 2.90 (s, 3H), 3.85 (d, J = 1.2 Hz, 3H), 7.18-7.25 (m, 2H), 7.35 (dd, J = 10, 2 Hz, 1H), 7.77 (s, 1H), 7.80 (s, 1 H); 372.4 |
| 36 | 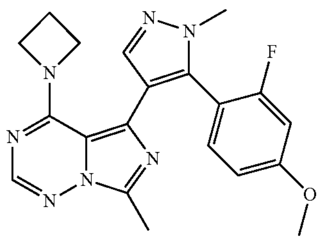 [SMILES: COc1ccc(-c2c(-c3nc(C)n4ncnc(N5CCC5)c34)cnn2C)c(F)c1] | Ex 10$^3$; C3 | 4-(azetidin-1-yl)-5-[5-(2-fluoro-4-methoxyphenyl)-1-methyl-1H-pyrazol-4-yl]-7-methylimidazo[5,1-f][1,2,4]triazine | $^1$H NMR (400 MHz, CD$_3$OD): 2.22-2.31 (m, 2H), 2.56 (s, 3H), 3.6-3.9 (v br m, 2H), 3.78 (s, 3H), 3.82 (br s, 3H), 4.0-4.3 (v br m, 2H), 6.71 (dd, J = 8.6, 2.4 Hz, 1H), 6.82 (dd, J = 12.4, 2.4 Hz, 1H), 7.09 (dd, J = 8.6, 8.5 Hz, 1H), 7.69 (s, 1H), 7.71 (s, 1H); 394.3 |
| 37 | 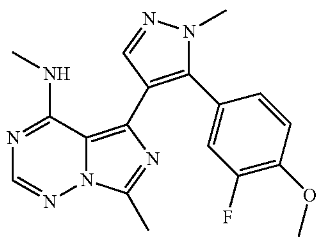 [SMILES: CNc1ncnn2c(C)nc(-c3cnn(C)c3-c3ccc(OC)c(F)c3)c12] | Ex 8$^2$; C4 | 5-[5-(3-fluoro-4-methoxyphenyl)-1-methyl-1H-pyrazol-4-yl]-N,7-dimethylimidazo[5,1-f][1,2,4]triazin-4-amine | 2.63 (s, 3H), 2.97 (d, J = 5.0 Hz, 3H), 3.90 (s, 3H), 3.93 (s, 3H), 5.46-5.51 (m, 1H), 6.96 (dd, J = 8.7, 8.5 Hz, 1H), 7.08-7.15 (m, 2H), 7.70 (s, 1H), 7.88 (s, 1H); 368.2 |
| 38 | 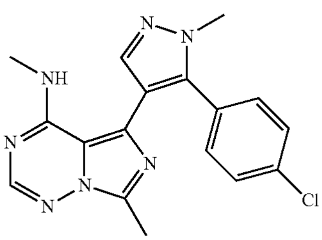 [SMILES: CNc1ncnn2c(C)nc(-c3cnn(C)c3-c3ccc(Cl)cc3)c12] | Ex 8$^2$; C4 | 5-[5-(4-chlorophenyl)-1-methyl-1H-pyrazol-4-yl]-N,7-dimethylimidazo[5,1-f][1,2,4]triazin-4-amine | 2.61 (s, 3H), 2.97 (d, J = 5.0 Hz, 3H), 3.93 (s, 3H), 5.45-5.51 (m, 1H), 7.33 (AB quartet, J$_{AB}$ = 8.8 Hz, Δν$_{AB}$ = 22.4 Hz, 4H), 7.70 (s, 1H), 7.88 (s, 1H); 354.0 |
| 39 | 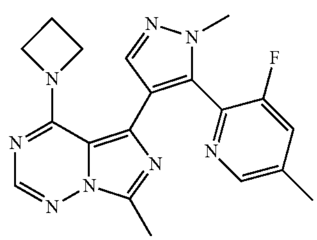 [SMILES: Cc1cnc(-c2c(-c3nc(C)n4ncnc(N5CCC5)c34)cnn2C)c(F)c1] | Ex 11; C7 | 4-(azetidin-1-yl)-5-[5-(3-fluoro-5-methylpyridin-2-yl)-1-methyl-1H-pyrazol-4-yl]-7-methylimidazo[5,1-f][1,2,4]triazine | 2.19-2.28 (m, 2H), 2.38 (br s, 3H), 2.59 (s, 3H), 3.8-4.1 (br m, 4H), 3.97 (s, 3H), 7.15 (br d, J = 10 Hz, 1H), 7.72 (s, 1H), 7.76 (s, 1H), 8.34-8.36 (m, 1H); 379.2 |
| 40 | 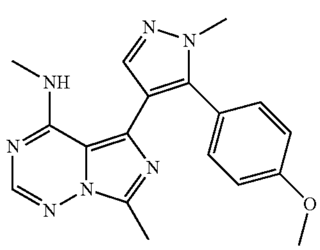 [SMILES: CNc1ncnn2c(C)nc(-c3cnn(C)c3-c3ccc(OC)cc3)c12] | Ex 8$^2$; C4 | 5-[5-(4-methoxyphenyl)-1-methyl-1H-pyrazol-4-yl]-N,7-dimethylimidazo[5,1-f][1,2,4]triazin-4-amine | 2.63 (s, 3H), 2.90 (d, J = 5.0 Hz, 3H), 3.81 (s, 3H), 3.92 (s, 3H), 5.42-5.49 (m, 1H), 6.90 (br d, J = 8.9 Hz, 2H), 7.26 (br d, J = 8.9 Hz, 2H), 7.71 (s, 1H), 7.84 (s, 1 H); 350.1 |

TABLE 1-continued

| Ex No | Method of Prep; starting material | IUPAC Name | $^1$H NMR (400 MHz, CDCl$_3$), δ (ppm); LCMS, observed ion m/z (M + 1) or HPLC retention time (minutes); MS observed ion m/z (M + 1) (unless otherwise indicated) |
|---|---|---|---|
| 41 | Ex 11; C4 | 5-[5-(3-fluoro-5-methylpyridin-2-yl)-1-methyl-1H-pyrazol-4-yl]-N,7-dimethylimidazo[5,1-f][1,2,4]triazin-4-amine | 2.39 (s, 3H), 2.59 (s, 3H), 2.95 (d, J = 5.1 Hz, 3H), 3.95 (s, 3H), 5.87-5.93 (m, 1H), 7.21 (br d, J = 10 Hz, 1H), 7.75 (s, 1H), 7.85 (s, 1H), 8.34 (br s, 1H); 353.1 |
| 42 | Ex 2; C2 | 4-(azetidin-1-yl)-5-{5-[3-chloro-5-(trifluoromethyl)pyridin-2-yl]-1-methyl-1H-pyrazol-4-yl}-7-methylimidazo[5,1-f][1,2,4]triazine | 2.24-2.31 (m, 2H), 2.57 (s, 3H), 3.91 (s, 3H), 3.95-4.07 (br m, 4H), 7.77 (s, 1H), 7.78 (s, 1H), 7.92 (br d, J = 1.7 Hz, 1H), 8.89-8.91 (m, 1H); 449.0 |
| 43 | Ex 2; C2 | 4-(azetidin-1-yl)-5-{5-[3-fluoro-5-(trifluoromethyl)pyridin-2-yl]-1-methyl-1H-pyrazol-4-yl}-7-methylimidazo[5,1-f][1,2,4]triazine | 2.22-2.31 (m, 2H), 2.58 (s, 3H), 3.86-4.08 (br m, 4H), 4.03 (s, 3H), 7.59 (dd, J = 9.0, 1.4 Hz, 1H), 7.73 (s, 1H), 7.81 (s, 1H), 8.83 (br s, 1H); 433.1 |
| 44 | Ex 8[2]; C4 | 5-[5-(4-methoxy-2-methylphenyl)-1-methyl-1H-pyrazol-4-yl]-N,7-dimethylimidazo[5,1-f][1,2,4]triazin-4-amine | $^1$H NMR (500 MHz, CDCl$_3$): 2.03 (s, 3H), 2.58 (s, 3H), 2.99 (d, J = 5.0 Hz, 3H), 3.73 (s, 3H), 3.80 (s, 3H), 5.52-5.57 (m, 1H), 6.74-6.78 (m, 2H), 7.16 (d, J = 8.3 Hz, 1H), 7.73 (s, 1H), 7.85 (s, 1H); 364.1 |
| 45 | Ex 8[2]; C4 | 5-[5-(2-fluoro-4-methoxyphenyl)-1-methyl-1H-pyrazol-4-yl]-N,7-dimethylimidazo[5,1-f][1,2,4]triazin-4-amine | 2.63 (s, 3H), 2.94 (d, J = 5.0 Hz, 3H), 3.80 (s, 3H), 3.84 (d, J = 1.5 Hz, 3H), 5.44-5.51 (m, 1H), 6.64 (dd, J = 8.6, 2.5 Hz, 1H), 6.70 (dd, J = 11.9, 2.4 Hz, 1H), 7.09 (dd, J = 8.6, 8.6 Hz, 1H), 7.75 (s, 1H), 7.82 (s, 1H); 368.2 |
| 46 | Ex 8[2]; C4 | 5-[5-(2,3-difluoro-4-methoxyphenyl)-1-methyl-1H-pyrazol-4-yl]-N,7-dimethylimidazo[5,1-f][1,2,4]triazin-4-amine | 2.63 (s, 3H), 2.98 (d, J = 5.0 Hz, 3H), 3.86 (d, J = 1.5 Hz, 3H), 3.91 (s, 3H), 5.43-5.49 (m, 1H), 6.71 (ddd, J = 8.7, 7.6, 1.8 Hz, 1H), 6.95 (ddd, J = 8.8, 7.6, 2.4 Hz, 1H), 7.76 (s, 1H), 7.85 (s, 1H); 386.2 |

TABLE 1-continued

| Ex No | Structure | Method of Prep; starting material | IUPAC Name | $^1$H NMR (400 MHz, CDCl$_3$), δ (ppm); LCMS, observed ion m/z (M + 1) or HPLC retention time (minutes); MS observed ion m/z (M + 1) (unless otherwise indicated) |
|---|---|---|---|---|
| 47 | 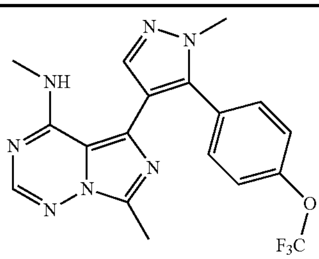 | Method A; C4 | N,7-dimethyl-5-{1-methyl-5-[4-(trifluoromethoxy)phenyl]-1H-pyrazol-4-yl}imidazo[5,1-f][1,2,4]triazin-4-amine | 2.62 (s, 3H), 2.98 (d, J = 5.0 Hz, 3H), 3.95 (s, 3H), 5.44-5.51 (m, 1H), 7.22-7.26 (m, 2H), 7.44 (d, J = 9.0 Hz, 2H), 7.71 (s, 1H), 7.89 (s, 1H); 404.1 |
| 48 | 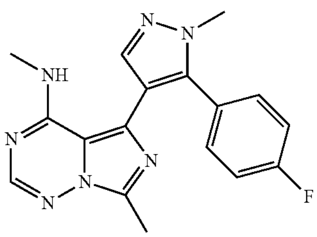 [SMILES: CNc1ncnn2c(C)nc(-c3cnn(C)c3-c3ccc(F)cc3)c12] | Ex 7; C1[4] | 5-[5-(4-fluorophenyl)-1-methyl-1H-pyrazol-4-yl]-N,7-dimethylimidazo[5,1-f][1,2,4]triazin-4-amine | $^1$H NMR (500 MHz, CDCl$_3$): 2.63 (s, 3H), 2.97 (d, J = 5.1 Hz, 3H), 3.92 (s, 3H), 5.46-5.53 (m, 1H), 7.09 (dd, J = 8.7, 8.6 Hz, 2H), 7.34 (br dd, J = 8.8, 5.3 Hz, 2H), 7.71 (s, 1H), 7.88 (s, 1H); 338.1 |
| 49 | 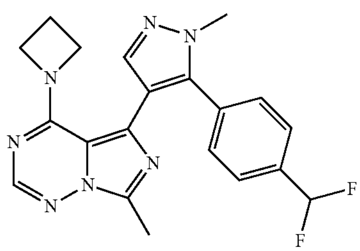 [SMILES: Cc1nc(-c2cnn(C)c2-c2ccc(C(F)F)cc2)c2c(N3CCC3)ncnn12] | Method B; C7 | 4-(azetidin-1-yl)-5-{5-[4-(difluoromethyl)phenyl]-1-methyl-1H-pyrazol-4-yl}-7-methylimidazo[5,1-f][1,2,4]triazine | $^1$H NMR (400 MHz, CD$_3$OD): 2.24-2.33 (m, 2H), 2.57 (s, 3H), 3.6-3.9 (v br m, 2H), 3.93 (s, 3H), 3.9-4.2 (v br m, 2H), 6.76 (t, J = 56.1 Hz, 1H), 7.53 (br AB quartet, J$_{AB}$ = 8 Hz, Δν$_{AB}$ = 32 Hz, 4H), 7.71 (s, 1H), 7.72 (s, 1H); 396.5 |
| 50 | 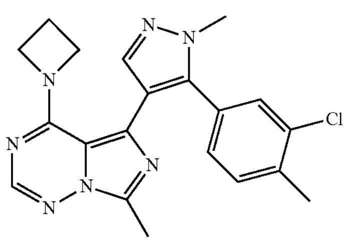 [SMILES: Cc1ccc(-c2c(-c3nc(C)n4ncnc(N5CCC5)c34)cnn2C)cc1Cl] | Ex 2; C2 | 4-(azetidin-1-yl)-5-[5-(3-chloro-4-methylphenyl)-1-methyl-1H-pyrazol-4-yl]-7-methylimidazo[5,1-f][1,2,4]triazine | $^1$H NMR (500 MHz, CDCl$_3$): 2.21-2.30 (m, 2H), 2.35 (s, 3H), 2.62 (s, 3H), 3.4-4.3 (v br m, 4H), 3.89 (s, 3H), 7.14 (dd, J = 7.8, 1.7 Hz, 1H), 7.20 (d, J = 7.8 Hz, 1H), 7.40 (d, J = 1.6 Hz, 1H), 7.63 (s, 1H), 7.78 (s, 1H); 394.1 |
| 51 | 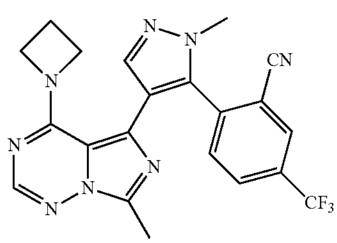 [SMILES: Cc1nc(-c2cnn(C)c2-c2ccc(C(F)(F)F)cc2C#N)c2c(N3CCC3)ncnn12] | Ex 8[5,6]; C7 | 2-{4-[4-(azetidin-1-yl)-7-methylimidazo[5,1-f][1,2,4]triazin-5-yl]-methyl-1H-pyrazol-5-yl}-5-(trifluoromethyl)benzonitrile | 2.27-2.35 (m, 2H), 2.59 (s, 3H), 3.91 (s, 3H), 3.9-4.1 (br m, 4H), 7.72 (s, 1H), 7.80 (s, 1H), 7.85-7.88 (m, 2H), 7.99 (br s, 1H); 439.1 |
| 52 | 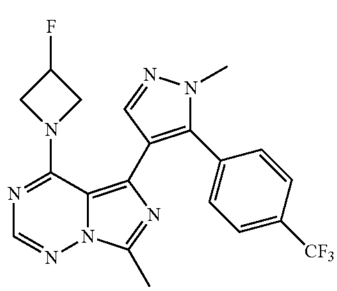 [SMILES: Cc1nc(-c2cnn(C)c2-c2ccc(C(F)(F)F)cc2)c2c(N3CC(F)C3)ncnn12] | Method A; C3 | 4-(3-fluoroazetidin-1-yl)-7-methyl-5-{1-methyl-5-[4-(trifluoromethyl)phenyl]-1H-pyrazol-4-yl}imidazo[5,1-f][1,2,4]triazine | 2.71 (s, 3H), 3.8-4.0 (br m, 2H), 3.93 (s, 3H), 4.0-4.3 (br m, 2H), 5.13-5.33 (m, J$_{HF}$ = 57.0 Hz, 1H), 7.62 (AB quartet, J$_{AB}$ = 8.1 Hz, Δν$_{AB}$ = 35.7 Hz, 4H), 7.70 (s, 1H), 7.86 (s, 1H); GCMS m/z 431 (M) |

TABLE 1-continued

| Ex No | Structure | Method of Prep; starting material | IUPAC Name | $^1$H NMR (400 MHz, CDCl$_3$), δ (ppm); LCMS, observed ion m/z (M + 1) or HPLC retention time (minutes); MS observed ion m/z (M + 1) (unless otherwise indicated) |
|---|---|---|---|---|
| 53 | 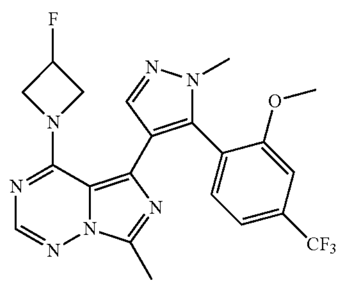 [SMILES: COc1cc(C(F)(F)F)ccc1-c1c(-c2nc(C)n3ncnc(N4CC(F)C4)c23)cnn1C] | Ex 8; C3 | 4-(3-fluoroazetidin-1-yl)-5-{5-[2-methoxy-4-(trifluoromethyl)phenyl]-1-methyl-1H-pyrazol-4-yl}-7-methylimidazo[5,1-f][1,2,4]triazine | 2.64 (s, 3H), 3.78 (s, 3H), 3.89 (br s, 3H), 3.9-4.5 (v br m, 4H), 5.11-5.31 (m, J$_{HF}$ = 57.3 Hz, 1H), 7.16 (br s, 1H), 7.18 (br d, J = 8 Hz, 1 H), 7.41 (br d, J = 8 Hz, 1H), 7.67 (s, 1H), 7.79 (s, 1H); 462.2 |
| 54 | 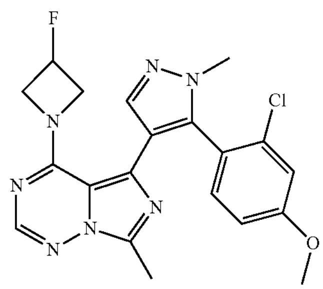 [SMILES: COc1ccc(-c2c(-c3nc(C)n4ncnc(N5CC(F)C5)c34)cnn2C)c(Cl)c1] | Ex 8; C3 | 5-[5-(2-chloro-4-methoxyphenyl)-1-methyl-1H-pyrazol-4-yl]-4-(3-fluoroazetidin-1-yl)-7-methylimidazo[5,1-f][1,2,4]triazine | Characteristic peaks: 2.95 (br s, 3H), 3.80 (s, 3H), 3.83 (s, 3H), 3.9-4.7 (v br m, 4H), 5.16-5.38 (m, J$_{HF}$ = 56 Hz, 1H), 6.96-7.02 (m, 2H), 7.70 (s, 1H), 8.01 (s, 1 H); 428.1 |
| 55 | 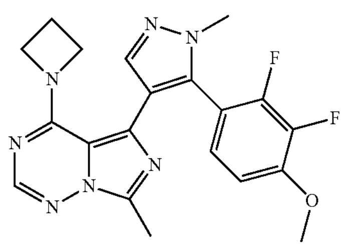 [SMILES: COc1ccc(-c2c(-c3nc(C)n4ncnc(N5CCC5)c34)cnn2C)c(F)c1F] | Method A; C7 | 4-(azetidin-1-yl)-5-[5-(2,3-difluoro-4-methoxyphenyl)-1-methyl-1H-pyrazol-4-yl]-7-methylimidazo[5,1-f][1,2,4]triazine | 2.21-2.30 (m, 2H), 2.63 (s, 3H), 3.4-4.4 (v br m, 4H), 3.84 (d, J = 1.6 Hz, 3H), 3.89 (s, 3H), 6.68 (ddd, J = 8.8, 7.6, 1.8 Hz, 1H), 7.02 (ddd, J = 8.8, 7.6, 2.3 Hz, 1H), 7.68 (s, 1H), 7.77 (s, 1H); 412.1 |
| 56 | 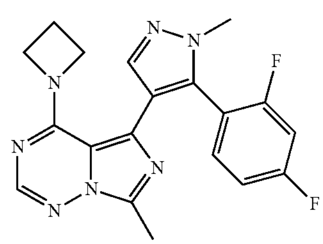 [SMILES: Cc1nc(-c2cnn(C)c2-c2ccc(F)cc2F)c2c(N3CCC3)ncnn12] | Method A; C7 | 4-(azetidin-1-yl)-5-[5-(2,4-difluorophenyl)-1-methyl-1H-pyrazol-4-yl]-7-methylimidazo[5,1-f][1,2,4]triazine | $^1$H NMR (400 MHz, CD$_3$OD): 2.22-2.32 (m, 2H), 2.55 (s, 3H), 3.5-4.4 (v br m, 4H), 3.84 (d, J = 0.8 Hz, 3H), 6.97 (ddd, J = 8.4, 8.4, 2.3 Hz, 1H), 7.12 (ddd, J = 10.4, 9.1, 2.3 Hz, 1H), 7.25-7.32 (m, 1H), 7.71 (s, 1H), 7.74 (s, 1H); 382.2 |
| 57 | 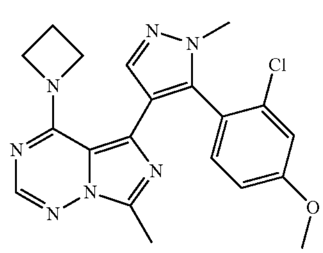 [SMILES: COc1ccc(-c2c(-c3nc(C)n4ncnc(N5CCC5)c34)cnn2C)c(Cl)c1] | Ex 8; C7 | 4-(azetidin-1-yl)-5-[5-(2-chloro-4-methoxyphenyl)-1-methyl-1H-pyrazol-4-yl]-7-methylimidazo[5,1-f][1,2,4]triazine | 2.20-2.29 (m, 2H), 2.60 (s, 3H), 3.6-4.3 (br m, 4H), 3.78 (s, 3H), 3.79 (s, 3H), 6.77 (dd, J = 8.6, 2.6 Hz, 1H), 6.96 (d, J = 2.5 Hz, 1H), 7.39 (d, J = 8.7 Hz, 1H), 7.64 (s, 1H), 7.76 (s, 1H); APCl m/z 410.3, 412.4 (M + 1) |

TABLE 1-continued

| Ex No | Structure | Method of Prep; starting material | IUPAC Name | $^1$H NMR (400 MHz, CDCl$_3$), δ (ppm); LCMS, observed ion m/z (M + 1) or HPLC retention time (minutes); MS observed ion m/z (M + 1) (unless otherwise indicated) |
|---|---|---|---|---|
| 58 | 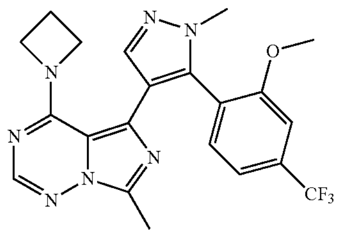 [SMILES: COc1cc(C(F)(F)F)ccc1-c1c(-c2nc(C)n3ncnc(N4CCC4)c23)cnn1C] | Ex 8; C7 | 4-(azetidin-1-yl)-5-{5-[2-methoxy-4-(trifluoromethyl)phenyl]-1-methyl-1H-pyrazol-4-yl}-7-methylimidazo[5,1-f][1,2,4]triazine | Characteristic peaks: 2.28-2.48 (br m, 2H), 2.88 (s, 3H), 3.75 (s, 3H), 3.83-3.93 (br m, 2H), 3.90 (s, 3H), 4.47-4.55 (m, 2H), 7.18 (br s, 1H), 7.37 (br d, J = 8 Hz, 1H), 7.70 (s, 1H), 7.96 (s, 1H); 444.1 |
| 59 | 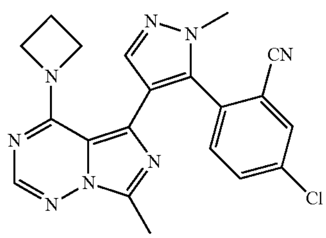 [SMILES: Cc1nc(-c2cnn(C)c2-c2ccc(Cl)cc2C#N)c2c(N3CCC3)ncnn12] | Ex 8[5,7]; C7 | 2-{4-[4-(azetidin-1-yl)-7-methylimidazo[5,1-f][1,2,4]triazin-5-yl]-1-methyl-1H-pyrazol-5-yl}-5-chlorobenzonitrile | 2.26-2.35 (m, 2H), 2.60 (s, 3H), 3.84-4.20 (br m, 4H), 3.89 (s, 3H), 7.58 (br s, 2H), 7.70-7.72 (m, 2H), 7.80 (s, 1H); 405.1 |
| 60 | 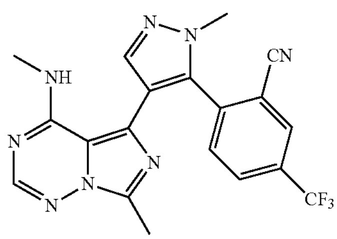 [SMILES: CNc1ncnn2c(C)nc(-c3cnn(C)c3-c3ccc(C(F)(F)F)cc3C#N)c12] | Ex 8[5,6]; C4 | 2-{1-methyl-4-[7-methyl-4-(methylamino)imidazo[5,1-f][1,2,4]triazin-5-yl]-1H-pyrazol-5-yl}-5-(trifluoromethyl)benzonitrile | 2.54 (s, 3H), 3.07 (d, J = 5.0 Hz, 3H), 3.89 (s, 3H), 5.56-5.62 (m, 1H), 7.75 (s, 1H), 7.82 (br d, J = 8.1 Hz, 1 H), 7.90 (s, 1 H), 7.92 (br dd, J = 8.2, 1.3 Hz, 1H), 7.95 (br s, 1H); 413.1 |
| 61 | 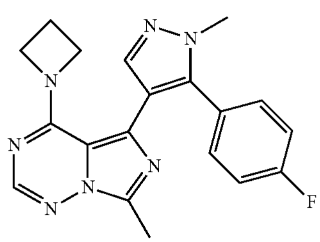 [SMILES: Cc1nc(-c2cnn(C)c2-c2ccc(F)cc2)c2c(N3CCC3)ncnn12] | Ex 2; C2 | 4-(azetidin-1-yl)-5-[5-(4-fluorophenyl)-1-methyl-1H-pyrazol-4-yl]-7-methylimidazo[5,1-f][1,2,4]triazine | 2.20-2.29 (m, 2H), 2.62 (s, 3H), 3.4-4.3 (v br m, 4H), 3.89 (s, 3H), 7.06 (dd, J = 8.7, 8.7 Hz, 2H), 7.36 (br dd, J = 8.7, 5.3 Hz, 2H), 7.64 (s, 1H), 7.79 (s, 1H); 364.1 |
| 62 | 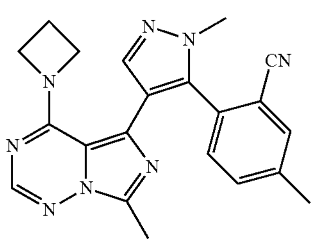 [SMILES: Cc1ccc(-c2c(-c3nc(C)n4ncnc(N5CCC5)c34)cnn2C)c(C#N)c1] | Ex 2[8]; C2 | 2-{4-[4-(azetidin-1-yl)-7-methylimidazo[5,1-f][1,2,4]triazin-5-yl]-1-methyl-1H-pyrazol-5-yl}-5-methylbenzonitrile | 2.24-2.35 (m, 2H), 2.39 (s, 3H), 2.59 (s, 3H), 3.7-4.2 (v br m, 4H), 3.88 (s, 3H), 7.36 (br dd, J = 8, 1 Hz, 1H), 7.42 (d, J = 8.0 Hz, 1H), 7.52-7.54 (m, 1H), 7.69 (s, 1H), 7.76 (s, 1H); 385.2 |
| 63 | 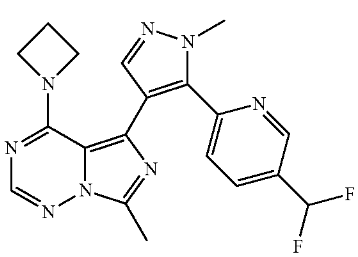 [SMILES: Cc1nc(-c2cnn(C)c2-c2ccc(C(F)F)cn2)c2c(N3CCC3)ncnn12] | Ex 2[9]; C2 | 4-(azetidin-1-yl)-5-{5-[5-(difluoromethyl)pyridin-2-yl]-1-methyl-1H-pyrazol-4-yl}-7-methylimidazo[5,1-f][1,2,4]triazine | 2.14-2.25 (m, 2H), 2.69 (s, 3H), 3.4-3.8 (br m, 2H), 3.8-4.3 (br m, 2H), 4.16 (s, 3H), 6.71 (t, J = 55.8 Hz, 1 H), 7.55 (br d, J = 8 Hz, 1H), 7.66 (s, 1H), 7.71 (br d, J = 8 Hz, 1H), 7.81 (s, 1H), 8.83 (br s, 1H); 397.2 |

TABLE 1-continued

| Ex No | Structure | Method of Prep; starting material | IUPAC Name | $^1$H NMR (400 MHz, CDCl$_3$), δ (ppm); LCMS, observed ion m/z (M + 1) or HPLC retention time (minutes); MS observed ion m/z (M + 1) (unless otherwise indicated) |
|---|---|---|---|---|
| 64 | 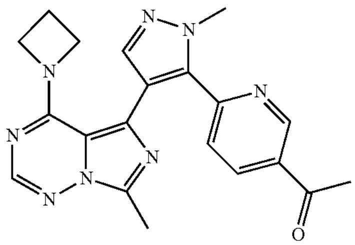 [SMILES: CC(=O)c1ccc(-c2c(-c3nc(C)n4ncnc(N5CCC5)c34)cnn2C)nc1] | Ex 2[10]; C2 | 1-(6-{4-[4-(azetidin-1-yl)-7-methylimidazo[5,1-f][1,2,4]triazin-5-yl]-1-methyl-1H-pyrazol-5-yl}pyridin-3-yl)ethanone | 2.15-2.24 (m, 2H), 2.61 (s, 3H), 2.69 (s, 3H), 3.4-3.8 (v br m, 2H), 3.8-4.3 (v br m, 2H), 4.18 (s, 3H), 7.51 (d, J = 8.2 Hz, 1H), 7.65 (s, 1H), 7.80 (s, 1H), 8.05 (dd, J = 8.3, 2.3 Hz, 1H), 9.22 (br d, J = 2.2 Hz, 1H); 389.3 |
| 65 | 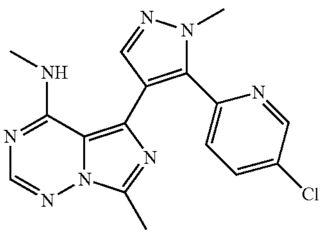 [SMILES: CNc1ncnn2c(C)nc(-c3cnn(C)c3-c3ccc(Cl)cn3)c12] | Ex 7; C6 | 5-[5-(5-chloropyridin-2-yl)-1-methyl-1H-pyrazol-4-yl]-N,7-dimethylimidazo[5,1-f][1,2,4]triazin-4-amine | 2.68 (s, 3H), 2.92 (d, J = 5.0 Hz, 3H), 4.13 (s, 3H), 5.46-5.52 (m, 1H), 7.46 (dd, J = 8.4, 0.7 Hz, 1H), 7.59 (dd, J = 8.4, 2.5 Hz, 1H), 7.70 (s, 1H), 7.89 (s, 1H), 8.66 (dd, J = 2.5, 0.7 Hz, 1H); 355.1 |
| 66 | 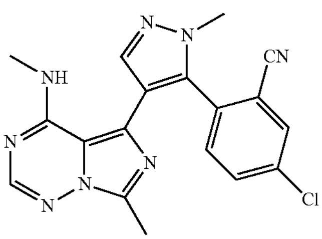 [SMILES: CNc1ncnn2c(C)nc(-c3cnn(C)c3-c3ccc(Cl)cc3C#N)c12] | Ex 8[5,7]; C4 | 5-chloro-2-{1-methyl-4-[7-methyl-4-(methylamino)imidazo[5,1-f][1,2,4]triazin-5-yl]-1H-pyrazol-5-yl}benzonitrile | 2.56 (s, 3H), 3.05 (d, J = 5.0 Hz, 3H), 3.87 (s, 3H), 5.54-5.60 (m, 1H), 7.56 (d, J = 8.4 Hz, 1H), 7.63 (dd, J = 8.4, 2.2 Hz, 1H), 7.68 (d, J = 2.2 Hz, 1H), 7.73 (s, 1H), 7.89 (s, 1H); 379.1 |
| 67 | 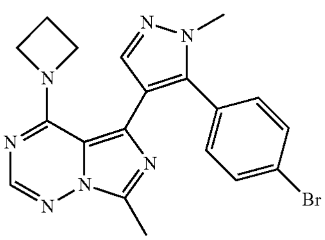 [SMILES: Cc1nc(-c2cnn(C)c2-c2ccc(Br)cc2)c2c(N3CCC3)ncnn12] | Ex 2; C2 | 4-(azetidin-1-yl)-5-[5-(4-bromophenyl)-1-methyl-1H-pyrazol-4-yl]-7-methylimidazo[5,1-f][1,2,4]triazine | 2.19-2.28 (m, 2H), 2.61 (s, 3H), 3.1-4.3 (v br m, 4H), 3.88 (s, 3H), 7.25 (d, J = 8.5 Hz, 2H), 7.49 (d, J = 8.5 Hz, 2H), 7.62 (s, 1H), 7.78 (s, 1H); 426.1 |
| 68 | 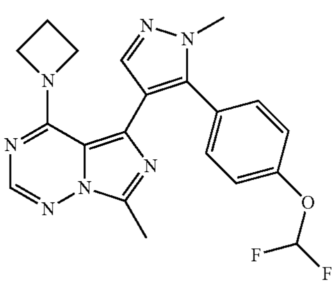 [SMILES: Cc1nc(-c2cnn(C)c2-c2ccc(OC(F)F)cc2)c2c(N3CCC3)ncnn12] | Ex 2; C2 | 4-(azetidin-1-yl)-5-{5-[4-(difluoromethoxy)phenyl]-1-methyl-1H-pyrazol-4-yl}-7-methylimidazo[5,1-f][1,2,4]triazine | 2.19-2.28 (m, 2H), 2.62 (s, 3H), 3.3-4.4 (v br m, 4H), 3.89 (s, 3H), 6.51 (t, J = 73.4 Hz, 1H), 7.11 (br d, J = 8.7 Hz, 2H), 7.39 (br d, J = 8.7 Hz, 2H), 7.62 (s, 1H), 7.78 (s, 1H); 412.2 |
| 69 | 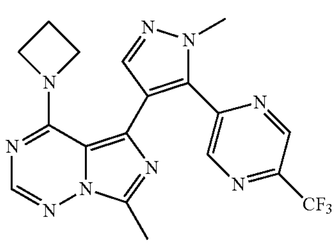 [SMILES: Cc1nc(-c2cnn(C)c2-c2cnc(C(F)(F)F)cn2)c2c(N3CCC3)ncnn12] | Ex 2; C2 | 4-(azetidin-1-yl)-7-methyl-5-{1-methyl-5-[5-(trifluoromethyl)pyrazin-2-yl]-1H-pyrazol-4-yl}imidazo[5,1-f][1,2,4]triazine | 2.18-2.27 (m, 2H), 2.68 (s, 3H), 3.4-4.2 (v br m, 4H), 4.21 (s, 3H), 7.68 (s, 1 H), 7.85 (s, 1H), 8.92 (d, J = 1.2 Hz, 1H), 9.00 (d, J = 1.2 Hz, 1H); 416.2 |

TABLE 1-continued

| Ex No | Structure | Method of Prep; starting material | IUPAC Name | ¹H NMR (400 MHz, CDCl₃), δ (ppm); LCMS, observed ion m/z (M + 1) or HPLC retention time (minutes); MS observed ion m/z (M + 1) (unless otherwise indicated) |
|---|---|---|---|---|
| 70 | 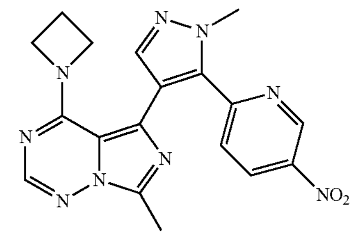 [SMILES: Cc1nc(-c2cnn(C)c2-c2ccc([N+](=O)[O-])cn2)c2c(N3CCC3)ncnn12] | Ex 2; C2 | 4-(azetidin-1-yl)-7-methyl-5-[1-methyl-5-(5-nitropyridin-2-yl)-1H-pyrazol-4-yl]imidazo[5,1-f][1,2,4]triazine | 2.18-2.26 (m, 2H), 2.70 (s, 3H), 3.3-4.3 (v br m, 4H), 4.21 (s, 3H), 7.67 (s, 1 H), 7.71 (dd, J = 8.8, 0.7 Hz, 1H), 7.83 (s, 1H), 8.34 (dd, J = 8.7, 2.7 Hz, 1H), 9.50 (dd, J = 2.6, 0.7 Hz, 1H); 392.2 |
| 71 | 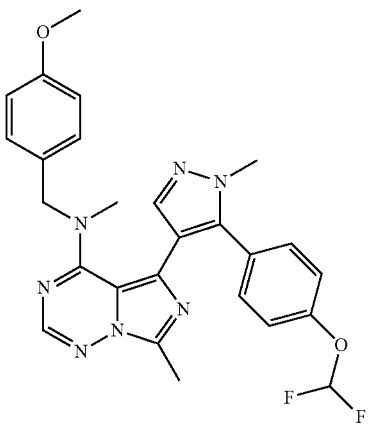 [SMILES: COc1ccc(CN(C)c2ncnn3c(C)nc(-c4cnn(C)c4-c4ccc(OC(F)F)cc4)c23)cc1] | Ex 7; C6 | 5-{5-[4-(difluoromethoxy)phenyl]-1-methyl-1H-pyrazol-4-yl}-N-(4-methoxybenzyl)-N,7-dimethylimidazo[5,1-f][1,2,4]triazin-4-amine | 2.66 (s, 6H), 3.75 (s, 3H), 3.85 (s, 3H), 4.46 (br s, 2H), 6.51 (t, J = 73.4 Hz, 1H), 6.78 (d, J = 8.5 Hz, 2H), 6.97 (d, J = 8.5 Hz, 2H), 7.08 (d, J = 8.6 Hz, 2H), 7.26 (d, J = 8.6 Hz, 2H), 7.66 (s, 1H), 7.80 (s, 1H); 506.4 |
| 72 | 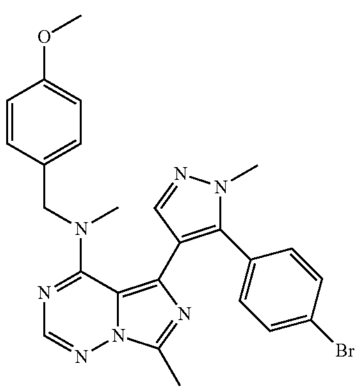 [SMILES: COc1ccc(CN(C)c2ncnn3c(C)nc(-c4cnn(C)c4-c4ccc(Br)cc4)c23)cc1] | Ex 7; C6 | 5-[5-(4-bromophenyl)-1-methyl-1H-pyrazol-4-yl]-N-(4-methoxybenzyl)-N,7-dimethylimidazo[5,1-f][1,2,4]triazin-4-amine | 2.67 (s, 6H), 3.78 (s, 3H), 3.86 (s, 3H), 4.48 (s, 2H), 6.80 (d, J = 7 Hz, 2H), 6.98 (d, J = 8 Hz, 2H), 7.14 (d, J = 7 Hz, 2H), 7.47 (d, J = 7 Hz, 2H), 7.67 (s, 1 H), 7.84 (s, 1H); 520.2 |
| 73 | 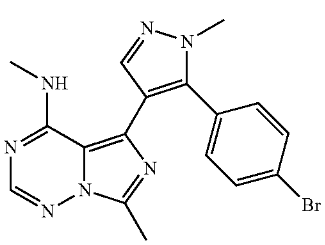 [SMILES: CNc1ncnn2c(C)nc(-c3cnn(C)c3-c3ccc(Br)cc3)c12] | Ex 7; Ex 72 | 5-[5-(4-bromophenyl)-1-methyl-1H-pyrazol-4-yl]-N,7-dimethylimidazo[5,1-f][1,2,4]triazin-4-amine | 2.60 (s, 3H), 2.95 (d, J = 4.9 Hz, 3H), 3.91 (s, 3H), 5.42-5.50 (m, 1H), 7.24 (d, J = 8.3 Hz, 2H), 7.51 (d, J = 8.3 Hz, 2H), 7.69 (s, 1H), 7.86 (s, 1H); 400.1 |

TABLE 1-continued

| Ex No | Structure | Method of Prep; starting material | IUPAC Name | $^1$H NMR (400 MHz, CDCl$_3$), δ (ppm); LCMS, observed ion m/z (M + 1) or HPLC retention time (minutes); MS observed ion m/z (M + 1) (unless otherwise indicated) |
|---|---|---|---|---|
| 74 | 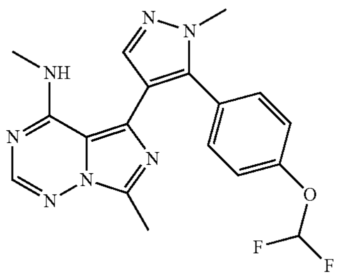 [SMILES: CNc1ncnn2c(C)nc(-c3cnn(C)c3-c3ccc(OC(F)F)cc3)c12] | Ex 7; Ex 71 | 5-{5-[4-(difluoromethoxy)phenyl]-1-methyl-1H-pyrazol-4-yl}-N,7-dimethylimidazo[5,1-f][1,2,4]triazin-4-amine | 2.61 (s, 3H), 2.96 (d, J = 5.0 Hz, 3H), 3.92 (s, 3H), 5.43-5.50 (s, 1H), 6.53 (t, J = 73.4 Hz, 1H), 7.13 (d, J = 8.5 Hz, 2H), 7.38 (d, J = 8.6 Hz, 2H), 7.70 (s, 1H), 7.86 (s, 1H); 386.2 |
| 75 | 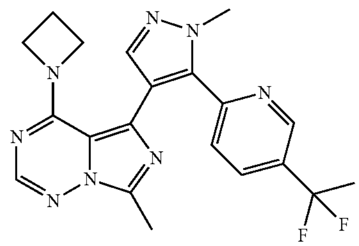 [SMILES: Cc1nc(-c2cnn(C)c2-c2ccc(C(C)(F)F)cn2)c2c(N3CCC3)ncnn12] | Method B; Ex 64 | 4-(azetidin-1-yl)-5-{5-[5-(1,1-difluoroethyl)pyridin-2-yl]-1-methyl-1H-pyrazol-4-yl}-7-methylimidazo[5,1-f][1,2,4]triazine | 1.96 (t, J = 18.2 Hz, 3H), 2.16-2.25 (m, 2H), 2.69 (s, 3H), 3.4-3.9 (br m, 2H), 3.9-4.3 (br m, 2H), 4.16 (s, 3H), 7.54 (d, J = 8.2 Hz, 1H), 7.64 (s, 1H), 7.69 (br d, J = 8.2 Hz, 1H), 7.81 (s, 1H), 8.83-8.85 (m, 1H); 411.2 |
| 76 | 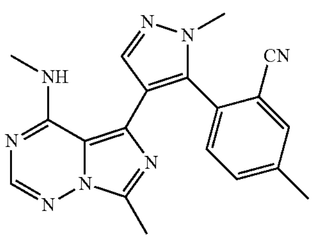 [SMILES: CNc1ncnn2c(C)nc(-c3cnn(C)c3-c3ccc(C)cc3C#N)c12] | Ex 8[5,11]; C4 | 5-methyl-2-{1-methyl-4-[7-methyl-4-(methylamino)imidazo[5,1-f][1,2,4]triazin-5-yl]-1H-pyrazol-5-yl}benzonitrile | 2.42 (s, 3H), 2.57 (s, 3H), 3.04 (d, J = 5.1 Hz, 3H), 3.86 (s, 3H), 5.55-5.61 (m, 1H), 7.44 (br s, 2H), 7.51 (br s, 1H), 7.72 (s, 1H), 7.87 (s, 1H); 359.1 |
| 77 | 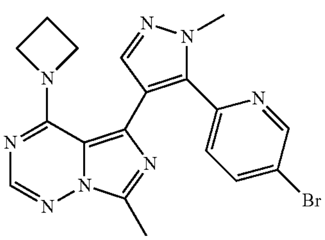 [SMILES: Cc1nc(-c2cnn(C)c2-c2ccc(Br)cn2)c2c(N3CCC3)ncnn12] | Footnote 12; Ex 70 | 4-(azetidin-1-yl)-5-[5-(5-bromopyridin-2-yl)-1-methyl-1H-pyrazol-4-yl]-7-methylimidazo[5,1-f][1,2,4]triazine | 2.16-2.25 (m, 2H), 2.69 (s, 3H), 3.4-3.8 (v br m, 2H), 3.8-4.3 (v br m, 2H), 4.12 (s, 3H), 7.35 (d, J = 8.6 Hz, 1H), 7.64 (s, 1H), 7.69 (dd, J = 8.4, 2.3 Hz, 1H), 7.81 (s, 1H), 8.75 (d, J = 2.3 Hz, 1H); 427.2 |
| 78 | 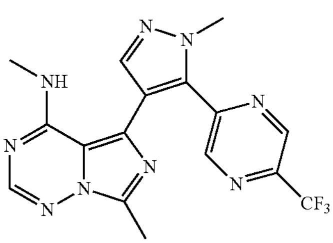 [SMILES: CNc1ncnn2c(C)nc(-c3cnn(C)c3-c3cnc(C(F)(F)F)cn3)c12] | Ex 7; C6 | N,7-dimethyl-5-{1-methyl-5-[5-(trifluoromethyl)pyrazin-2-yl]-1H-pyrazol-4-yl}imidazo[5,1-f][1,2,4]triazin-4-amine | 2.66 (s, 3H), 3.02 (d, J = 5.0 Hz, 3H), 4.23 (s, 3H), 5.48-5.54 (m, 1H), 7.72 (s, 1H), 7.94 (s, 1H), 8.99-9.01 (m, 2H); 390.1 |
| 79 | 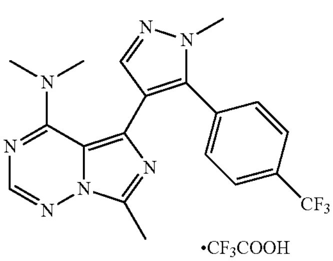 [SMILES: Cc1nc(-c2cnn(C)c2-c2ccc(C(F)(F)F)cc2)c2c(N(C)C)ncnn12 ; "·CF3COOH"] | Ex 12[14]; C3 | N,N,7-trimethyl-5-{1-methyl-5-[4-(trifluoromethyl)phenyl]-1H-pyrazol-4-yl}imidazo[5,1-f][1,2,4]triazin-4-amine, trifluoroacetate salt | 2.34[15]; 402.3 |

TABLE 1-continued

| Ex No | Structure | Method of Prep; starting material | IUPAC Name | $^1$H NMR (400 MHz, CDCl$_3$), δ (ppm); LCMS, observed ion m/z (M + 1) or HPLC retention time (minutes); MS observed ion m/z (M + 1) (unless otherwise indicated) |
|---|---|---|---|---|
| 80 | 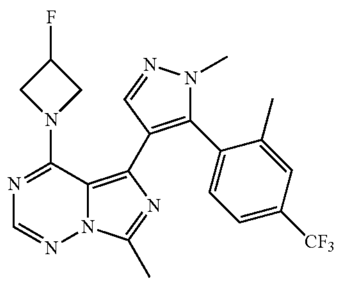 [SMILES: Cc1cc(C(F)(F)F)ccc1-c1c(-c2nc(C)n3ncnc(N4CC(F)C4)c23)cnn1C] | Ex 12[5,6,14]; C3 | 4-(3-fluoroazetidin-1-yl)-7-methyl-5-{1-methyl-5-[2-methyl-4-(trifluoromethyl)phenyl]-1H-pyrazol-4-yl}imidazo[5,1-f][1,2,4]triazine | 2.61[15]; 446.3 |
| 81 | ·CF$_3$COOH | Ex 12[14]; C3 | 4-(3-fluoroazetidin-1-yl)-5-{5-[2-fluoro-4-(trifluoromethyl)phenyl]-1-methyl-1H-pyrazol-4-yl}-7-methylimidazo[5,1-f][1,2,4]triazine, trifluoroacetate salt | 2.53[15]; 450.3 |
| 82 | ·CF$_3$COOH | Ex 2; C1[13,14] | methyl [1-(7-methyl-5-{1-methyl-5-[5-(trifluoromethyl)pyridin-2-yl]-1H-pyrazol-4-yl}imidazo[5,1-f][1,2,4]triazin-4-yl)azetidin-3-yl]carbamate, trifluoroacetate salt | 2.14[15]; 488.3 |

TABLE 1-continued

| Ex No | Structure | Method of Prep; starting material | IUPAC Name | $^1$H NMR (400 MHz, CDCl$_3$), δ (ppm); LCMS, observed ion m/z (M + 1) or HPLC retention time (minutes); MS observed ion m/z (M + 1) (unless otherwise indicated) |
|---|---|---|---|---|
| 83 | 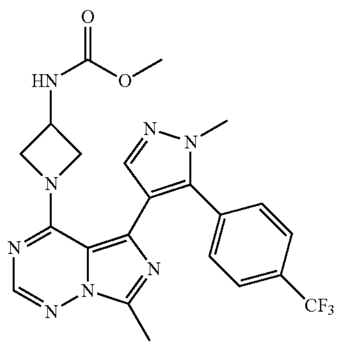 [SMILES: COC(=O)NC1CN(c2ncnn3c(C)nc(-c4cnn(C)c4-c4ccc(C(F)(F)F)cc4)c23)C1] | Ex 82; C1 | methyl [1-(7-methyl-5-{1-methyl-5-[4-(trifluoromethyl)phenyl]-1H-pyrazol-4-yl}imidazo[5,1-f][1,2,4]triazin-4-yl)azetidin-3-yl]carbamate | $^1$H NMR (400 MHz, CD$_3$OD): 2.57 (s, 3H), 3.4-4.6 (v br m, 4H), 3.63 (s, 3H), (s, 3H), 4.29-4.39 (m, 1H), 7.59 (br d, J = 8 Hz, 2H), 7.70 (br d, J = 8 Hz, 2H), 7.71 (s, 1H) 7.75 (s, 1H); 487.2 |
| 84 | 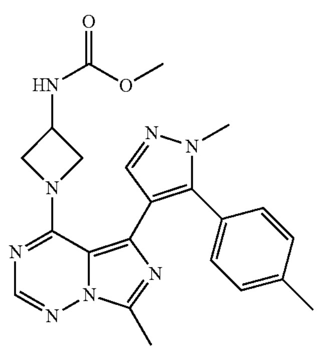 | Ex 82$^{14}$; C1 | methyl (1-{7-methyl-5-[1-methyl-5-(4-methylphenyl)-1H-pyrazol-4-yl]imidazo[5,1-f][1,2,4]triazin-4-yl}azetidin-3-yl)carbamate, trifluoroacetate salt | 2.05$^{15}$; 433.4 |
| 85 | 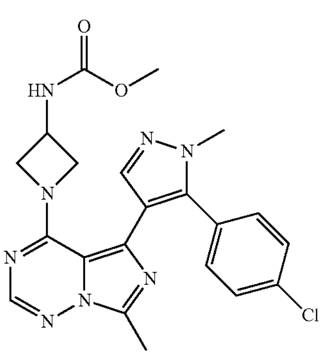 | Ex 82$^{14}$; C1 | methyl (1-{5-[5-(4-chlorophenyl)-1-methyl-1H-pyrazol-4-yl]-7-methylimidazo[5,1-f][1,2,4]triazin-4-yl}azetidin-3-yl)carbamate, trifluoroacetate salt | 2.16$^{15}$; 453.3, 455.3 |

TABLE 1-continued

| Ex No | Structure | Method of Prep; starting material | IUPAC Name | $^1$H NMR (400 MHz, CDCl$_3$), δ (ppm); LCMS, observed ion m/z (M + 1) or HPLC retention time (minutes); MS observed ion m/z (M + 1) (unless otherwise indicated) |
|---|---|---|---|---|
| 86 | 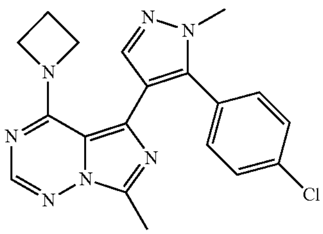 [SMILES: Cc1nc(-c2cnn(C)c2-c2ccc(Cl)cc2)c2c(N3CCC3)ncnn12] | Ex 12[14]; C8 | 4-(azetidin-1-yl)-5-[5-(4-chlorophenyl)-1-methyl-1H-pyrazol-4-yl]imidazo[5,1-f][1,2,4]triazine | 2.21[15]; 366.0, 368.0 |

[1]Palladium(II) acetate was used instead of allylpalladium(II) chloride dimer.
[2]In this case, tris(dibenzylideneacetone)dipalladium(0) and tricyclohexylphosphine were used in place of tetrakis(triphenylphosphine)palladium(0), and the reaction was carried out in aqueous 1,4-dioxane.
[3]The intermediate 5-[5-(2-fluoro-4-methoxyphenyl)-1-methyl-1H-pyrazol-4-yl]-7-methylimidazo[5,1-f][1,2,4]triazin-4(3H)-one was converted to 4-chloro-5-[5-(2-fluoro-4-methoxyphenyl)-1-methyl-1H-pyrazol-4-yl]-7-methylimidazo[5,1-f][1,2,4]triazine with phosphorus oxychloride; reaction with azetidine according to the general procedure for preparation of C2 in Example 4 provided the product.
[4]C1 was converted to N,7-dimethyl-5-(1-methyl-1H-pyrazol-4-yl)imidazo[5,1-f][1,2,4]triazin-4-amine using the general procedure for preparation of C4 in Example 3. Reaction with lithium bis(trimethylsilyl)amide and di-tert-butyl dicarbonate provided tert-butyl methyl[7-methyl-5-(1-methyl-1H-pyrazol-4-yl)imidazo[5,1-f][1,2,4]triazin-4-yl]carbamate, which was converted to the product according to the procedures of Example 7.
[5]Copper(I) chloride (1 equivalent) and potassium bromide (1 equivalent) were added to the Suzuki reaction, which was carried out in 1,2-dimethoxyethane.
[6]In this case, the reaction was carried out with a 4,4,5,5-tetramethyl-1,3,2-dioxaborolan-2-yl derivative, rather than a boronic acid.
[7]This preparation employed 5-chloro-2-(4,4,5,5-tetramethyl-1,3,2-dioxaborolan-2-yl)benzonitrile, which was prepared from 2-bromo-5-chlorobenzonitrile using the general method for preparation of C5 in Example 6.
[8]The requisite aryl bromide was prepared from 2-bromo-5-methylbenzoic acid by conversion of the carboxylic acid to a cyano group.
[9]The requisite pyridyl bromide was prepared from 6-bromonicotinaldehyde by treatment with (diethylamino)sulfur trifluoride.
[10]The synthesis was carried out with 2-bromo-5-(2-methyl-1,3-dioxolan-2-yl)pyridine, which can be prepared as described by M. Hatanaka et al., *Bioorg. Med. Chem.* 2005, 13, 6763-6770
[11]This preparation employed 5-methyl-2-(4,4,5,5-tetramethyl-1,3,2-dioxaborolan-2-yl)benzonitrile, which was prepared from 2-bromo-5-methylbenzonitrile using the general method for preparation of C5 in Example 6.
[12]The compound of Example 70 was hydrogenated over palladium on carbon, and the resulting aniline was subjected to a Sandmeyer reaction using tert-butyl nitrite and copper(II) bromide.
[13]1-(Diphenylmethyl)azetidin-3-amine was reacted with methyl chloroformate, followed by hydrogenation over palladium hydroxide, to afford the requisite amine reagent.
[14]The final compound was purified using one of the following methods: a) Reversed-phase HPLC; Column: Waters Sunfire C18, 19 × 100 mm, 5 µm; Mobile phase A: 0.05% trifluoroacetic acid in water (v/v); Mobile phase B: 0.05% trifluoroacetic acid in acetonitrile (v/v); Gradient: 5% to 100% B; b) Reversed-phase HPLC; Column: Waters XBridge C18, 19 × 100 mm, 5 µm; Mobile phase A: 0.03% ammonium hydroxide in water (v/v); Mobile phase B: 0.03% ammonium hydroxide in acetonitrile (v/v); Gradient: 15% to 100% B.
[15]HPLC conditions: Column: Waters Atlantis dC18, 4.6 × 50 mm, 5 µm; Mobile phase A: 0.05% trifluoroacetic acid in water (v/v); Mobile phase B: 0.05% trifluoroacetic acid in acetonitrile (v/v); Gradient: linear, 5% to 95% B over 4.0 minutes; Flow rate: 2 mL/minute.

TABLE 2

| Ex Number | PDE2-A3 IC$_{50}$; Geometric mean of 2-5 determinations, unless otherwise indicated (nM) |
|---|---|
| 1 | 1.31 |
| 2 | 1.61 |
| 3 | 1.25[b] |
| 4 | 1.26 |
| 5 | 8.19[b] |
| 6 | 6.13[b] |
| 7 | 10.7[b] |
| 8 | 0.578 |
| 9 | 0.763 |
| 10 | 1.30 |
| 11 | 9.21 |
| 12 | 2.68 |
| 13 | 0.303 |
| 14 | 1.25 |
| 15 | 0.517 |
| 16 | 322[a] |
| 17 | 2.33[b] |
| 18 | 11.6 |
| 19 | 1.47 |
| 20 | 10.5[a] |
| 21 | 37.2[a] |
| 22 | 112 |
| 23 | 289 |
| 24 | 9.11[a] |
| 25 | 10.6[a] |
| 26 | 5.95[a] |
| 27 | 91.3[a] |
| 28 | 71.9[a] |
| 29 | 251[a] |
| 30 | 260[a] |
| 31 | 29.8[a] |
| 32 | 7.89 |
| 33 | 17.3 |
| 34 | 1.00 |
| 35 | 20.1[a] |
| 36 | 0.825 |
| 37 | 37.2[a] |
| 38 | 23.4 |
| 39 | 13.7 |
| 40 | 13.6[b] |
| 41 | 67.2 |
| 42 | 7.89 |
| 43 | 1.32 |
| 44 | 3.47 |
| 45 | 18.3[a] |
| 46 | 16.9 |
| 47 | 3.34 |
| 48 | 30.0 |

TABLE 2-continued

| Ex Number | PDE2-A3 IC$_{50}$; Geometric mean of 2-5 determinations, unless otherwise indicated (nM) |
|---|---|
| 49 | 1.01 |
| 50 | 1.59 |
| 51 | 0.959 |
| 52 | 0.633 |
| 53 | 2.01 |
| 54 | 1.69 |
| 55 | 1.08 |
| 56 | 7.55 |
| 57 | 0.761 |
| 58 | 1.30 |
| 59 | 3.81 |
| 60 | 4.28 |
| 61 | 15.4 |
| 62 | 2.24 |
| 63 | 5.00 |
| 64 | 60.7$^a$ |
| 65 | 42.0$^a$ |
| 66 | 21.8 |
| 67 | 1.02 |
| 68 | 1.18 |
| 69 | 7.00 |
| 70 | 96.7$^a$ |
| 71 | 96.6$^a$ |
| 72 | 108$^a$ |
| 73 | 4.91 |
| 74 | 21.6$^a$ |
| 75 | 1.55 |
| 76 | 89.6$^a$ |
| 77 | 6.30 |
| 78 | 26.8$^a$ |
| 79 | 2.30 |
| 80 | 2.77 |
| 81 | 1.08 |
| 82 | 5.45 |
| 83 | 0.975 |
| 84 | 4.59 |
| 85 | 2.89 |
| 86 | 66.1$^a$ |

$^a$Single determination
$^b$Value represents the geometric mean of 6-13 IC$_{50}$ determinations Biological Assays and Data The compounds of Formula I (and Formulae Ia-Ix) are useful for modulating or inhibiting PDE2 activity. Certain compounds of the invention are selective modulators or inhibitors of PDE2 as compared to other PDE receptor subtypes. Accordingly, these compounds of the invention are useful for the prevention and/or treatment of a disease or condition of the central nervous system such as cognitive disorders, schizophrenia, and dementia in a mammal, preferably a human.

The term "inhibiting PDE 2", as used herein, means the prevention of or therapeutically significant reduction in PDE2 activity. One of ordinary skill in the art is readily able to determine whether a compound inhibits PDE2 activity. For example, assays which may conveniently be used in order to assess the PDE2 inhibition may be found in U.S. Patent Application Publication No. 2006/0154931 (U.S. Ser. No. 11/326,221) published on Jul. 13, 2006, herein incorporated by reference in its entirety. In general, a substance is considered to effectively inhibit PDE2 activity if it has an IC$_{50}$ of less than or about 10 µM, preferably less than or about 0.1 µM.

A "selective PDE2 inhibitor" can be identified, for example, by comparing the ability of a substance to inhibit PDE2 activity to its ability to inhibit PDE enzymes from the other PDE families. For example, a substance may be assayed for its ability to inhibit PDE2 activity, as well as PDE1A, PDE1B, PDE1C, PDE3A, PDE3B, PDE4A, PDE4B, PDE4C, PDE4D, PDE5, PDE6, PDE7, PDE8, PDE9, PDE10 and PDE11 activities. In one embodiment, a selective PDE2 inhibitor is a compound of the invention having a K$_i$ for inhibition of PDE2 that is less than or about one-tenth the K$_i$ that the substance has for inhibition of any other PDE enzyme. In other words, the compound inhibits PDE2 activity to the same degree at a concentration of about one-tenth or less than the concentration required for inhibition of any other PDE enzyme.

Measurement of Recombinant Human PDE2A3 Inhibition by SPA Technology

In the present assay, the activity of the test substances on human full-length PDE2A3 enzyme was determined using the [$^3$H]-cGMP scintillation proximity assay (SPA) modified from the Amersham TRKQ7100 instructions (GE Healthcare, USA). PDE2A3 protein was obtained from FLAG purification of sf21 insect cells using standard affinity purification procedures for this tag (anti-FLAG M2, Sigma Aldrich). Briefly, the SPA assays were performed using PDE SPA yttrium silicate beads (Perkin Elmer RPNQ0024) which bind preferentially to the linear nucleotide, GMP, compared to the cyclic nucleotide, cGMP. The, $^3$H-GMP product was detected using a Wallac MicroBeta scintillation counter. The reaction time was chosen with respect to the amount of time in which 10-20% of substrate was hydrolyzed by the enzyme.

The assay was validated using PDE2-selective literature compounds, erythro-9-(2-hydroxy-3-nonyl) adenine (EHNA) and BAY 60-7550 as controls before testing the representative compounds of the present invention (Podzuweit et al., *Isozyme selective inhibition of cGMP-stimulated cyclic nucleotide phosphodiesterases by erythro-9-(2-hydroxy-3-nonyl) adenine*, Cell Signal, 7(7):733-8, 1995, Boess et al., *Inhibition of phosphodiesterase 2 increases neuronal cGMP, synaptic plasticity and memory performance*, Neuropharmacology, 47(7):1081-92, 2004). The IC$_{50}$ values obtained were within 3× of literature values, 1.7 µM for EHNA and 4.66 uM for BAY 60-7550. The corresponding IC$_{50}$ values of the compounds for the inhibition of PDE activities are determined from the concentration-effect curves by means of non-linear regression.

The invention claimed is:

1. A compound of the Formula I

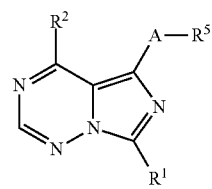

or a pharmaceutically acceptable salt thereof, wherein:
"-A-R$^5$" is:

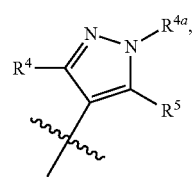 A1R⁵

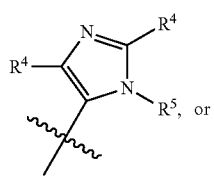 A2R⁵, or

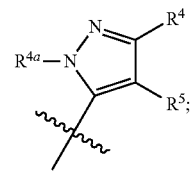 A3R⁵;

$R^1$ is hydrogen, $(C_1-C_6)$alkyl, $(C_2-C_6)$alkenyl, $(C_2-C_6)$alkynyl, $(C_3-C_{15})$cycloalkyl, —$(C_1-C_6)$alkyl-OH, —$(C_1-C_6)$alkyl-CN, —$SF_5$, —$CF_3$, —$CHF_2$, or —$CH_2F$;

$R^2$ is —$(C_1-C_6)$alkyl-$R^9$, —$NHR^3$, —$N(R^3)_2$, —O—$(C_1-C_6)$alkyl-$R^9$, —$OR^8$, $(C_3-C_{15})$cycloalkyl, $(C_6-C_{10})$aryl, (3- to 14-membered)heterocyclic, and (5- to 14-membered)heteroaryl; wherein said $(C_3-C_{15})$cycloalkyl and (3- to 14- membered)heterocyclic may optionally contain one double or triple bond and one to two oxo (O=) groups; and wherein said —$(C_1-C_6)$alkyl-$R^9$, —$NHR^3$, —$N(R^3)_2$, —O—$(C_1-C_6)$alkyl-$R^9$, —$OR^8$, $(C_3-C_{15})$cycloalkyl, $(C_6-C_{10})$aryl, (3- to 14-membered)heterocyclic, or (5- to 14- membered)heteroaryl moieties may be optionally substituted with one to three substituents independently selected from the group consisting of $(C_1-C_6)$alkyl, $(C_1-C_6)$alkoxy, halo, and —$CF_3$;

Each $R^3$ is independently selected from the group consisting of —$(C_1-C_6)$alkyl-$R^9$, —$(C2-C6)$alkenyl-$R^9$, —$(C_2-C_6)$alkynyl-$R^9$, and —$(C_3-C_{15})$cycloalkyl-$R^9$, or when $R^2$ is —$N(R^3)_2$ both of said $R^3$ may be taken together with the nitrogen atom to which they are attached to form a 4- to 6-membered heterocyclic ring optionally containing one or two oxo groups (O=) and optionally substituted with one to three substituents independently selected from the group consisting of hydrogen, fluoro, —CN, —$CF_3$, —$CHF_2$, —$CH_2F$, —OH, —O—$(C_1-C_6)$alkyl, $NH_2$, —NH—$(C_1-C_6)$alkyl, —N[$(C_1-C_6)$alkyl]$_2$, $(C_1-C_6)$alkyl, $(C_2-C_6)$alkenyl, $(C_2-C_6)$alkynyl, —(C=O)—$R^8$, —(C=O)—$OR^8$, —(C=O)—$N(R^8)_2$, —O—(C=O)—$R^8$, —$OR^8$, —O—(C=O)—$OR^8$, —$SR^8$, —$S(O)R^8$, —$S(O)_2R^8$, —$S(O)_2N(R^8)_2$, —NH—(C=O)—$R^8$, —NH—(C=O)—$OR^8$, —O—(C=O)—$N(R^8)_2$, —NH—(C=O)—$N(R^8)_2$, —N[$(C_1-C_6)$alkyl](C=O)—$R^8$, —N[$(C_1-C_6)$alkyl](C=O)—$OR^8$, —N[$(C_1-C_6)$alkyl](C=O)—$N(R^8)_2$, $(C_3-C_{15})$cycloalkyl, $(C_6-C_{10})$aryl, (3- to 14-membered)heterocyclic and (5- to 14-membered)heteroaryl; wherein said $(C_3-C_{15})$cycloalkyl and (3- to 14- membered)heterocyclic moieties may optionally contain one double or triple bond and one to two oxo (O=) groups, Each $R^4$ is independently selected from the group consisting of hydrogen, halo, $(C_1-C_6)$alkyl, $(C_2-C_6)$alkenyl, $(C_2-C_6)$alkynyl, —$CF_3$, —$CHF_2$, —$CH_2F$, and $(C_3-C_{15})$cycloalkyl;

Each $R^{4a}$ is independently selected from the group consisting of hydrogen, $(C_1-C_6)$alkyl, $(C_3-C_4)$alkenyl, $(C_3-C_4)$alkynyl, —$CF_3$, —$CHF_2$, —$CH_2F$, and $(C_3-C_{15})$cycloalkyl;

$R^5$ is:

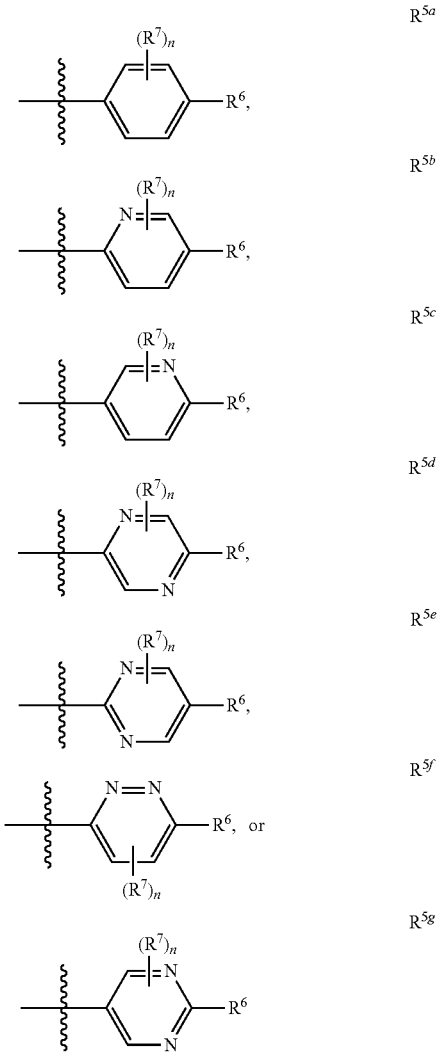

where n is 0, 1, 2, 3, or 4;

Each $R^6$ is independently selected from the group consisting of hydrogen, halo, (C1-C6)alkyl, —$CF_3$, —$CHF_2$, —$CH_2F$, —$CF_2$—$(C_1-C_6)$alkyl, —$SF_5$, —CN, —$(C_1-C_6)$alkyl-CN, —$NO_2$, —(C=O)—$R^8$, —(C=O)—$OR^8$, —$OR^8$, —O—(C=O)—$N(R^8)_2$, —$SR^8$, —$S(O)R^8$, —$S(O)_2R^8$, $NH_2$, —NH—$(C_1-C_6)$alkyl, —N[$(C_1-C_6)$alkyl]$_2$, —NH—(C=O)—$R^8$, —NH—(C=O)—$OR^8$, —N[$(C_1-C_6)$alkyl](C=O)—$R^8$, —N[$(C_1-C_6)$alkyl](C=O)—$OR^8$, $(C_1-C_6)$alkyl, $(C_2-C_6)$alkenyl, $(C_2-C_6)$alkynyl, $(C_3-C_{15})$cycloalkyl, (3- to 14-membered)heterocyclic, $(C_6-C_{10})$aryl, and (5- to 14- membered)heteroaryl; wherein said $(C_3-C_{15})$cycloalkyl and (3- to 14- membered)heterocyclic moieties may optionally contain one double or triple bond and one to two oxo (O=) groups;

Each R⁷ is independently selected from the group consisting of hydrogen, halo, $(C_1-C_6)$alkyl, $(C_2-C_4)$alkenyl, $(C_2-C_6)$alkynyl, —CN, —CF₃, —CHF₂, —CH₂F, —O—$(C_1-C_6)$alkyl and $(C_3-C_{15})$cycloalkyl;

Each R⁸ wherever it occurs is independently selected from the group consisting of hydrogen, $(C_1-C_6)$alkyl, $(C_3-C_{15})$cycloalkyl, —CF₃, and —CHF₂; and Each R⁹ is independently selected from the group consisting of hydrogen, halo, —CF₃, —CHF₂, —CH₂F, —CF₂—$(C_1-C_6)$alkyl, —CN, —$(C_1-C_6)$alkyl-CN, —NO₂, —(C=O)—R⁸, —(C=O)—OR⁸, —OR⁸, —O—(C=O)—N(R⁸)₂, —SR⁸, —S(O)R⁸, —S(O)₂R⁸, NH₂, —NH—$(C_1-C_6)$alkyl, —N[$(C_1-C_6)$alkyl]₂, —NH—(C=O)—R⁸, —NH—(C=O)—OR⁸, —N[$(C_1-C_6)$alkyl](C=O)—R⁸, —N[$(C_1-C_6)$alkyl](C=O)—OR⁸, $(C_1-C_6)$alkyl, $(C_2-C_6)$alkenyl, $(C_2-C_6)$alkynyl, $(C_3-C_{15})$cycloalkyl, (3- to 14-membered)heterocyclic, $(C_6-C_{10})$aryl, and (5- to 14-membered)heteroaryl, wherein said $(C_3-C_{15})$cycloalkyl and (3- to 14-membered)heterocyclic moieties may optionally contain one double or triple bond and one to two oxo (O=) groups; and wherein each of said $(C_3-C_{15})$cycloalkyl, (3- to 14-membered)heterocyclic, $(C_6-C_{10})$aryl, and (5- to 14-membered)heteroaryl moieties may be optionally substituted with one to three substituents independently selected from $(C_1-C_6)$alkyl, $(C_1-C_6)$alkoxy, halo, and —CF₃.

2. The compound according to claim 1, or a pharmaceutically acceptable salt thereof, wherein:

"-A-R⁵" is:

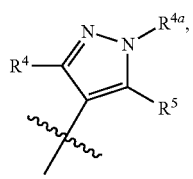

R¹ is —$(C_1-C_6)$alkyl;
R² is —NHR³, or —N(R³)₂;
Each R³ is independently selected from the group consisting of —$(C_1-C_6)$alkyl-R⁹, —$(C_2-C_6)$alkenyl-R⁹, —$(C_2-C_6)$alkynyl-R⁹, and —$(C_3-C_{15})$cycloalkyl-R⁹; or when R² is —N(R³)₂ both of said R³ may be taken together with the nitrogen atom to which they are attached to form a 4- to 6-membered heterocyclic ring optionally containing one or two oxo groups (O=); and optionally may be substituted with one to three substituents independently selected from the group consisting of hydrogen, fluoro, —CN, —CF₃, —CHF₂, —CH₂F, —OH, —O—$(C_1-C_6)$alkyl, NH₂, —NH—$(C_1-C_6)$alkyl, —N[$(C_1-C_6)$alkyl]₂, $(C_1-C_6)$alkyl, $(C_2-C_6)$alkenyl, $(C_2-C_6)$alkynyl, —(C=O)—R⁸, —(C=O)—OR⁸, —(C=O)—N(R⁸)₂—O—(C=O)—R⁸, —OR⁸, —O—(C=O)—OR⁸, —SR⁸, —S(O)R⁸, —S(O)₂R⁸, —S(O)₂N(R⁸)₂, —NH—(C=O)—R⁸, —NH—(C=O)—OR⁸, —O—(C=O)—N(R⁸)₂, —NH—(C=O)—N(R⁸)₂, —N[$(C_1-C_6)$alkyl](C=O)—R⁸, —N[$(C_1-C_6)$alkyl](C=O)—OR⁸, —N[$(C_1-C_6)$alkyl](C=O)—N(R⁸)₂, $(C_3-C_{15})$cycloalkyl, $(C_6-C_{10})$aryl, (3- to 14-membered)heterocyclic, and (5- to 14-membered)heteroaryl; wherein said $(C_3-C_{15})$cycloalkyl and (3- to 14-membered)heterocyclic moieties may optionally contain one double or triple bond and one to two oxo (O=) groups;

R⁴ is hydrogen;
R⁴ᵃ is $(C_1-C_6)$alkyl;
R⁵ is:

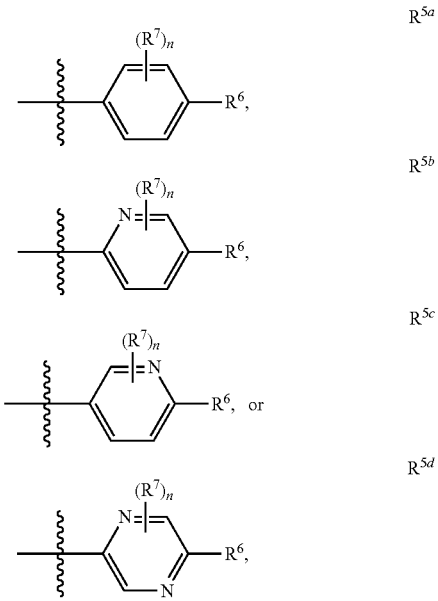

where n is 0, 1, 2, 3, or 4.

3. The compound according to claim 1, or a pharmaceutically acceptable salt thereof, having the formula

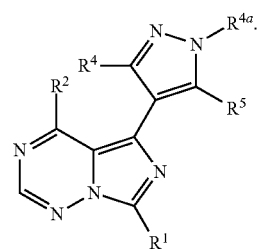

4. The compound according to claim 1, or a pharmaceutically acceptable salt thereof, having the formula

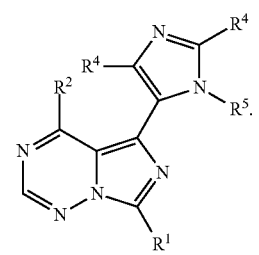

5. The compound according to claim 1, or a pharmaceutically acceptable salt thereof, having the formula

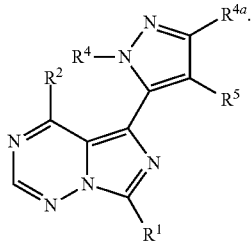

Ia

6. The compound according to claim 1, or a pharmaceutically acceptable salt thereof, wherein $R^5$ is:

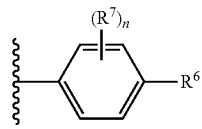

7. The compound according to claim 1, or a pharmaceutically acceptable salt thereof, wherein $R^5$ is:

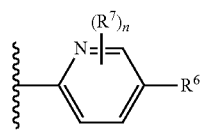

8. The compound according to claim 1, or a pharmaceutically acceptable salt thereof, wherein $R^5$ is:

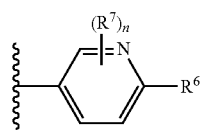

9. The compound according to claim 1, or a pharmaceutically acceptable salt thereof, wherein $R^5$ is:

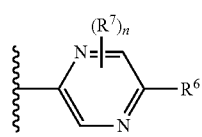

10. The compound according to claim 1, or a pharmaceutically acceptable salt thereof, wherein $R^5$ is:

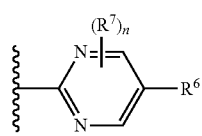

11. The compound according to claim 1, or a pharmaceutically acceptable salt thereof, wherein $R^5$ is:

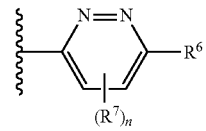

12. The compound according to claim 1, or a pharmaceutically acceptable salt thereof, wherein $R^5$ is:

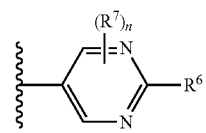

13. The compound according to claim 1, or a pharmaceutically acceptable salt thereof, wherein $R^2$ is —($C_1$-$C_6$)alkyl-$R^9$, —$NHR^3$, —$N(R^3)_2$, —O—($C_1$-$C_6$)alkyl-$R^9$, or —$OR^8$.

14. The compound according to claim 1, or a pharmaceutically acceptable salt thereof, wherein $R^2$ is —$N(R^3)_2$, or —$NHR^3$.

15. The compound according to claim 1, or a pharmaceutically acceptable salt thereof, wherein $R^2$ is ($C_3$-$C_{15}$)cycloalkyl, ($C_6$-$C_{10}$)aryl, (3- to 14-membered)heterocyclic, or (5- to 14-membered)heteroaryl; wherein said ($C_3$-$C_{15}$)cycloalkyl and (3- to 14-membered)heterocyclic moieties may optionally contain one or two double or triple bonds and one to three oxo (O=) groups.

16. The compound according to claim 1, or a pharmaceutically acceptable salt thereof, wherein $R^6$ is selected from the group consisting of hydrogen, halo, —$CF_3$, —$CHF_2$, and —$CH_2F$.

17. The compound according to claim 1, or a pharmaceutically acceptable salt thereof, wherein $R^6$ is selected from the group consisting of —(C=O)—$R^8$, —(C=O)—$OR^8$, —$OR^8$, —O—(C=O)—$N(R^8)_2$, —$SR^8$, —S(O)$R^8$, —S(O)$_2R^8$, $NH_2$, —NH—($C_1$-$C_6$)alkyl, —N[($C_1$-$C_6$)alkyl]$_2$, —NH—(C=O)—$R^8$, —NH—(C=O)—$OR^8$, —O—(C=O)—$N(R^8)_2$, —N(($C_1$-$C_6$)alkyl)-(C=O)—$R^8$, and —N(($C_1$-$C_6$)alkyl)-(C=O)—$OR^8$.

18. The compound according to claim 1, or a pharmaceutically acceptable salt thereof, wherein $R^6$ is ($C_1$-$C_6$)alkyl or ($C_3$-$C_{15}$)cycloalkyl.

19. The compound according to claim 1, or a pharmaceutically acceptable salt thereof, wherein $R^6$ is selected from the group consisting of (C2-C6)alkenyl, ($C_2$-$C_6$)alkynyl, (3- to 14-membered)heterocyclic, ($C_6$-$C_{10}$)aryl, and (5- to 14-membered)heteroaryl.

20. The compound according to claim 1 wherein said compound is:
   4-(azetidin-1-yl)-7-methyl-5-[1-methyl-5-(4-methylphenyl)-1H-pyrazol-4-yl]imidazo[5,1-f][1,2,4]triazine;
   4-(azetidin-1-yl)-7-methyl-5-{1-methyl-5-[4-(trifluoromethyl)phenyl]-1H-pyrazol-4-yl}imidazo[5,1-f][1,2,4]triazine;
   4-(azetidin-1-yl)-7-methyl-5-{1-methyl-5-[5-(trifluoromethyl)pyridin-2-yl]-1H-pyrazol-4-yl}imidazo[5,1-f][1,2,4]triazine;
   4-(azetidin-1-yl)-5-[5-(4-chlorophenyl)-1-methyl-1H-pyrazol-4-yl]-7-methylimidazo[5,1-f][1,2,4]triazine;

4-(azetidin-1-yl)-5-[5-(5-chloropyridin-2-yl)-1-methyl-1H-pyrazol-4-yl]-7-methylimidazo[5,1-f][1,2,4]triazine;

5-{5-[4-(difluoromethyl)phenyl]-1-methyl-1H-pyrazol-4-yl}-N,7-dimethylimidazo[5,1-f][1,2,4]triazin-4-amine;

7-methyl-N-(d$_3$)methyl-5-{1-methyl-5-[4-(trifluoromethyl)phenyl]-1H-pyrazol-4-yl}imidazo[5,1-f][1,2,4]triazin-4-amine;

N,7-dimethyl-5-{1-methyl-5-[5-(trifluoromethyl)pyridin-2-yl]-1H-pyrazol-4-yl}imidazo[5,1-f][1,2,4]triazin-4-amine;

4-(azetidin-1-yl)-5-{5-[3-fluoro-5-(trifluoromethyl)pyridin-2-yl]-1-methyl-1H-pyrazol-4-yl}-7-methylimidazo[5,1-f][1,2,4]triazine;

N, 7-dimethyl-5-{1-methyl-5-[4-(trifluoromethoxy)phenyl]-1H-pyrazol-4-yl}imidazo[5,1-f][1,2,4]triazin-4-amine;

4-(azetidin-1-yl)-5-{5-[4-(difluoromethyl)phenyl]-1-methyl-1H-pyrazol-4-yl}-7-methylimidazo[5,1-f][1,2,4]triazine;

4-(3-fluoroazetidin-1-yl)-7-methyl-5-{1-methyl-5-[4-(trifluoromethyl)phenyl]-1H-pyrazol-4-yl}imidazo[5,1-f][1,2,4]triazine;

4-(azetidin-1-yl)-5-[5-(4-bromophenyl)-1-methyl-1H-pyrazol-4-yl]-7-methylimidazo[5,1-f][1,2,4]triazine;

4-(azetidin-1-yl)-5-{5-[4-(difluoromethoxy)phenyl]-1-methyl-1H-pyrazol-4-yl}-7-methylimidazo[5,1-f][1,2,4]triazine;

4-azetidin-1-yl-7-methyl-5-{1-methyl-5-[5-(trifluoromethyl)pyrazin-2-yl]-1H-pyrazol-4-yl}imidazo[5,1-][1,2,4]triazine;

4-azetidin-1-yl-5-[5-(5-bromopyridin-2-yl)-1-methyl-1H-pyrazol-4-yl]-7-methylimidazo[5,1-f][1,2,4]triazine; or N,7-dimethyl-5-{1-methyl-5-[5-(trifluoromethyl)pyrazin-2-yl]-1H-pyrazol-4-yl}imidazo[5,1-f][1,2,4]triazin-4-amine; or a pharmaceutically acceptable salt thereof.

21. A method for alleviating one or more symptoms of cognitive impairment associated with schizophrenia in a human, comprising administering to said human a therapeutically effective amount of the compound of Formula I according to claim 1, or a pharmaceutically acceptable salt thereof.

22. A pharmaceutical composition comprising a therapeutically effective amount of the compound of Formula I according to claim 1 or a pharmaceutically acceptable salt thereof together with a pharmaceutically acceptable carrier.

23. 4-(azetidin-1-yl)-7-methyl-5-{1-methyl-5-[5-(trifluoromethyl)pyridin-2-yl]-1H-pyrazol-4-yl}imidazol[5,1-f][1,2,4]triazine, or a pharmaceutically acceptable salt thereof.

24. 4-(azetidin-1-yl)-7-methyl-5-{1-methyl-5-[5-(trifluoromethyl)pyridin-2-yl]-1H-pyrazol-4-yl}imidazol[5,1-f][1,2,4]triazine.

25. A pharmaceutical composition comprising a therapeutically effective amount of the compound according to claim 23 together with a pharmaceutically acceptable carrier.

26. A method of alleviating one or more symptoms of migraine comprising:
administering to a patient in need thereof a therapeutically effective amount of the compound of Formula I according to claim 1, or a pharmaceutically acceptable salt thereof.

\* \* \* \* \*